(12) United States Patent
Mihara et al.

(10) Patent No.: US 6,207,435 B1
(45) Date of Patent: Mar. 27, 2001

(54) METHOD FOR PRODUCING NUCLEOSIDE-5'-PHOSPHATE ESTER

(75) Inventors: Yasuhiro Mihara, Kawasaki; Takashi Utagawa, Tokyo; Hideaki Yamada, Kyoto; Yasuhisa Asano, Imizu-gun, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/417,090

(22) Filed: Oct. 13, 1999

Related U.S. Application Data

(62) Division of application No. 08/975,698, filed on Nov. 21, 1997, now Pat. No. 6,015,697.

(30) Foreign Application Priority Data

Nov. 21, 1996 (JP) .................................................. 8-311103
Jun. 18, 1997 (JP) .................................................. 9-161674

(51) Int. Cl.[7] ............................... C12N 9/16; C12N 9/12
(52) U.S. Cl. ........................ 435/196; 435/194; 435/195
(58) Field of Search ................................ 435/194, 195, 435/196

(56) References Cited

FOREIGN PATENT DOCUMENTS

| | | |
|---|---|---|
| 39 29858 | 12/1964 | (JP) . |
| 42 1186 | 1/1967 | (JP) . |
| 53 56390 | 5/1978 | (JP) . |
| 56 82098 | 7/1981 | (JP) . |
| 63 230094 | 9/1988 | (JP) . |
| 07 231793 | 9/1995 | (JP) . |

OTHER PUBLICATIONS

Abstract for Congress of the Society for Fermentation and Bioengineering, p. 356, Oct. 10, 1994, Asano et al., "Phosphorylation of Nucleosides with Pyrophosphate as a Phosphate donor" (With English Translation).

Nippon Nogeikagaku Kaishi, vol. 69, p. 270 (20a10), Jul. 5, 1995, Mihara et al, "Enzymatic Phosphorylation Reaction of Nucleoside using Pyrophosphate as a Phosphate Donor" (With English Translation).

*Primary Examiner*—Nashaat T. Nashed
(74) *Attorney, Agent, or Firm*—Oblon, Spivak, McClelland, maier & Neustadt, P.C.

(57) ABSTRACT

A method for producing nucleoside-5'-phosphate esters inexpensively and in high yields by phosphorylating a nucleoside with a phospahte group donor using an acid phosphatase having an increased affinity for the nucleoside and/or an increased temperature stability at a pH of pH 3.0 to 5.5, to produce a nucleoside-5'-phosphate ester. Mutant acid phosphatases having increased affinity for nucleosides and/or an enhanced temperature stability are also provided.

3 Claims, 10 Drawing Sheets

SB: *Sau*3AI/*Bam*HIjunction   B: *Bam*HI   E: *Eco*RI   K: *K*pnI
H: *Hin*dIII   N: *Nco*I   P: *Pst*I SB: *Sau*3AI/*Bam*HI junction   E: *Eco*RI   H: *Hin*dIII   K: *Kpn*I
S: *Sac*I SB: *Sau*3AI/*Bam*HI junction  E: *Eco*RI  H: *Hin*dIII  P: *Pst*I

```
E. AEROGENES    1: MKKRVLALCLASLFSVNAFALVPAGNDATTKPDLYYLKNAQAIDSLALLP  50
E. BLATTAE      1: MKKRVLAVCFAALFSSQALALVATGNDTTTKPDLYYLKNSEAINSLALLP 50
K. PLANTICOLA   1: MKKRVLALCLASLFSVSAFALVPAGNDATTKPDLYYLKNAQAIDSLALLP 50
M. MORGANII     1: MKKNIIAGCLFSLFSLSALAAIPAGNDATTKPDLYYLKNEQAIDSLKLLP 50
P. STUARTII     1: MKKLLAVFCAGAFVSTSVFAAIPPGNDVTTKPDLYYLKNSQAIDSLALLP 50
S. FICARIA      1: MKK-ILLA-TLSCAALTQFS--FAAKDVTTHPEVYFLQESQSIDSLALLP 46
                   ***              * ** *  * *       * ** ***

E. AEROGENES   51: PPPEVGSIAFLNDQAMYEKGRLLRNTERGKLAAEDANLSAGGVANAFSSA 100
E. BLATTAE     51: PPPAVGSIAFLNDQAMYEQGRLLRNTERGKLAAEDANLSSGGVANAFSGA 100
K. PLANTICOLA  51: PPPEVGSIAFLNDQAMYEKGRLLRATARGKLAAEDANLSAGGVANAFSAA 100
M. MORGANII    51: PPPEVGSIQFLNDQAMYEKGRMLRNTERGKQAQADADLAAGGVATAFSGA 100
P. STUARTII    51: PPPEVGSILFLNDQAMYEKGRLLRNTERGEQAAKDADLAAGGVANAFSEA 100
S. FICARIA     47: PPPAMDSIDFLNDKAQYDAGKIVRNTPRGKQAYDDAHVAGDGVAAAFSNA  96
                   ***    ** **** * *   *  *  **   *  ***  ***

E. AEROGENES  101: FGSPITEKDAPQLHKLLTNMIEDAGDLATRSAKEKYMRIRPFAFYGVSTC 150
E. BLATTAE    101: FGSPITEKDAPALHKLLTNMIEDAGDLATRSAKDHYMRIRPFAFYGVSTC 150
K. PLANTICOLA 101: FGSPISEKDAPALHKLLTNMIEDAGDLATRGAKEKYMRIRPFAFYGVSTC 150
M. MORGANII   101: FGYPITEKDSPELYKLLTNMIEDAGDLATRSAKEHYMRIRPFAFYGTETC 150
P. STUARTII   101: FGYPITEKDAPEIHKLLTNMIEDAGDLATRSAKEKYMRIRPFAFYGVATC 150
S. FICARIA     97: FGLEIAQRKTPELFKLVMKMREDAGDLATRSAKNHYMRIRPFAFYNEATC 146
                   **  *    *  ** * ********* ** **********  **

E. AEROGENES  151: NTTEQDKLSKNGSYPSGHTSIGWATALVLAEINPQRQNEILKRGYELGES 200
E. BLATTAE    151: NTTEQDKLSKNGSYPSGHTSIGWATALVLAEINPQRQNEILKRGYELGQS 200
K. PLANTICOLA 151: NTTEQDKLSKNGSYPSGHTSIGWATALVLAEINPQRQNEILKRGYELGES 200
M. MORGANII   151: NTKDQKKLSTNGSYPSGHTSIGWATALVLAEVNPANQDAILERGYQLGQS 200
P. STUARTII   151: NTKDQDKLSKNGSYPSGHTAIGWASALVLSEINPENQDKILKRGYELGQS 200
S. FICARIA    147: RPDEESTLSKNGSYPSGHTTIGWATALVLAEINPARQGEILQRGYDMGQS 196
                   ** ********* **** **** * **  *   * **   * *

E. BLATTAE    201: RVICGYHWQSDVDAARVVGSAVVATLHTNPAFQQQLQKAKAEFAQHQKK 249
K. PLANTICOLA 201: RVICGYHWQSDVDAARIVGSAVVATLHTNPAFQQQLQKAKDEFAKQQK- 248
M. MORGANII   201: RVICGYHWQSDVDAARIVGSAAVATLHSDPAFQAQLAKAKQEFAQKSQK 249
E. AEROGENES  201: RVICGYHWQSDVDAARIVGSAVVATLHTNPAFQQQLQKAKDEFAKTQK- 248
P. STUARTII   201: RVICGYHWQSDVDAARIVASGAVATLHSNPEFQKQLQKAKDEFA-KLKK 248
S. FICARIA    197: RVICGYHWQSDVTAARMAASAMVARLHAEPTFAAQLQKAKDEF-NGLKK 244
                   ************ ***   * ** **  * *  ** *** **  **
```

*FIG. 12*

METHOD FOR PRODUCING NUCLEOSIDE-5'-PHOSPHATE ESTER

This is a division of application Ser. No. 08/975,698 filed on Nov. 21, 1997, now U.S. Pat. No. 6,015,697.

BACKGROUND OF THE INVENTION

1. Field of the Invention

The present invention relates to a method for producing nucleoside-5'-phosphate esters. The present invention also relates to a novel acid phosphatase, a gene coding for the acid phosphatase, a recombinant DNA containing the gene, and a microorganism harboring the recombinant DNA, which are useful for producing nucleoside-5'-phosphate esters. Nucleoside-5'-phosphate esters are useful as, for example, seasoning and pharmaceuticals.

2. Description of the Background

Methods for biochemically phosphorylating nucleosides to produce nucleoside-5'-phosphate esters by using the following phosphate group donors are known, such as a method which uses p-nitrophenyphosphoric acid (Japanese Patent Publication No. 39-29858), a method which uses inorganic phosphoric acid (Japanese Patent Publication No. 42-1186), a method which uses polyphosphoric acid (Japanese Patent Laid-open No. 53-56390), a method which uses acetylphosphoric acid (Japanese Patent Laid-open No. 56-82098), and a method which uses adenosine triphosphate (ATP) (Japanese Patent Laid-open No. 63-230094). However, these methods have not been satisfactory to produce nucleoside-5'-phosphate esters efficiently and inexpensively because the substrates are expensive, or because undesirable by-products are produced in the reaction.

Thus, the present inventors have developed a method for efficiently producing nucleoside-5'-phosphate ester without by-producing 2'-, 3'-nucleotide isomers by allowing cells of a specified microorganism to act under an acidic condition on a nucleoside and a phosphate group donor selected from the group consisting of polyphosphoric acid or a salt thereof, phenylphosphonic acid or a salt thereof, and carbamyl phosphate or a salt thereof (Japanese Patent Laid-open No. 7-231793).

However, even this method has had the following drawbacks. Namely, for example, a portion of the substrate is degraded during the reaction due to a nucleoside-degrading activity which unfortunately exists in a slight amount in the cells of the microorganism to be used. Moreover, if the reaction is continued, the produced and accumulated nucleoside-5'-phosphate ester is degraded. Therefore, by-products are produced in the reaction solution, and it has been impossible to obtain a sufficient yield. In addition, the reaction cannot be performed if the substrate is added at a high concentration because of a low transphosphorylation activity per microbial cell.

OBJECTS OF THE INVENTION

It is an object of the present invention is to provide a method for inexpensively and efficiently producing nucleoside-5'-phosphate esters via biochemical synthesis using an acid phosphatase. It is another object of the present invention is to provide a novel acid phosphatase, a gene coding for the acid phosphatase, a recombinant DNA containing the gene, and a microorganism harboring the recombinant DNA which are useful for producing nucleoside-5'-phosphate esters.

SUMMARY OF THE INVENTION

As a result of various investigations made by the present inventors in order to develop a method for producing nucleoside-5'-phosphate esters which is more efficient than the conventional methods, it has been found that nucleoside-5'-phosphate esters may be efficiently produced in high yield by using an acid phosphatase to catalyze the transfer of a phosphate group from a phosphate group donor to a nucleoside at a pH 3.0 to 5.5. Further, the present inventors have succeeded in obtaining wild type genes coding for acid phosphatases from various bacteria and genes coding for acid phosphatases having an increased affinity for the nucleoside as compared with the wild type acid phosphatase by introducing a mutation in an acid phosphatase derived from a bacterium belonging to the genus Escherichia. Moreover, the present inventors have discovered that the yield of nucleoside-5'-phosphate ester is remarkably improved by expressing the gene in large quantities using genetic engineering techniques.

Further, the present inventors have conducted experiments to prepare a mutant acid phosphatase with an increased temperature stability, in order to conduct the phosphate transfer reaction catalyzed by the acid phosphatase at a higher temperature. Conducting the reaction at higher temperature leads to more effective production of nucleoside-5'-phosphate esters because the reaction speed is elevated and the concentration of the nucleoside in the reaction solution may be higher. Also, the present inventors have succeeded in the preparation of a mutant acid phosphatase which has an increased temperature stability as compared to the mutant acid phosphatases described in Example 19 which may be used in a reactions at a high temperature.

Accordingly, the present invention provides a method for producing nucleoside-5'-phosphate esters by contacting (1) a nucleoside, (2) a phosphate group donor, and (3) an acid phosphatase having an increased affinity for the nucleoside and/or an increased temperature stability at a pH of 3.0 to 5.5, to produce a nucleoside-5'-phosphate ester, followed by isolating the nucleoside-5'-phosphate ester. In a preferred embodiment, the nucleoside and the phosphate group donor are cultured in the presence a microorganism transformed with a recombinant DNA comprising a gene encoding the acid phosphatase.

The objects of the present invention may also be accomplished with mutant acid phosphatases having an increased affinity for the nucleoside and/or an increased temperature stability, genes coding for the acid phosphatases, recombinant DNAs containing the genes, and microorganisms harboring, i.e., transformed with, the recombinant DNA.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying figures, wherein:

FIG. 12 illustrates amino acid sequences, using the standard one-letter code, deduced from nucleotide sequences of acid phosphatases derived from *Morganella morganii, Escherichia blattae, Providencia stuartii, Enterobacter aerogenes, Klebsiella planticola* and *Serratia ficaria*. These amino acid sequences are illustrated in SEQ ID NO: 4, 8, 22, 24, 26 and 28 in the Sequence Listing using the standard three-letter code. In the Figure, the amino acid residues which are common through the all amino acid sequences are marked with an * below the sequence.

Figure 1:
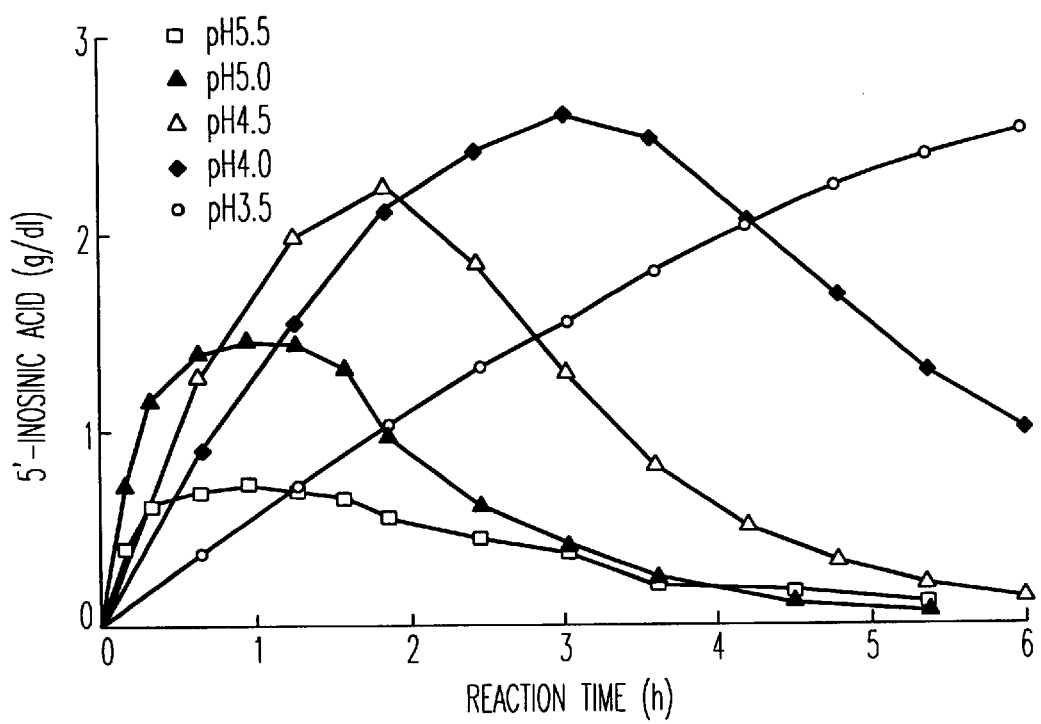
FIG. 1 illustrates the relationship between the reaction pH and the amount of 5'-inosinic acid produced in a reaction performed with the enzyme derived from *Morganella morganii*.

In the figures and in the specification, the symbol "dl", as in "g/dl", stands for deciliter.

DETAILED DESCRIPTION OF THE INVENTION

1. Preparation of Acid Phosphatase

The acid phosphatase to be used in the present invention is not specifically limited provided that it catalyzes the reaction to produce nucleoside-5'-phosphate ester by phosphate group transfer to the nucleoside from the phosphate group donor, for example, selected from the group consisting of polyphosphoric acid or a salt thereof, phenylphosphonic acid or a salt thereof, acetylphosphoric acid or a salt, and carbamyl phosphate or a salt thereof under the condition of pH 3.0 to 5.5. Such an acid phosphatase preferably includes those derived from microorganisms. In an especially preferred embodiment, the present invention uses an enzyme derived from a bacterium belonging to the genus Morganella, Escherichia, Providencia, Enterobacter, Klebsiella or Serratia. Representative examples of such a bacterium include the following bacterial strains:

*Morganella morganii* NCIMB 10466
*Morganella morganii* IFO 3168
*Morganella morganii* IFO 3848
*Escherichia blattae* JCM 1650
*Escherichia blattae* ATCC 33429
*Escherichia blattae* ATCC 33430
*Providencia stuartii* ATCC 29851
*Providencia stuartii* ATCC 33672
*Enterobacter aerogenes* IFO 12010
*Enterobacter aerogenes* IFO 13534
*Klebsiella planticola* IFO 14939
*Klebsiella planticola* IAM 1133
*Serratia ficaria* IAM 13540
*Serratia marcescens* IAM 12143

It is noted that acid phosphatase (EC 3.1.3.2) is originally an enzyme which catalyzes a reaction to hydrolyze phosphate ester under an acidic condition, and it has a nucleotidase activity to degrade nucleoside-5'-phosphate ester produced by the transphosphorylation reaction (hereinafter, the nucleotidase activity is referred to as "phosphomonoesterase activity"). Even such an acid phosphatase can be used in the method for producing nucleoside-5'-phosphate ester of the present invention. However, in order to obtain nucleoside-5'-phosphate ester at a high yield, it is desirable to use the mutant acid phosphatase in which an affinity for a nucleoside in the transphosphorylation reaction onto the nucleoside is increased as compared with the wild type acid phosphatase produced by the bacteria as described above (hereinafter simply referred to as "mutant acid phosphatase", if necessary). Preferably, the mutant acid phosphatase having a $K_m$ value below 100 mM is used. More preferably, the $K_m$ value is below 90 mM, even more preferably below 60 mM and, most preferably, below 45 mM. For a discussion of $K_m$ and other variables related to enzyme kinetics used in this disclosure, see A. Fersht, *Enzyme Structure and Mechanism*, Second Edition, W. H. Freeman and Company, New York, 1985, incorporated herein by reference in its entirety.

The mutant acid phosphatase may be obtained by expressing a mutant gene obtained by directly mutating a gene coding for an acid phosphatase as described below. Alternatively, the mutant acid phosphatase may be also obtained by treating a microorganism which produces an acid phosphatase having an increased affinity for a nucleoside with irradiation of ultraviolet light or a chemical mutating agent usually used for artificial mutation such as N-methyl-N'-nitro-N-nitrosoguanidine (NTG), and cultivating the mutated microorganism in order to produce the mutant acid phosphatase having an increased affinity for a nucleoside.

A protein having the desired acid phosphatase activity may be obtained from the microorganisms as described above by cultivating the microbial strain having the activity in an appropriate medium, harvesting proliferated microbial cells, disrupting the microbial cells to prepare a cell-free extract, and adequately purifying the protein therefrom.

The medium for cultivating the microorganism is not specifically limited, for which an ordinary medium may be available, containing an ordinary carbon source, a nitrogen source, inorganic ions, and optionally an organic nutrient source. The carbon source to be adequately used includes, for example, saccharides such as glucose and sucrose, alcohols such as glycerol, and organic acids. The nitrogen source to be used includes, for example, ammonia gas, aqueous ammonia, and ammonium salts. The inorganic ions to be adequately used if necessary include, for example, magnesium ion, phosphate ion, potassium ion, iron ion, and manganese ion. The organic nutrient source to be adequately used includes, for example, vitamins and amino acids as well as those containing them such as yeast extract, peptone, meat extract, corn steep liquor, casein hydrolysate, and soybean hydrolysate.

The cultivation condition is also not specifically limited. The microorganism may be cultivated, for example, under an aerobic condition for about 12 to 48 hours while appropriately controlling pH and temperature within ranges of pH 5 to 8 and temperature of 25 to 40° C.

Proliferated microbial cells may be harvested from a culture liquid, for example, by centrifugation. The cell-free extract is prepared from the harvested microbial cells by using an ordinary method. Namely, the cell-free extract is obtained by disrupting the microbial cells by means of a method such as ultrasonic treatment, Dyno-mill, and French Press, and removing cell debris by centrifugation.

The acid phosphatase is purified from the cell-free extract by using an adequate combination of techniques usually used for enzyme purification such as ammonium sulfate fractionation, ion exchange chromatography, hydrophobic chromatography, affinity chromatography, gel filtration chromatography, and isoelectric purification. As for the precipitation, it is not necessarily indispensable to completely purify the acid phosphatase. It is sufficient to achieve removal of contaminants such as an enzyme which participates in degradation of nucleoside as the substrate.

2. Preparation of a Gene Encoding the Acid Phosphatase

A DNA fragment, which contains a structural gene coding for the protein having the acid phosphatase activity, can be cloned starting from, for example, cells of the microorganism having the enzyme activity. The cloning method includes, for example, a method in which a chromosomal gene expression library is screened by using the enzyme activity as an index, a method in which an antibody against the protein is prepared to screen a chromosomal gene expression library, and a method in which an amino acid sequence such as an N-terminal sequence of the purified protein is analyzed, on the basis of which a probe is prepared to screen a gene library.

Specifically, the gene coding for the acid phosphatase of *Morganella morganii, Escherichia blattae, Providencia stuartii, Enterobacter aerogenes, Klebsiella planticola, Serratia ficaria* or *Serratia marcescens* described above can be cloned by preparing a chromosomal gene expression library of each of the microorganisms, and screening the library by using the phosphatase activity as an index.

Namely, a chromosomal gene expression library can be prepared by firstly preparing chromosomal DNA from *Morganella morganii* or *Escherichia blattae*, partially degrading it with an appropriate restriction enzyme, subsequently ligating it with a vector autonomously replicable in *Escherichia coli*, and transforming *Escherichia coli* with the obtained recombinant DNA. A wide variety of restriction enzymes can be used for digesting chromosomal DNA by adjusting the digestion reaction time to adjust the degree of digestion. Any vector may be used for cloning the gene provided that it is autonomously replicable in *Escherichia coli*. It is possible to use, for example, pUC19, pUC118, pHSG298, pBR322, and pBluescript II.

The vector may be ligated with the DNA fragment containing the gene coding for the acid phosphatase to prepare the recombinant DNA by previously digesting the vector with the same restriction enzyme as that used for digesting chromosomal DNA, or with a restriction enzyme which generates a cleaved edge complementary with a cleaved edge of the chromosomal DNA fragment, and ligating it with the DNA fragment by using ligase such as T4 DNA ligase. Any microbial strain may be used as a recipient for the prepared recombinant DNA provided that it is appropriate for replication of the vector. It is possible to use, for example, microbial strains of *Escherichia coli* such as HB101, JM109, and DH5.

Transformants thus obtained are grown on an agar medium to form their colonies. After that, when a reaction solution containing p-nitrophenylphosphoric acid is poured onto a surface of the medium to perform a reaction, then a strain, which has expressed the phosphatase activity, liberates p-nitrophenol and exhibits a yellow color. A transformant, which harbors a DNA fragment containing the gene coding for the objective acid phosphatase, can be selected by performing the reaction described above under an acidic condition, and selecting the transformant by using the color development as an index.

After that, a recombinant DNA is recovered from the selected transformant to analyze the structure of the DNA fragment containing the gene coding for the acid phosphatase ligated with the vector. A nucleotide sequence of the gene coding for the acid phosphatase is shown in SEQ ID NO: 2 in the Sequence Listing in the case of a gene derived from *Morganella morganii* NCIMB 10466, SEQ ID NO: 6 in the Sequence Listing in the case of a gene derived from *Escherichia blattae* JCM 1650, SEQ ID NO: 21 in the Sequence Listing in the case of a gene derived from *Providencia stuartii* ATCC 29851, SEQ ID NO: 23 in the Sequence Listing in the case of a gene derived from *Enterobacter aerogenes* IFO 12010, SEQ ID NO: 25 in the Sequence Listing in the case of a gene derived from *Klebsiella planticola* IFO14939, or SEQ ID NO: 27 in the Sequence Listing in the case of a gene derived from Serratia ficaria IAM 13540.

The deduced amino acid sequences of the acid phosphatases encoded by the above genes are illustrated in SEQ ID NO: 4, 8, 22, 24, 26 and 28. The acid phosphatases encoded by the above genes are preferably used for the present invention. In addition, the acid phosphatase comprising an amino acid sequence which is substantially identical with an amino acid sequence of any one of the acid phosphatases encoded by the above genes is also preferably used for the present invention. The term "substantially identical" means that amino acid sequences of the acid phosphatases may have substitution, deletion, insertion or transition of one or a plurality of amino acid residues without losing an activity to produce nucleoside-5'-phosphate esters from the nucleoside and the phosphate group donor (hereinafter referred to as "transphosphorylation activity"). The mutant enzyme may, for example, have 1 to 25 amino acid residue substitutions, deletions, insertions or transitions with other amino acid residues. Preferably, the mutant has 1 to 20, more preferably 1 to 15 and, most preferably, 1 to 10 amino acid substitutions, deletions, insertions or transitions. Substitutions are preferred. In another embodiment, the DNAs encoding the mutants of SEQ ID NO: 4, 8, 22, 24, 26 or 28 hybridize under stringent conditions with DNAs encoding the amino acid sequences of SEQ ID NO: 4, 8, 22, 24, 26 or 28, respectively. For example, when the DNA encoding the mutant sequence hybridizes with the non-mutated sequence if contacted for 18 hours at 59° C. in an buffered aqueous solution containing 6×SSC, 10 mM $(Na)_3PO_4$, 1 mM EDTA, 0.5% SDS and 50 µg/ml denatured salmon sperm DNA.

3. Preparation of a Gene Encoding a Mutant Acid Phosphatase

The wild type acid phosphatase obtained as described above has phosphomonoesterase activity. This phosphomonoesterase activity may serve as a factor to cause degradation of the product as the reaction time passes in the production of nucleoside-5'-phosphate ester, resulting in decrease in reaction yield. In order to overcome such a circumstance, it is advantageous to cause artificial mutation on the gene coding for the acid phosphatase so that an affinity for a nucleoside is increased.

Further conducting the phosphate transfer reaction with the acid phosphatase at a higher temperature leads to a much more effective production of nucleoside-5'-phosphate because the reaction speed is elevated and the concentration of a phosphate receiver in the reaction solution may be higher. For the purpose it is advantageous to cause artificial mutation on the gene coding for the acid phosphatase so that a temperature stability is increased.

Methods for site-directed mutagenesis for causing the desired mutation in the DNA include, for example, a method using PCR (Higuchi, R., 61, in *PCR Technology*, Erlich, H. A. Eds., Stockton press (1989); Carter, P., *Meth. in Enzymol.*, 154, 382 (1987)), and a method using phage (Kramer, W. and Frits, H. J., *Meth. in Enzymol.*, 154, 350 (1987); Kunkel, T. A. et al., *Meth. in Enzymol.*, 154, 367 (1987)). All of these publications are incorporated herein by reference.

The mutant acid phosphatase having an increased affinity for the nucleoside is exemplified by the acid phosphatase comprising an amino acid sequence which is substantially identical with an amino acid sequence selected from the group consisting of sequences illustrated in SEQ ID NOs: 4, 8, 22, 24, 26 and 28 in the Sequence Listing, and has mutation which increases the affinity for the nucleoside of wild type acid phosphatase. Concretely, the mutant acid phosphatase is exemplified, for the enzyme derived from *Escherichia blattae* JCM 1650, by one in which the 74th glycine residue and/or the 153th isoleucine residue is substituted with another amino acid residue in an amino acid sequence illustrated in SEQ ID NO: 8 in the Sequence Listing. In the Examples described below, a gene coding for mutant acid phosphatase is illustrated as an example in which the 74th glycine residue is substituted with an aspartic acid residue, and the 153th isoleucine residue is substituted with a threonine residue.

Further mutations selected from the group consisting of substitutions of the 63rd leucine residue, the 65th alanine residue, the 66th glutamic acid residue, the 69th aspartic acid residue, the 71st serine residue, the 72nd serine residue, the 85th serine residue, the 92nd alanine residue, the 94th alanine residue, the 116th aspartic acid residue, the 130th serine residue, the 135th threonine residue and/or the 136th glutamic acid residue with another amino acid in SEQ ID NO: 8 in the Sequence Listing further increase the affinity for the nucleoside of the acid phosphatase.

The mutant acid phosphatase having the increased temperature stability is exemplified by the acid phosphatase comprising an amino acid sequence which is substantially identical with an amino acid sequence selected from the group consisting of sequences illustrated in SEQ ID NOs: 4, 8, 22, 24, 26 and 28 in Sequence Listing, and has mutation which increases the temperature stability of wild type acid phosphatase. Concretely, the mutant acid phosphatase is exemplified, for the enzyme derived from *Escherichia blattae* JCM 1650, by one in which the 104th glutamic acid residue and/or the 151th threonine residue is substituted with another amino acid residue in an amino acid sequence illustrated in SEQ ID NO: 8 in the Sequence Listing. In the Examples described below, a gene coding for mutant acid phosphatase is illustrated as an example in which the 104th glutamic acid residue is substituted with an glycine residue, and the 151th threonine residue is substituted with a alanine residue.

Therefore, the nucleotide may be substituted at the specified site of the wild type gene in accordance with the site-directed mutagenesis method described above so that these mutant acid phosphatases are encoded. The mutation to increase the affinity for the nucleoside is desirably a type of mutation by which the activity to produce nucleoside-5'-phosphate ester is not substantially lowered in comparison with wild type acid phosphatase. However, even in the case that the activity to produce nucleoside-5'-phosphate ester is lowered, it will be sufficient if the degree of decrease of phosphomonoesterase activity is larger than that of the activity to produce nucleoside-5'-phosphate ester, with the result that a ratio of phosphomonoesterase activity to the activity to produce nucleoside-5'-phosphate ester of the mutant acid phosphatase is lowered in comparison with the wild type acid phosphatase. As for the degree of increase in the affinity for the nucleoside, the $K_m$ value to the nucleoside in the transphosphorylation reaction is preferably below 100 mM.

The mutation which increases the temperature stability means one which has more residual activity after a temperature treatment as compared to the wild-type acid phosphatase. The degree of the temperature stability increase is preferably the one that does not cause the decrease in an activity with the treatment at pH 7.0, 50° C., 30 minutes.

As illustrated below, the amino acid sequence of the acid phosphatase of *Escherichia blattae* JCM 1650 is highly homologous to that of *Morganella morganii* NCIMB 10466, and the 72th glycine residue, the 102th glutamic acid residue, the 149th threonine residue and the 151 th isoleucine residue in an amino acid sequence illustrated in SEQ ID NO: 4 correspond to the 74th glycine residue, the 104th glutamic acid residue, the 151th threonine residue and the 153th isoleucine residue in an amino acid sequence illustrated in SEQ ID NO: 8 respectively. Further, in addition to *Escherichia blattae* JCM 1650, amino acid sequences of acid phosphatases derived from microorganisms such as *Providencia stuartii* ATCC 29851, *Enterobacter aerogenes* IFO 12010, *Klebsiella planticola* IFO 14939, and *Serratia ficaria* IAM 13450 have high homology with that of *Morganella morganii* NCIMB 10466, and amino acid sequences of these acid phosphatases include amino acids residues each of which corresponds to the 72th glycine residue, the 102th glutamic acid residue, the 149th threonine residue and the 151th isoleucine residue in an amino acid sequence illustrated in SEQ ID NO: 4 respectively. Therefore, genes coding for mutant acid phosphatases derived from these microorganisms may be obtained as described above. The 92th glycine residue, the 122th glutamic acid residue, the 169th threonine residue and the 171th isoleucine residue in the amino acid sequence of the acid phosphatase derived from *Providencia stuartii* ATCC 29851, *Enterobacter aerogenes* IFO 12010 or *Klebsiella planticola* IFO 14939 illustrated in SEQ ID NO: 22, 24 or 26, and the 88th glycine residue, the 118th glutamic acid residue, the 165th threonine residue and the 167th isoleucine residue in the amino acid sequence of the acid phosphatase derived from *Serratia ficaria* IAM 13450 illustrated in SEQ ID NO: 28 respectively correspond to the 72th glycine residue, the 102th glutamic acid residue, the 149th threonine residue and the 151th isoleucine residue in an amino acid sequence illustrated in SEQ ID NO: 4.

The result to compare the amino acid sequences of the above acid phophatase is illustrated in FIG. 12. Based on FIG. 12, it may be determined which amino acid residue of one acid phosphatase corresponds to an amino acid residue in the sequence of another acid phosphatase.

4. Introduction of the Acid Phosphatase Gene Into a Host

A recombinant microorganism for expressing the acid phosphatase activity at a high level may be obtained by introducing the DNA fragment containing the gene coding for the protein having the acid phosphatase activity obtained as described above into cells of a host after recombining the DNA fragment again with an appropriate vector. In such a procedure, the wild type acid phosphatase is expressed by using the gene coding for the wild type acid phosphatase, while the mutant acid phosphatase is expressed by using the gene coding for the mutant acid phosphatase.

The host includes the microbial strains of *Escherichia coli* such as HB101, JM109, and DH5 described above. Other than these strains, all bacteria can be utilized as the host provided that a replication origin of constructed recombinant DNA and the acid phosphatase gene make their functions, the recombinant DNA is replicable, and the acid phosphatase gene is expressible. One of the most preferred hosts is *Escherichia coli* JM109.

The vector for incorporating the gene coding for the acid phosphatase thereinto is not specifically limited provided that it is replicable in the host. When *Escherichia coli* is used as the host, the vector may be exemplified by plasmids autonomously replicable in this bacterium. Suitable plasmids include for example, ColE1 type plasmids, p15A type plasmids, R factor type plasmids, and phage type plasmids. Such plasmids specifically include, for example, pBR322 (Gene, 2, 95 (1977)), pUC19 (Gene, 33, 103 (1985)), pUC119 (*Methods in Enzymology*, 153, 3 (1987)), pACYC184 (*J. Bacteriol.*, 134, 1141 (1978)), and pSC101 (*Proc. Natl. Acad Sci. U.S.A.*, 70, 3240(1973)). These publications are incorporated herein by reference.

When the DNA fragment containing the gene coding for the acid phosphatase contains a promoter which is functional in the host, the DNA fragment may be ligated with the vector as it is. When the DNA fragment does not contain such a promoter, another promoter which works in the host microorganism such as lac, trp, and PL may be ligated at a position upstream from the gene. Even when the DNA fragment contains the promoter, the promoter may be substituted with another promoter in order to efficiently express the gene coding for the acid phosphatase.

There is no special limitation for a method for introducing, into the host, the recombinant DNA constructed by ligating the vector with the DNA fragment containing the gene coding for the acid phosphatase. The recombinant DNA may be introduced into the host by using an ordinary method. When *Escherichia coli* is used as the host, it is possible to use, for example, a calcium chloride method (*J. Mol. Biol.*, 53, 159 (1970)), a method of Hanahan (*J. Mol. Biol.*, 166, 557 (1983)), the SEM method (Gene, 96, 23 (1990)), the method of Chung et al. (*Proc. Natl. Acad. Sci. U.S.A.*, 86, 2172 (1989)), and electroporation (*Nucleic Acids Res.*, 16, 6127 (1988)). These publications are incorporated herein by reference.

The acid phosphatase gene may be inserted into the autonomously replicable vector DNA, which may be introduced into the host so that it is harbored by the host as extrachromosomal DNA as described above. Alternatively, the acid phosphatase gene may be incorporated into chromosome of the host microorganism in accordance with a method which uses transduction, transposon (*Biotechnol*, 1, 417 (1983)), Mu phage (Japanese Patent Laid-open No. 2-109985), or homologous recombination (*Experiments in Molecular Genetics*, Cold Spring Harbor Lab. (1972)). These publications are incorporated herein by reference.

5. Expression of the Acid Phosphatase Gene by the Recombinant Microorganism

The transformant obtained as described above, into which the recombinant DNA containing the gene coding for the acid phosphatase has been introduced, is capable of expressing the acid phosphatase activity at a high level in its cells by cultivating it in an appropriate medium containing a carbon source, a nitrogen source, inorganic ions, and optionally an organic nutrient source. The carbon source to be adequately used includes, for example, carbohydrates such as glucose, alcohols such as glycerol, and organic acids. The nitrogen source to be used includes, for example, ammonia gas, aqueous ammonia, and ammonium salts. The inorganic ions to be adequately used if necessary include, for example, magnesium ion, phosphate ion, potassium ion, iron ion, and manganese ion. The organic nutrient source to be adequately used includes, for example, vitamins and amino acids as well as those containing them such as yeast extract, peptone, meat extract, corn steep liquor, casein hydrolysate, and soybean hydrolysate. The amount of expression of the acid phosphatase activity may be increased by adding, to the medium, an expression-inducing agent depending on a promoter such as IPTG (isopropyl- -D-thiogalactopyranoside).

The cultivation condition is also not specifically limited. The cultivation may be performed, for example, under an aerobic condition for about 12 to 48 hours while appropriately controlling pH and temperature within ranges of pH 5 to 8 and of 25 to 40° C. respectively.

Following cultivation, the microbial cells are harvested from the culture, and a cell-free extract is obtained by cell disruption, from which the acid phosphatase can be purified. The purification is performed by using an appropriate combination of techniques usually used for enzyme purification such as those described in the aforementioned Section (1). As for the purification, it is not necessary to completely purify the acid phosphatase. It is sufficient to remove contaminants such as enzymes which may degrade the nucleoside substrate.

6. Production of Nucleoside-5'-Phosphate Esters

Nucleoside-5'-phosphate esters may be produced in a reaction mixture by allowing the acid phosphatase obtained as described in the Section (1), or the wild type acid phosphatase or the mutant acid phosphatase obtained by expressing the gene in a large amount in accordance with the genetic engineering technique as described in the Section (5) to contact and cause the reaction of the nucleoside with a phosphate group donor selected from the group consisting of polyphosphoric acid or a salt thereof, phenylphosphonic acid or a salt thereof, acetylphosphoric acid or a salt thereof, and carbamyl phosphate or a salt thereof. In order to achieve a high productivity in this reaction, it is highly desirable to adjust the pH of the reaction solution to be in the weakly acidic range of 3.0 to 5.5.

When the gene coding for the acid phosphatase is expressed in a large amount by means of the genetic engineering technique, especially when the gene coding for the mutant acid phosphatase having the increased affinity for the nucleoside is expressed in a large amount, then it is also possible to produce nucleoside-5'-phosphate ester inexpensively and efficiently by using a culture containing microbial cells of the transformant, the microbial cells separated and harvested from the culture, or a product obtained from the microbial cells in accordance with, for example, an immobilizing treatment, an acetone treatment, or a lyophilizing treatment, instead of the purified acid phosphatase.

The nucleosides to be used as the substrate includes, for example, purine nucleosides such as inosine, guanosine, adenosine, xanthosine, purine riboside, 6-methoxypurine riboside, 2,6-diaminopurine riboside, 6-fluoropurine riboside, 6-thiopurine riboside, 2-amino-6-thiopurine riboside, and mercaptoguanosine; and pyrimidine nucleosides such as uridine, cytidine, 5-aminouridine, 5-hydroxyuridine, 5-bromouridine, and 6-azauridine. As a result of the reaction, these natural type nucleosides and nonnatural type nucleosides are specifically phosphorylated at their 5'-positions, and corresponding nucleoside-5'-phosphate esters are produced respectively. For a detailed description of nucleotides, see G. Michael Blackburn and M. J. Gait, Eds., *Nucleic Acids in Chemistry and Biology*, ILR Press, Oxford University Press, 1990, incorporated herein by reference in its entirety.

The nucleoside is desirably added to the reaction solution at a concentration of 1 to 20 g/dl. In the case of use of a nucleoside which is scarcely soluble in water, the reaction yield may be improved by adding boric acid or a surfactant (such as dimethyl sulfoxide).

When the nucleoside is produced by fermentation, the fermentation medium after the fermentation as such can be added to the phosphorylation reaction liquid. When an element decomposing the nucleoside-5'-phosphate ester is included in the medium, a purification step is preferably employed so that this element is removed.

The phosphate group donor used in the present invention is any compound capable of 5'-phosphorylating the nucleoside in the presence of the acid phosphatase. Suitable examples include polyphosphoric acid or a salt thereof including, for example, pyrophosphoric acid, tripolyphosphoric acid, trimetaphosphoric acid, tetrametaphosphoric acid, hexametaphosphoric acid, mixtures thereof, sodium salts thereof, potassium salts thereof, and mixtures of these salts. Also, phenylphosphonic acid or a salt thereof including, for example, disodium phenylphosphate, dipotassium phenylphosphate, O,O-diphenylphosphoric acid anhydride, and mixtures thereof. In addition, carbamyl phosphate or a salt thereof including, for example, disodium carbamyl phosphate, dipotassium carbamyl phosphate, diammonium carbamyl phosphate, dilithium carbamyl phosphate, and mixtures thereof. Further, acetylphosphoric acid or a salt thereof including, for example, lithium potassium acetylphosphate.

The concentration at which the phosphate group donor is used is determined by the concentration of the nucleoside as the phosphate group acceptor. The phosphate group donor is preferably used in an amount which is 1 to 5 times that of the nucleoside.

A preferred result is obtained in the reaction usually at a temperature of 20 to 60 C., preferably 30 to 40° C. at a weakly acidic pH of 3.5 to 6.5, preferably 4.0 to 5.0. The reaction temperature when using the mutant acid phosphatase with an increased temperature stability may be 20 to 70° C., preferably 30 to 60° C. These ranges include all specific values and subrange therebetween, including 25, 35, 40, 45, 50, 55 and 65° C. The reaction may be performed by adopting any one of a stationary method and an agitating method. The reaction time may differ depending on the reaction condition, such as the activity of the enzyme to be used and the substrate concentration, however, it is 1 to 100 hours. This reaction time range includes all specific values and subranges therebetween, including 2, 5, 10, 25, 50 and 75 hours.

The nucleoside-5'-phosphate ester thus produced may be collected and separated from a mixture after completion of the reaction, i.e., isolated, by adopting a method to use a synthetic resin for adsorption, a method to use a precipitating agent, and other ordinary methods for collection and separation.

Having generally described this invention, a further understanding can be obtained by reference to certain specific examples which are provided herein for purposes of illustration only and are not intended to be limiting unless otherwise specified.

EXAMPLES

The transphosphorylation activity was measured under the following condition using inosine as the substrate. The reaction was performed at pH 5.0 at 30° C. for 10 minutes in a reaction solution (1 ml) containing 40 μmol/ml of inosine, 100 μmol/ml of sodium pyrophosphate, 100 μmol/ml of sodium acetate buffer (pH 5.0), and an enzyme. The reaction was stopped by adding 200 μl of 2 N hydrochloric acid. After that, precipitates were removed by centrifugation. Then, 5'-inosinic acid produced by the transphosphorylation reaction was quantitatively measured. The amount of enzyme to produce 1 μmol of 5'-inosinic acid per 1 minute under this standard reaction condition was defined as 1 unit.

The phosphomonoesterase activity was measured under the following condition using 5'-inosinic acid as a substrate. The reaction was performed at 30° C. for 10 minutes in a reaction solution (1 ml) containing 10 μmol/ml of 5'-inosinic acid, 100 μmol/ml of MES/NaOH buffer (pH 6.0), and an enzyme. The reaction was stopped by adding 200 μl of 2 N hydrochloric acid. After that, precipitates were removed by centrifugation. Then, inosine produced by the hydrolytic reaction was quantitatively measured. An amount of enzyme to produce 1 μmol of inosine per 1 minute under this standard reaction condition was defined as 1 unit.

Inosine and 5'-inosinic acid were analyzed under the following condition by means of high-performance liquid chromatography (HPLC).

Column: Cosmosil 5C18-AR (4.6×150 mm) [produced by nacalai tesque];

Mobile phase: 5 mM potassium phosphate buffer (pH 2.8)/methanol=95/5;

Flow rate: 1.0 ml/min;

Temperature: room temperature;

Detection: UV 245 nm.

In the reaction to produce nucleoside-5'-phosphate esters using nucleosides other than inosine as the substrates, as described below, the nucleoside and produced nucleoside-5'-phosphate ester concentrations were determined by HPLC as described above.

Example 1

Purification and Characterization of Acid Phosphatase Derived from *Morganella morganii*

A nutrient medium (pH 7.0, 50 ml) containing 1 g/dl of peptone, 0.5 g/dl of yeast extract, and 1 g/dl of sodium chloride was poured into Sakaguchi flasks (500 ml), which were sterilized at 120° C. for 20 minutes. A slant culture of *Morganella morganii* NCIMB 10466 was inoculated to each of the flasks once with a platinum loop, which was cultivated at 30° C. for 16 hours with shaking. Microbial cells (about 3,000 g), which were harvested from a culture by centrifugation, were suspended in 100 mM potassium phosphate buffer (1 L, pH 7.0). A ultrasonic treatment was performed at 4° C. for 20 minutes to disrupt the microbial cells. The treated suspension was centrifuged to remove the insoluble fraction. Thus, a cell-free extract was prepared.

Ammonium sulfate was added to the cell-free extract so that 30% saturation was achieved. Appeared precipitate was removed by centrifugation, and then ammonium sulfate was further added to supernatant so that 60% saturation was achieved. Appeared precipitate was collected by centrifugation, and it was dissolved in 100 mM potassium phosphate buffer.

This crude enzyme solution was dialyzed four times against 5 L of 100 mM potassium phosphate buffer (pH 7.0), and then it was applied to a DEAE-Toyopeal 650M column (φ4.1×22 cm) equilibrated with 20 mM potassium phosphate buffer (pH 7.0), followed by washing with 800 ml of 20 mM potassium phosphate buffer (pH 7.0). The transphosphorylation activity was found in a fraction which passed through the column, and thus the fraction was recovered.

The fraction was added with ammonium sulfate so that 35% saturation was achieved, which was adsorbed to a Butyl-Toyopeal column (φ3.1×26 cm) equilibrated with 20 mM potassium phosphate buffer (pH 7.0) containing ammonium sulfate at 35% saturation. Elution was performed by using a linear concentration gradient from 35% saturation to 20% saturation in potassium phosphate buffer (pH 7.0).

Active fractions were collected and dialyzed against 1 L of 50 mM potassium phosphate buffer (pH 7.0), and then applied to a hydroxyapatite column (φ5×6.5 cm) equilibrated with 50 mM potassium phosphate buffer (pH 7.0). Elution was performed by using a linear concentration gradient from 50 mM to 300 mM of potassium phosphate buffer (pH 7.0).

Active fractions were collected and concentrated by ultrafiltration. This enzyme solution was applied into a HiLoad TM 16/60 Superdex 200 column (produced by Pharmacia). Elution was performed at a flow rate of 1.0 ml/minute by using 50 mM potassium phosphate buffer containing 100 mM sodium chloride.

In accordance with the procedure as described above, the enzyme exhibiting the transphosphorylation activity was purified from the cell-free extract consequently about 550-fold at a recovery ratio of about 10%. The specific activity and the recovery ratio in this purification process are shown in Table 1. This enzyme sample was homogeneous on SDS-polyacrylamide gel electrophoresis.

TABLE 1

| Step | Total activity (unit) | Total protein (mg) | Specific activity (unit/mg) | Recovery ratio (%) |
| --- | --- | --- | --- | --- |
| 1. Cell-free extract | 597 | 127,200 | 0.005 | 100 |
| 2. Ammonium sulfate fractionation (30 to 60%) | 568 | 122,210 | 0.005 | 95 |
| 3. DEAE-Toyopearl | 517 | 36,498 | 0.014 | 87 |
| 4. Butyl-Toyopearl | 394 | 1,121 | 0.351 | 66 |
| 5. Hydroxyapatite | 112 | 50 | 2.244 | 19 |
| 6. Superdex 200 | 63 | 24 | 2.630 | 10 |

The purified enzyme had the following properties.

(1) Action: A Phosphate group was transferred from a phosphate group donor such as polyphosphoric acid, to a nucleoside, and nucleoside-5'-phosphate ester was produced. Reversely, this enzyme also exhibits an activity to hydrolyze phosphate ester.

(2) Substrate specificity: Phosphate group donors those which serve as the phosphate group donor in the trarsphosphorylation reaction include, for example, pyrophosphoric acid, tripolyphosphoric acid, trimetaphosphoric acid, tetrametaphosphoric acid, hexametaphosphoric acid, disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate. Those which serve as the phosphate group acceptor include, for example, purine riboside, inosine, guanosine, adenosine, xanthosine, uridine, and cytidine. On the other hand, those which undergo the action in the phosphate ester hydrolytic reaction include, for example, inorganic phosphoric acid such as pyrophosphoric acid, tripolyphosphoric acid, trimetaphosphoric acid, tetrametaphosphoric acid, hexametaphosphoric acid; phosphate ester such as disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate; and 5'-nucleotide such as 5'-purine ribotide, 5'-inosinic acid, 5'-guanylic acid, 5'-adenylic acid, 5'-xanthylic acid, 5'-uridylic acid, and 5'-cytidylic acid.

(3) Optimum pH: 5.2 (transphosphorylation reaction), 6.5 (phosphate ester hydrolytic reaction).

(4) pH stability: pH 3.0 to 12.0 (treatment at 30° C. for 60 minutes).

(5) Optimum temperature: about 35° C.

(6) Temperature stability: stable up to 30° C. (treatment at pH 7.0 for 30 minutes).

(7) Effect of the addition of metal ion and inhibitor: this enzyme exhibits no activation phenomenon relevant to its activity by addition of any metal ion. The activity is inhibited by $Ag^{2+}$, $Pb^{2+}$, $Hg^{2+}$, and $Cu^{2+}$. The activity is also inhibited by iodoacetic acid.

(8) Molecular weight: a calculated molecular weight is about 190,000 in accordance with high-performance liquid chromatography (TSKgel G-3000SW, produced by Toyo Soda).

(9) Subunit molecular weight: a calculated subunit molecular weight is about 25,000 in accordance with SDS-polyacrylamide gel electrophoresis.

This enzyme exhibits not only the activity to transfer phosphate group to a nucleoside, but also the activity to reversely hydrolyze a phosphate ester. Moreover, this enzyme exhibits the phosphate ester hydrolytic activity (phosphomonoestrase activity) which is higher than the transphosphorylation activity by not less than 20 times. Other properties are well coincident with those of a known acid phosphatase produced by a bacterium belonging to the genus Morganella (*Microbiology*, 140, 1341–1350 (1994)). Accordingly, it has been clarified that this enzyme is an acid phosphatase.

Sodium pyrophosphate (10 g/dl) and inosine (2 g/dl) were dissolved in sodium acetate buffers each having pH of 5.5, 5.0, 4.5, 4.0, and 3.5, to which the enzyme sample described above was added so that a concentration of 50 units/dl was obtained. The reaction mixture was incubated at 30° C. for 6 hours while maintaining each pH, and the amount of produced 5'-inosinic acid was measured along with passage of time. Produced inosinic acid contained only 5'-inosinic acid. Production of 2'-inosinic acid and 3'-inosinic acid by-products was not observed at all. The result is shown in FIG. 1. The velocity of 5'-inosinic acid production was maximum at pH 5.0. However, the maximum accumulated amount of 5'-inosinic acid was higher at lower pH. The reaction condition at pH 4.0 was most efficient for production of 5'-inosinic acid, in which 5'-inosinic acid was produced and accumulated in an amount of 2.60 g/dl by performing the reaction for 3 hours.

Example 2

Phosphorylation Reaction of Various Nucleosides by Acid Phosphatase Sample Derived from *Morganella morganii*

Sodium pyrophosphate (10 g/dl) and inosine, guanosine, uridine, or cytidine (2 g/dl) as a phosphate group acceptor were dissolved in sodium acetate buffer (pH 4.0), to which the enzyme sample prepared in Example 1 was added so that its concentration was 50 units/dl. The reaction mixture was incubated at 30° C. for 3 hours while maintaining pH at 4.0. The amount of nucleoside-5'-ester produced by the reaction is shown in Table 2.

Produced nucleotide contained only nucleoside-5'-ester. Production of nucleoside-2'-ester and nucleoside-3'-ester by-products was not observed at all.

TABLE 2

| Nucleoside | Product | Amount Produced (g/dl) |
|---|---|---|
| Inosine | 5'-inosinic acid | 2.60 |
| Guanosine | 5'-guanylic acid | 1.90 |
| Uridine | 5'-uridylic acid | 1.30 |
| Cytidine | 5'-cytidylic acid | 0.98 |

Example 3

Production of 5'-Inosinic acid from Various Phosphate Compounds as Phosphate Group Donors by Acid Phosphatase Sample Derived from *Morganella morganii*

Inosine (2 g/dl) and sodium tripolyphosphate, sodium polyphosphate (trade name: Polygon P, produced by Chiyoda Chemical), disodium phenylphosphate, or disodium carbamyl phosphate (10 g/dl) as a phosphate group donor were dissolved in sodium acetate buffer (pH 4.0), to which the enzyme sample prepared in Example 1 was added so that its concentration was 50 units/dl. The reaction mixture was incubated at 30° C. for 3 hours while maintaining pH at 4.0. The amount of 5'-inosinic acid produced by the reaction is shown in Table 3.

5'-Inosinic acid was efficiently produced and accumulated by using any of the phosphate group donors. However, the accumulated amount of 5'-inosinic acid was the highest when sodium polyphosphate was used as the phosphate group donor.

TABLE 3

| Phosphate group donor | Produced 5'-inosinic acid (g/dl) |
|---|---|
| Sodium tripolyphosphate | 2.10 |
| Sodium polyphosphate | 2.72 |
| Disodium phenylphosphate | 2.33 |
| Disodium carbamyl phosphate | 2.54 |

Example 4

Purification and Characterization of Acid Phosphatase Derived from *Escherichia blattae*

A nutrient medium (pH 7.0, 50 ml) containing 1 g/dl of peptone, 0.5 g/dl of yeast extract, and 1 g/dl of sodium chloride was poured into Sakaguchi flasks (500 ml), which was sterilized at 120° C. for 20 minutes. A slant culture of *Escherichia blattae* JCM 1650 was inoculated to each of the flasks once with a platinum loop, which was cultivated at 30° C. for 16 hours with shaking. Microbial cells were harvested from a culture by centrifugation. The microbial cells (about 3,300 g) were suspended in 100 mM potassium phosphate buffer (1 L, pH 7.0). A ultrasonic treatment was performed at 4° C. for 20 minutes to disrupt the microbial cells. The treated suspension was centrifuged to remove its insoluble fraction. Thus a cell-free extract was prepared.

Ammonium sulfate was added to the cell-free extract so that 30% saturation was achieved. Appeared precipitate was removed by centrifugation, and then ammonium sulfate was further added to supernatant so that 60% saturation was achieved. Appeared precipitate was recovered by centrifugation, and it was dissolved in 100 mM potassium phosphate buffer.

This crude enzyme solution was dialyzed four times against 5 L of 100 mM potassium phosphate buffer (pH 7.0), and then it was applied to a DEAE-Toyopeal 650M column (φ6.2×35 cm) equilibrated with 20 mM potassium phosphate buffer (pH 7.0), followed by washing with 20 mM potassium phosphate buffer (pH 7.0). The transphosphorylation activity was found in a fraction which passed through the column, and thus the fraction was collected.

The active fraction was added with ammonium sulfate so that 35% saturation was achieved, which was applied to a Butyl-Toyopeal column (φ5.0×22.5 cm) equilibrated with 20 mM potassium phosphate buffer (pH 7.0) containing ammonium sulfate at 35% saturation. Elution was performed by using a linear concentration gradient from 35% saturation to 20% saturation in potassium phosphate buffer (pH 7.0).

Active fractions were collected and dialyzed against 1 L of 100 mM potassium phosphate buffer (pH 7.0), followed by being applied to a hydroxyapatite column (φ3.0×7.0 cm) equilibrated with 100 mM potassium phosphate buffer (pH 7.0). Elution was performed by using a linear concentration gradient from 50 mM to 100 mM of potassium phosphate buffer (pH 7.0), and active fractions were collected.

This enzyme solution was dialyzed against 1 L of 10 mM potassium phosphate buffer (pH 6.0), followed by being applied to a CM-Toyopearl column (φ2.0×14.0 cm) equilibrated with 10 mM potassium phosphate buffer (pH 6.0). Elution was performed by using a linear concentration gradient in potassium phosphate buffer (pH 6.0) containing from 0 mM to 300 mM potassium chloride. Active fractions eluted from the column were collected.

In accordance with the procedure as described above, the enzyme exhibiting the transphosphorylation activity was purified from the cell-free extract consequently about 600-fold at a recovery ratio of about 16%. The specific activity and the recovery ratio in this purification process are shown in Table 4. This enzyme sample was homogeneous on SDS-polyacrylamide gel electrophoresis.

TABLE 4

| Step | Total activity (unit) | Total protein (mg) | Specific activity (unit/mg) | Recovery ratio (%) |
|---|---|---|---|---|
| 1. Cell-free extract | 365 | 160,650 | 0.002 | 100 |
| 2. Ammonium sulfate fractionation (30 to 60%) | 340 | 138,895 | 0.002 | 93 |
| 3. DEAE-Toyopearl | 318 | 30,440 | 0.010 | 87 |
| 4. Butyl-Toyopearl | 232 | 661 | 0.347 | 63 |
| 5. Hydroxyapatite | 96 | 96 | 1.000 | 26 |
| 6. CM-Toyopearl | 59 | 43 | 1.365 | 16 |

The purified enzyme had the following properties.

(1) Action: A phosphate group was transferred from a phosphate group donor such as polyphosphoric acid to a nucleoside, and nucleoside-5'-phosphate ester was produced. Reversely, this enzyme also exhibits an activity to hydrolyze phosphate ester.

(2) Substrate specificity: Compounds which serve as the phosphate group donor in the transphosphorylation reaction include, for example, pyrophosphoric acid, tripolyphosphoric acid, trimetaphosphoric acid, tetrametaphosphoric acid, hexametaphosphoric acid, disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate. Those which serve as the phosphate group acceptor include, for example, purine riboside, inosine, guanosine, adenosine, xanthosine, uridine, and cytidine. On the other hand, those which undergo the action in the phosphate ester hydrolytic reaction include, for example, inorganic phosphoric acid such as pyrophosphoric acid, tripolyphosphoric acid, trimetaphosphoric acid, tetrametaphosphoric acid, hexametaphosphoric acid; phosphate ester such as disodium phenylphosphate, dipotassium phenylphosphate, O,O-diphenylphosphoric acid anhydride, disodium carbamyl phosphate, dipotassium carbamyl phosphate, diammonium carbamyl phosphate, and dilithium carbamyl phosphate; and 5'-nucleotide such as 5'-purine ribotide, 5'-inosinic acid, 5'-guanylic acid, 5'-adenylic acid, 5'-xanthylic acid, 5'-uridylic acid, and 5'-cytidylic acid.

(3) Optimum pH: 5.2 (transphosphorylation reaction), 6.5 (phosphate ester hydrolytic reaction).

(4) pH stability: pH 3.5 to 12.0 (treatment at 30° C. for 60 minutes).

(5) Optimum temperature: about 35° C.

(6) Temperature stability: stable up to 40° C. (treatment at pH 7.0 for 30 minutes).

(7) Effect of the addition of metal ion and inhibitor: This enzyme exhibits no activation phenomenon relevant to its activity by addition of any metal ion The activity is inhibited by $Fe^{2+}$, $Ag^{2+}$, $Pb^{2+}$, $Hg^{2+}$, and $Cu^{2+}$. The activity is also inhibited by iodoacetic acid.

(8) Molecular weight: The calculated molecular weight is about 188,000 in accordance with high-performance liquid chromatography (TSKgel G-3000SW, produced by Toyo Soda).

(9) Subunit molecular weight: The calculated subunit molecular weight is about 24,500 in accordance with SDS-polyacrylamide gel electrophoresis.

This enzyme also exhibits not only the activity to transfer phosphate group to a nucleoside, but also the activity to reversely hydrolyze a phosphate ester, in the same manner as the enzyme purified from the cell-free extract of *Morganella morganii* NCIMB 10466. Moreover, this enzyme exhibits the phosphate ester hydrolytic activity (phosphomonoesterase activity) which is higher than the transphosphorylation activity by not less than 30 times. Accordingly, it has been determined that this enzyme is an acid phosphatase.

Figure 2:
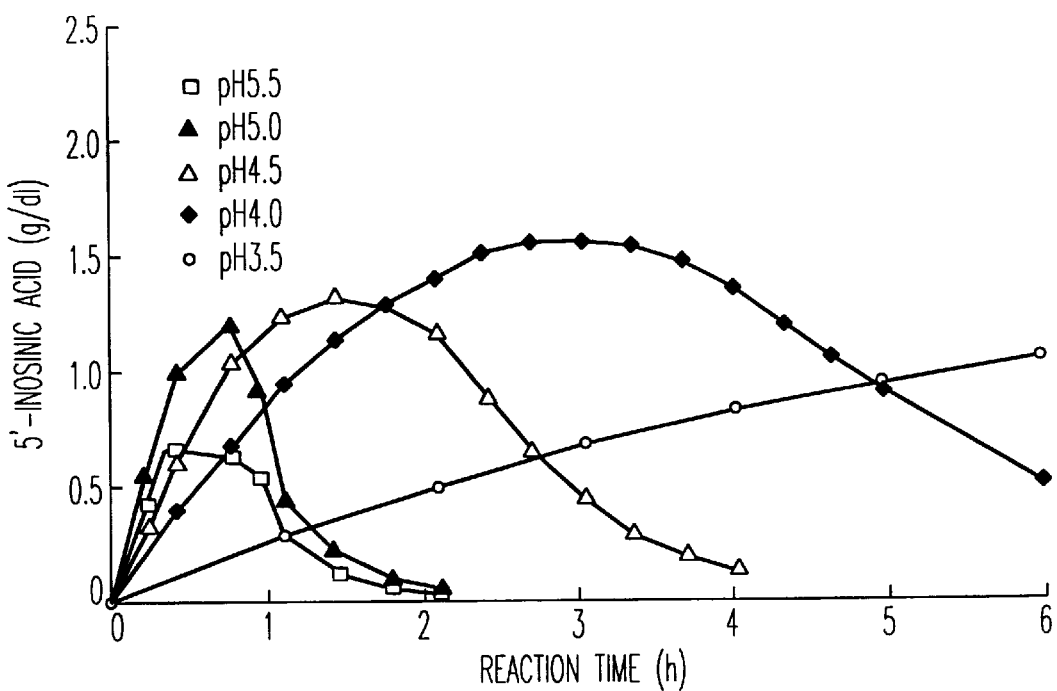
FIG. 2 illustrates the relationship between the reaction pH and the amount of 5'-inosinic acid provided in a reaction performed with the enzyme derived from *Escherichia blattae*.

Sodium pyrophosphate (15 g/dl) and inosine (3 g/dl) were dissolved in sodium acetate buffers each having pH of 5.5, 5.0, 4.5, 4.0, and 3.5, to which the enzyme sample described above was added so that a concentration of 50 units/dl was obtained. The reaction mixture was incubated at 30° C. for 6 hours while maintaining each pH, and the amount of produced 5'-inosinic acid was measured along with passage of time. Produced inosinic acid contained only 5'-inosinic acid. By-production of 2'-inosinic acid and 3'-inosinic acid was not observed at all. The result is shown in FIG. 2. The velocity of 5'-inosinic acid production was maximum at pH 5.0. However, the maximum accumulated amount of 5'-inosinic acid was higher at lower pH. The reaction condition at pH 4.0 was most efficient for production of 5'-inosinic acid. 5'-Inosinic acid was produced and accumulated in an amount of 1.56 g/dl by performing the reaction at 30° C. at pH 4.0 for 3 hours.

Example 5

Phosphorylation Reaction of Various Nucleosides by Acid Phosphatase Sample Derived from *Escherichia blattae*

Sodium pyrophosphate (15 g/dl) and inosine, guanosine, uridine, or cytidine (3 g/dl) were dissolved in sodium acetate buffer (pH 4.0), to which the enzyme sample prepared in Example 4 was added so that its concentration was 50 units/dl. The reaction mixture was incubated at 35° C. for 3 hours while maintaining pH at 4.0. The amount of produced nucleoside-5'-ester is shown in Table 5.

Produced nucleotide contained only nucleoside-5'-ester. By-production of nucleoside-2'-ester and nucleoside-3'-ester was not observed at all.

TABLE 5

| Nucleoside | Product | Amount Produced (g/dl) |
| --- | --- | --- |
| Inosine | 5'-inosinic acid | 1.56 |
| Guanosine | 5'-guanylic acid | 1.05 |
| Uridine | 5'-uridylic acid | 1.87 |
| Cytidine | 5'-cytidylic acid | 1.22 |

Example 6

Production of 5'-Inosinic acid from Various Phosphate Compounds as Phosphate Group Donors by Acid Phosphatase Sample Derived from *Escherichia blattae*

Inosine (2 g/dl) and sodium tripolyphosphate, sodium polyphosphate (trade name: Polygon P, produced by Chiyoda Chemical), disodium phenylphosphate, or disodium carbamyl phosphate (10 g/dl) as a phosphate group donor were dissolved in sodium acetate buffer (pH 4.0), to which the enzyme sample prepared in Example 4 was added so that its concentration was 50 units/dl. The reaction mixture was incubated at 35° C. for 3 hours while maintaining pH at 4.0. The amount of produced 5'-inosinic acid is shown in Table 6.

5'-Inosinic acid was efficiently produced and accumulated by using any of the phosphate group donors. However, the accumulated amount of 5'-inosinic acid was the highest when sodium polyphosphate was used as the phosphate group donor.

TABLE 6

| Phosphate group donor | Produced 5'-inosinic acid (g/dl) |
| --- | --- |
| Sodium tripolyphosphate | 1.20 |
| Sodium polyphosphate | 1.79 |
| Disodium phenylphosphate | 1.50 |
| Disodium carbamyl phosphate | 1.53 |

Example 7

Isolation of Gene Coding for Acid Phosphatase from Chromosome of *Morganella morganii*

(1) Determination of N-terminal Amino Acid Sequence

The acid phosphatase purified from the cell-free extract of *Morganella morganii* NCIMB 10466 in accordance with the method described in Example 1 was adsorbed to DITC membrane (produced by Milligen/Biosearch), and its N-terminal amino acid sequence was determined by using Prosequencer 6625 (produced by Milligen/Biosearch). An N-terminal amino acid sequence comprising 20 residues shown in SEQ ID NO: 1 in the Sequence Listing was determined.

(2) Isolation of DNA Fragment Containing Gene Coding For the Acid Phosphatase

Chromosomal DNA was extracted from cultivated microbial cells of *Morganella morganii* NCIMB 10466 in accordance with a method of Murray and Thomson (*Nucl. Acid Res.*, 4321, 8 (1980)). The chromosomal DNA was partially degraded with restriction enzyme Sau3AI. After that, DNA fragments of 3 to 6 kbp were fractionated by means of sucrose density gradient centrifugation. A plasmid vector pUC118 (produced by Takara Shuzo) was digested with restriction enzyme BamHI, which was ligated with the partially degraded chromosomal DNA fragments. DNA ligation was performed by using DNA ligation kit (produced by Takara Shuzo) in accordance with a designated method. After that, *Escherichia coli* JM109 (produced by Takara Shuzo) was transformed with an obtained DNA mixture in accordance with an ordinary method. Transformants were plated on an L agar medium containing 100 µg/ml of ampicillin, and they were grown to prepare a gene library.

A reaction solution containing 4 mM p-nitrophenylphosphoric acid and 100 mM MES/NaOH buffer (pH 6.5) was poured onto a surface of the agar medium on which the transformants had grown, and the temperature was kept at 30° C. for 15 minutes. Strains which had expressed the phosphatase activity liberated p-nitrophenol and exhibited a yellow color. Accordingly, transformants were selected by using this phenomenon as an index. As a result of screening for a gene expression library comprising about 20,000 strains of transformants, 30 strains of transformants which had expressed the phosphatase activity were obtained.

The transformants (30 strains), which had expressed the phosphatase activity, were subjected to single colony isolation. Single colonies were inoculated to an L-medium (2.5 ml) containing 100 µg/ml of ampicillin, and they were cultivated at 37° C. for 16 hours. Sodium acetate buffer (100 mM, pH 5.0, 50 l) containing inosine (2 g/dl) and sodium pyrophosphate (10 g/dl) was added to microbial cells harvested from culture, and the reaction mixture was incubated at 30° C. for 16 hours. Production of 5'-inosinic acid was detected by HPLC analysis to select microbial strains having the transphosphorylation activity. As a result, we succeeded in obtaining 5 strains of transformants which exhibited the transphosphorylation activity and which were assumed to harbor a DNA fragment containing the objective acid phosphatase gene were obtained.

Example 8

Determination of Nucleotide Sequence of Acid Phosphatase Gene Derived from *Morganella morganii* NCIMB 10466

Figure 3:
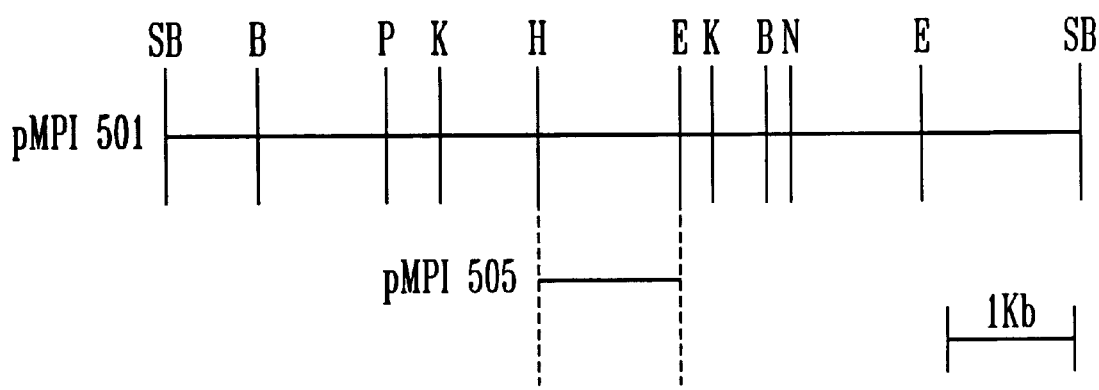
FIG. 3 illustrates a restriction enzyme map of a chromosomal DNA fragment of *Morganella morganii* containing a gene coding for an acid phosphatase.

The inserted DNA fragment was analyzed by preparing a plasmid in accordance with an alkaline lysis method (*Molecular Cloning* 2nd edition (J. Sambrook, E. F. Fritsch and T. Maniatis, Cold Spring Harbour Laboratory Press, pl. 25 (1989)) from one strain of the transformants which were assumed to harbor the DNA fragment containing the acid phosphatase gene derived from *Morganella morganii* NCIMB 10466 obtained in Example 7. This plasmid was designated as pMPI501. FIG. 3 shows a determined restriction enzyme map of the inserted DNA fragment.

The region of the acid phosphatase gene was further specified by subcloning. As a result, it was suggested that this acid phosphatase gene was contained in a fragment having a size of 1.2 Kbp excised by restriction enzymes HindIII and EcoRI. Thus in order to determine the nucleotide sequence, plasmid DNA was constructed in which the fragment of 1.2 kbp was ligated with pUC118 having been digested with HindIII and EcoRI. *Escherichia coli* JM109 (produced by Takara Shuzo) was transformed with this plasmid DNA designated as pMPI505 in accordance with an ordinary method, which was plated on an L agar medium containing 100 µg/ml of ampicillin to obtain a transformant.

The plasmid was extracted in accordance with the alkaline lysis method from the transformant of *Escherichia coli* JM109 (produced by Takara Shuzo) harboring pMPI505 to determine the nucleotide sequence. The nucleotide sequence was determined in accordance with the method of Sanger (*J. Mol. Biol*, 143, 161 (1980)) by using Taq DyeDeoxy Terminator Cycle Sequencing Kit (produced by Applied Biochemical). A nucleotide sequence of a determined open reading frame is shown in SEQ ID NO: 2 in the Sequence Listing. An amino acid sequence of the protein deduced from the nucleotide sequence is shown in SEQ ID NO: 3 in the Sequence Listing. A partial sequence, which was completely coincident with the N-terminal amino acid sequence of the purified enzyme, was found in the amino acid sequence. The N-terminal of the purified enzyme starts from the 21th alanine residue of the sequence shown in SEQ ID NO: 3. Accordingly, it is assumed that the amino acid sequence shown in SEQ ID NO: 3 is that of a precursor protein, and that a peptide comprising a range from the 1st methionine residue to the 20th alanine residue is eliminated after translation. An amino acid sequence of a mature protein thus deduced is shown in SEQ ID NO: 4 in the Sequence Listing. A molecular weight of the mature protein estimated from the amino acid sequence is calculated to be 24.9 kilodaltons, which is well coincident with the result of SDS-PAGE for the purified enzyme. According to the results described above, and because of the fact that the transformant harboring the plasmid containing this fragment exhibited the transphosphorylation activity, it was identified that this open reading frame was the region coding for the objective acid phosphatase.

The nucleotide sequence and the amino acid sequence were respectively compared with known sequences for homology. Data bases of EMBL and SWISS-PROT were used. As a result, it has been revealed that the nucleotide sequence shown in SEQ ID NO: 2 in the Sequence Listing is coincident with a nucleotide sequence of a known acid phosphatase gene derived from *Morganella morganii* (Thaller, M. C. et al., *Microbiology*, 140, 1341 (1994)) except that 54th G is A, 72th G is A, 276th T is G, 378th T is C, 420th G is T, 525th C is G, 529th C is T, and 531th G is A in the latter, and that the amino acid sequence shown in SEQ ID NO: 4 in the Sequence Listing is the same as that of the acid phosphatase gene derived from *Morganella morganii*. Namely, the gene, which codes for the protein comprising the amino acid sequence shown in SEQ ID NO: 4 in the Sequence Listing, is the acid phosphatase gene of *Morganella morganii* NCIMB 10466.

A precursor protein comprises 249 amino acids, and a molecular weight of the protein deduced from its sequence is 27.0 kilodaltons.

The strain of *Escherichia coli* JM109 transformed by a plasmid pMPI505, has been designated as AJ13143, which has been internationally deposited on Feb. 23, 1996 at the National Institute of Bioscience and Human Technology of Agency of Industrial Science and Technology (postal code: 305, 1–3, Higashi 1-chome, Tsukuba-shi,Ibaraki-ken, Japan) under the provisions of the Budapest Treaty, and awarded a deposition number of FERM BP-5422.

Example 9

Amplification of Activity by Expressing Gene of Acid Phosphatase Derived from *Morganella morganii* NCIMB 10466

*Escherichia coli* JM109/pMPI505 constructed in Example 8 was inoculated to an L-medium (50 ml) containing 100 µg/ml of ampicillin and 1 mM of IPTG, and it was cultivated at 37° C. for 16 hours. Microbial cells were harvested from its culture by centrifugation, and they were washed once with physiological saline. The microbial cells were suspended in 100 mM potassium phosphate buffer (5 ml, pH 7.2), and they were disrupted by means of a ultrasonic treatment performed at 40° C. for 20 minutes. The treated solution was centrifuged to remove an insoluble fraction, and thus a cell-free extract was prepared.

The transphosphorylation activity of the obtained cell-free extract was measured while using controls of cell-free extracts prepared from the wild type strain of *Morganella morganii* and *Escherichia coli* JM109 transformed with the plasmid pUC118 in the same manner as described above. The result is shown in Table 7. The transphosphorylation activity was not detected in *Escherichia coli* JM109/pUC118. The transphosphorylation activity was also low in the wild type strain of *Morganella morganii*. On the other hand, *Escherichia coli* JM109/pMPI505 exhibited a high transphosphorylation activity which was 150 times as high as that of the wild type strain of *Morganella morganii* in specific activity. According to the result, it has been demonstrated that the introduced DNA fragment allows *Escherichia coli* to express the acid phosphatase at a high level.

TABLE 7

| Microbial strain | Transphosphorylation Activity (units/mg) |
| --- | --- |
| *Morganella morganii* NCIMB 10466 | 0.008 |
| *Escherichia coli* JM109/pUC118 | not detected |
| *Escherichia coli* JM109/pMPI5O5 | 1.250 |

Example 10

Figure 4:
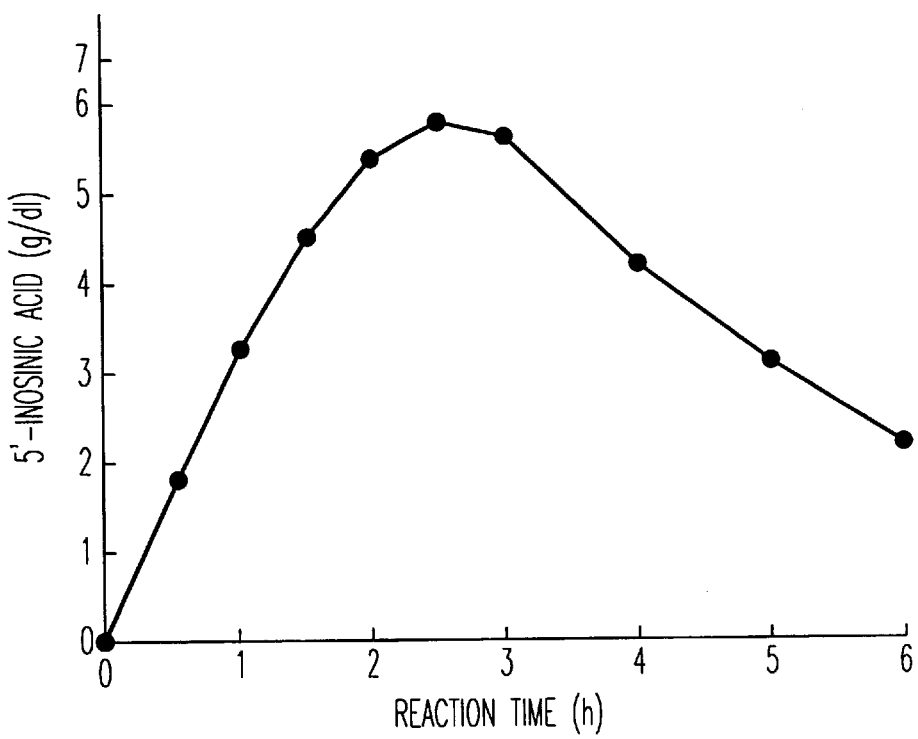
FIG. 4 illustrates the amount of 5'-inosinic acid produced in a reaction performed with a strain harboring an acid phosphatase gene derived from *Morganella morganii*.

FIG. 4 illustrates the amount of 5'-inosinic acid produced in a reaction performed with a strain harboring an acid phosphatase gene derived from *Morganella morganii*.

Example 11

Isolation of Gene Coding for Acid Phosphatase from Chromosome of *Escherichia blattae*

(1) Determination of the N-terminal Amino Acid Sequence

The acid phosphatase purified from the cell-free extract of *Escherichia blattae* JCM 1650 was adsorbed to DITC membrane (produced by Milligen/Biosearch), and its N-terminal amino acid sequence was determined by using Prosequencer 6625 (produced by Milligen/Biosearch). An N-terminal amino acid sequence comprising 15 residues shown in SEQ ID NO: 8 in the Sequence Listing was determined.

(2) Isolation of DNA Fragment Containing Gene Coding For Acid Phosphatase

Chromosomal DNA was extracted from cultivated cells of *Escherichia blattae* JCM 1650 in accordance with a method of Murray and Thomson (*Nucl. Acid Res.*, 4321, 8 (1980)). The chromosomal DNA was partially degraded with Sau3AI. After that, DNA fragments of 3 to 6 kbp were fractionated by means of sucrose density gradient centrifugation. A plasmid vector pUC118 (produced by Takara Shuzo) was digested with BamHI, which was ligated with the partially degraded chromosomal DNA fragments. DNA ligation was performed by using DNA ligation kit (produced by Takara Shuzo) in accordance with a designated method. After that, *Escherichia coli* JM109 (produced by Takara Shuzo) was transformed with an obtained DNA mixture in accordance with an ordinary method. Transformants were plated on an L agar medium containing 100 µg/ml of ampicillin, and they were grown to prepare a gene library.

A reaction solution containing 4 mM p-nitrophenylphosphoric acid and 100 mM MES/NaOH buffer (pH 6.5) was poured onto a surface of the agar medium on which the transformants had grown, and the temperature was kept at 30° C. for 15 minutes. Strains which had expressed the phosphatase activity liberated p-nitrophenol and exhibited a yellow color. Accordingly, transformants were selected by using this phenomenon as an index. As a result of screening for a chromosomal gene expression library comprising about 8,000 strains of transformants, 14 strains of transformants which had expressed the phosphatase activity were obtained.

The transformants (14 strains), which had expressed the phosphatase activity, were subjected to single colony isolation. Single colonies were inoculated to an L-medium (2.5 ml) containing 100 µg/ml of ampicillin, and they were cultivated at 37° C. for 16 hours. Sodium acetate buffer (100 mM, pH 5.0, 50 l) containing inosine (2 g/dl) and sodium pyrophosphate (10 g/dl) was added to microbial cells harvested from culture liquids to perform the reaction at 30° C. for 16 hours. Production of 5'-inosinic acid was detected by HPLC analysis to select strains having the transphosphorylation activity. As a result, 3 strains of transformants which exhibited the transphosphorylation activity and which were assumed to harbor a DNA fragment containing the objective acid phosphatase gene were obtained.

Example 12

Determination of Nucleotide Sequence of Acid Phosphatase Gene Derived from *Escherichia blattae* JCM 1650

Figure 5:
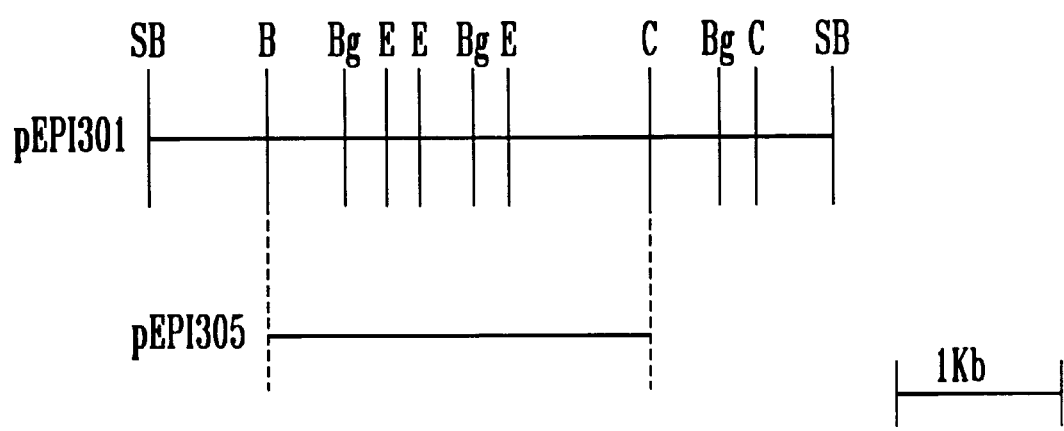
FIG. 5 illustrates a restriction enzyme map of a chromosomal DNA fragment of *Escherichia blattae* containing a gene coding for an acid phosphatase.

The inserted DNA fragment was analyzed by extracting a plasmid in accordance with the alkaline lysis method from one strain of the transformants which were assumed to harbor the DNA fragment containing the acid phosphatase gene derived from *Escherichia blattae* JCM 1650 obtained in Example 11. This plasmid was designated as pEPI301. FIG. 5 shows the determined restriction enzyme map of the inserted DNA fragment.

The region of the acid phosphatase gene was further specified by subcloning. As a result, it was suggested that this acid phosphatase gene was included in a fragment having a size of 2.4 Kbp excised by restriction enzymes ClaI and BamHI. Thus in order to determine the nucleotide sequence, plasmid DNA was constructed in which the fragment was ligated with pBluescript KS(+) (produced by Stratagene) having been digested with ClaI and BamHI. *Escherichia coli* JM109 (produced by Takara Shuzo) was transformed with the plasmid DNA designated as pEPI305 in accordance with an ordinary method, which was plated on an L agar medium containing 100 μg/ml of ampicillin to obtain a transformant.

The plasmid was extracted in accordance with the alkaline lysis method from the transformant of *Escherichia coli* JM109 (produced by Takara Shuzo) harboring pEPI305 to determine the nucleotide sequence. A nucleotide sequence of a determined open reading frame is shown in SEQ ID NO: 6 in the Sequence Listing. An amino acid sequence of the protein deduced from the nucleotide sequence is shown in SEQ ID NO: 7 in the Sequence Listing. A partial sequence, which was completely coincident with the N-terminal amino acid sequence of the purified enzyme, was found in the amino acid sequence. The N-terminal of the purified enzyme starts from the 19th leucine residue of the sequence shown in SEQ ID NO: 7. Accordingly, it is assumed that the amino acid sequence shown in SEQ ID NO: 7 is that of a precursor protein and that a peptide comprising a range from the 1st methionine residue to the 18th alanine residue is eliminated after translation. An amino acid sequence of a mature protein thus deduced is shown in SEQ ID NO: 8 in the Sequence Listing. Accordingly, an estimated molecular weight of the mature protein is calculated to be 25.1 kilodaltons, which is well coincident with the result of SDS-PAGE for the purified enzyme. According to the results described above, and because of the fact that the transformant harboring the plasmid containing this fragment exhibited the transphosphorylation activity, it was identified that this open reading frame was the region coding for the desired acid phosphatase.

Namely, the gene, which codes for the protein comprising the amino acid sequence shown in SEQ ID NO: 8 in the Sequence Listing, is the acid phosphatase gene of *Escherichia coli* JCM 1650.

The nucleotide sequence and the amino acid sequence were respectively compared with known sequences for homology. Data bases of EMBL and SWISS-PROT were used. As a result, it has been revealed that the protein shown in SEQ ID NO: 8 and DNA coding for it are novel. A precursor protein encoded by this gene comprises 249 amino acids, and a molecular weight of the protein deduced from its sequence is 27.0 kilodaltons.

The amino acid sequence was compared with known sequences respectively for homology. As a result, this protein exhibited a high degree of homology with the acid phosphatase of *Providencia stuartii* (77.1%) with the acid phosphatase of *Morganella morganii* in Example 8 (77.1%), and with acid phosphatase of Salmonella typhimurium (44.3%).

The strain of *Escherichia coli* JM109 transformed by a plasmid pEPI305, has been designated as AJ13144, which has been internationally deposited on Feb. 23, 1996 in National Institute of Bioscience and Human Technology of Agency of Industrial Science and Technology (postal code: 305, 1-3, Higashi 1-chome, Tsukuba-shi, Ibaraki-ken, Japan) under the provisions of the Budapest Treaty, and awarded a deposition number of FERM BP-5423.

Example 13

Amplification of Activity by Expressing Gene of Acid Phosphatase Derived from *Escherichia blattae* JCM 1650

*Escherichia coli* JM109/pEPI305 constructed in Example 12 was inoculated to an L medium (50 ml) containing 100 μg/ml of ampicillin and 1 mM of IPTG, and it was cultivated at 37° C. for 16 hours. Microbial cells were harvested from its culture by centrifugation, and they were washed once with physiological saline. The microbial cells were suspended in 100 mM potassium phosphate buffer (5 ml, pH 7.2), and were disrupted by means of a ultrasonic treatment performed at 4° C. for 20 minutes. The treated solution was centrifuged to remove an insoluble fraction, and thus a cell-free extract was prepared.

The transphosphorylation activity of the obtained cell-free extract was measured while using controls of cell-free extracts prepared from the wild type strain of *Escherichia blattae* and *Escherichia coli* JM109 transformed with the plasmid pBluescript KS(+) in the same manner as described above. The result is shown in Table 8. The transphosphorylation activity was not detected in *Escherichia coli* JM109/pBluescript KS(+). The transphosphorylation activity was also low in the wild type strain of *Escherichia blattae*. On the other hand, *Escherichia coli* JM109/pEPI305 exhibited a high transphosphorylation activity which was 120 times as high as that of the wild type strain of *Escherichia blattae* in specific activity. According to the result, it has been demonstrated that the introduced DNA fragment allows *Escherichia coli* to express the acid phosphatase at a high level.

TABLE 8

| Microbial strain | Transphosphorylation Activity (units/mg) |
| --- | --- |
| *Escherichia blattae* JCM 1650 | 0.002 |
| *Escherichia coli* JM109/pBluescript KS(+) | not detected |
| *Escherichia coli* JM109/pEPI3O5 | 0.264 |

Example 14

Production of 5'-Inosinic Acid from Inosine by Using Strain Harboring Acid Phosphatase Gene Derived from *Escherichia blattae* JCM 1650

Figure 6:
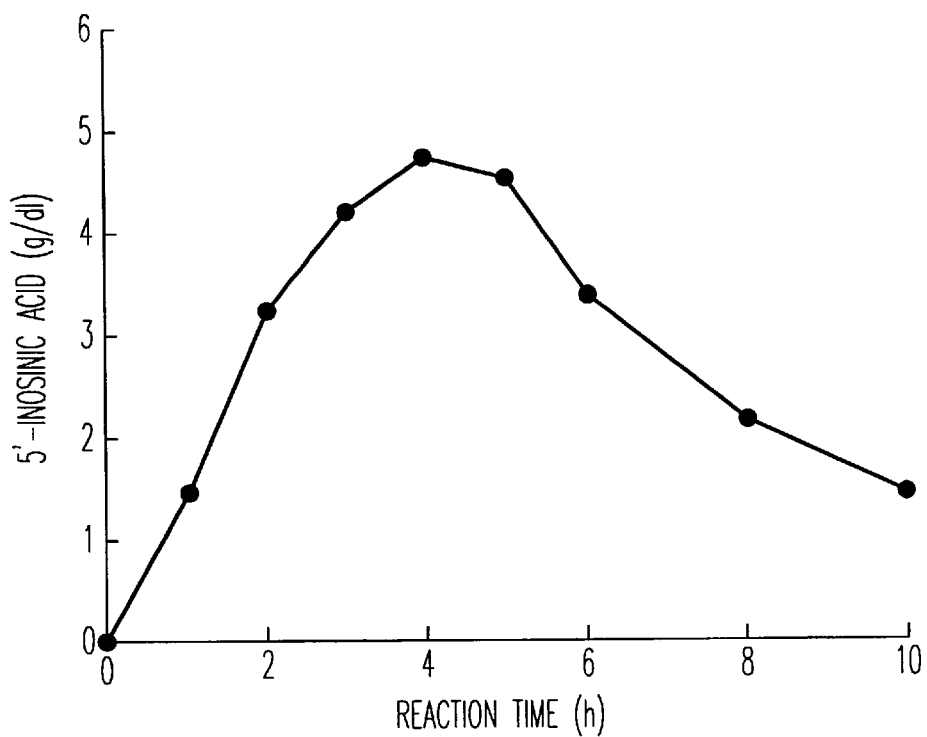
FIG. 6 illustrates a diagram showing the amount of 5'-inosinic acid provided in a reaction performed with a strain harboring the acid phosphatase gene derived from *Escherichia blattae*.

Sodium pyrophosphate (12 g/dl) and inosine (6 g/dl) were dissolved in 100 mM sodium acetate buffer (pH 4.0), to which the microbial cells of *Escherichia coli* JM109/pEPI305 described above were added to give a cell concentration of 200 mg/dl as converted into a dry weight of the microbial cells. The reaction mixture was incubated at 35° C. for 10 hours while maintaining pH at 4.0, and the amount of produced 5'-inosinic acid was measured along with passage of time. Produced inosinic acid contained only 5'-inosinic acid. By-production of 2'-inosinic acid and 3'-inosinic acid was not observed at all. The result is shown in FIG. 6. 5'-Inosinic acid was produced and accumulated extremely efficiently in a short period of time in the reaction to produce 5'-inosinic acid from pyrophosphate and inosine by using this microorganism.

Example 15

Preparation of a Gene Encoding An Acid Phosphatase with Lowered Phosphomonoesterase activity As described in Examples 13 and 14, the strain harboring the acid phosphatase gene derived from *Escherichia blattae* expresses a considerable amount of the acid phosphatase, and 5'-inosinic acid is produced and accumulated extremely efficiently in a short period of time in the reaction to produce 5'-inosinic acid from pyrophosphate and inosine by using this microorganism. However, it has been revealed that the accumulated amount of 5'-inosinic acid does not exceed a certain degree because produced 5'-inosinic acid undergoes degradation by the phosphomonoesterase activity possessed by the acid phosphatase itself. Thus the enzyme was intended to be improved by introducing mutation into the acid phosphatase gene derived from *Escherichia blattae* cloned in Example 11, in accordance with the site-directed mutagenesis method by using PCR.

Oligonucleotides MUT300, MUT310, and MUT320 shown in SEQ ID NO: 9, 10, and 11 in the Sequence Listing were synthesized respectively in accordance with the phosphoamidite method by using a DNA synthesizer (Model 394 produced by Applied Biosystems).

The plasmid pEPI305 (1 ng) as a template prepared in Example 12, M13 primer RV (produced by Takam Shuzo) and MUT310 oligonucleotide (each 2.5 µmol) as primers, and Taq DNA polymerase (2.5 units, produced by Takara Shuzo) were added to 100 mM Tris-HCl buffer (pH 8.3, 100 µl) containing dATP, dCTP, dGTP, dTTP (each 200 µM), potassium chloride (50 mM), and magnesium chloride (1.5 mM) to perform a PCR reaction in which a cycle comprising periods of 30 seconds at 94° C., 2 minutes at 55° C., and 3 minutes at 72° C. was repeated 25 times. The PCR reaction was performed by using Thermal Cycler PJ2000 type (produced by Takara Shuzo). Also, a PCR reaction was performed in the same manner as described above by using plasmid pEPI305 (1 ng) as a temperate, and M13 primer M3 (produced by Takara Shuzo) and MUT300 oligonucleotide (each 2.5 µmol) as primers. Each of the reaction solutions was purified by gel filtration to remove the primers by using Microspin column S-400 (produced by Pharmacia).

Each of the PCR reaction products (1 µl) was added to 100 mM Tris-HCl buffer (pH 8.3, 95 µl) containing dATP, dCTP, dGTP, dTTP (each 200 µM), potassium chloride (50 mM), and magnesium chloride (1.5 mM), and it was heated at 94° C. for 10 minutes, followed by cooling to 37° C. over 60 minutes. After that, the temperature was kept at 37° C. for 15 minutes to form a heteroduplex. Taq DNA polymerase (2.5 units) was added thereto to perform a reaction at 72° C. for 3 minutes so that the heteroduplex was completed. After that, M13 primer RV and M13 primer M3 (each 2.5 µmol) were added to this reaction solution to perform a PCR reaction in which a cycle comprising periods of 30 seconds at 94° C., 2 minutes at 55° C., and 3 minutes at 72° C. was repeated 10 times.

A product of the second PCR reaction was digested with ClaI and BamHI followed by phenol/chloroform extraction and ethanol precipitation. This DNA fragment was ligated with pBluescript KS(+) having been digested with ClaI and BamHI. *Escherichia coli* JM109 (produced by Takara Shuzo) was transformed with obtained plasmid DNA in accordance with an ordinary method, which was plated on an L agar medium containing 100 µg/ml of ampicillin to obtain a transformant.

The plasmid was extracted from the transformant in accordance with the alkaline lysis method to determine its nucleotide sequence, confirming that the desired nucleotide was substituted. Thus a mutant gene coding for a mutant phosphatase was prepared in which the 74th glycine residue (GGG) of the mature protein was substituted with an aspartic acid residue (G*A*T). The plasmid containing this mutant gene was designated as pEPI310.

A mutant gene coding for a mutant phosphatase was prepared in which the 153th isoleucine residue (ATC) of the mature protein was substituted with a threonine residue (A*CC), in accordance with the same procedure as described above by using pEPI305 as a template, and MUT300 and MUT320 oligonucleotides as primers. The plasmid containing this mutant gene was designated as pEPI320. Further, a mutant gene coding for a mutant phosphatase was prepared in which the 74th glycine residue (GGG) of the mature protein was substituted with an aspartic acid residue (G*A*T), and the 153th isoleucine residue (ATC) of the mature protein was substituted with a threonine residue (A*CC), in accordance with the same procedure as described above by using pEPI310 as a template, and MUT300 and MUT320 oligonucleotides as primers. The plasmid containing this mutant gene was designated as pEPI330.

*Escherichia coli* JM109/pEPI310, *Escherichia coli* JM109/pEPI320, and *Escherichia coli* JM109/pEPI330 into which the plasmids containing the respective mutant acid phosphatase genes had been introduced, and *Escherichia coli* JM109/pEPI305 into which the plasmid containing the wild type acid phosphatase gene had been introduced were inoculated to an L medium (50 ml) containing 100 µg/ml of ampicillin and 1 mM of IPTG, and they were cultivated at 37 C. for 16 hours. Microbial cells were harvested from their culture, and they were washed once with physiological saline. The microbial cells were suspended in 100 mM potassium phosphate buffer (5 ml, pH 7.0), and they were disrupted by means of a ultrasonic treatment performed at 4 C. for 20 minutes. The treated solutions were centrifuged to remove insoluble fractions, and thus cell-free extracts were prepared. Phosphomonoesterase activities and transphosphorylation acitivities of the obtained cell-free extracts were measured at pH 4.0, and they were compared with an activity of the wild strain.

Table 9 shows the result of measurement of phosphomonoesterase activities and transphosphorylation acitivities of wild type acid phosphatase and acid phosphatases with lowered phosphomonoesterase activity. It shows that both of phosphomonoesterase activities and traxsphosphorylation acitivities of acid phosphatases with lowered phosphomonoesterase activity are lowered as compared with wild type acid phosphatase, and that degrees of decrease of phosphomonoesterase activities are larger than that of transphosphorylation activities, with the result that the ratio of phosphomonoesterase activity to transphosphorylation activity of the mutant acid phosphatase is lowered in comparison with the wild type acid phosphatase.

TABLE 9

| Plasmid | Phosphomonoesterase activity (units/mg) | Transphosphorylation Activity (units/mg) | Ratio[1] (Relative Value) |
| --- | --- | --- | --- |
| pEPI305 | 2.38 | 0.132 | 18.03 (100) |
| pEPI310 | 0.26 | 0.019 | 13.68 (76) |
| pEPI320 | 0.88 | 0.123 | 7.15 (39) |
| pEPI330 | 0.42 | 0.070 | 6.00 (33) |

[1]Ratio of phosphomonoesterase activity to the activity to produce nucleoside-5'-phosphate ester Example 16

Production of 5'-Inosine Acid from Inosine by Using The Strains Harboring a Gene Encoding The Acid Phosphatase with Lowered Phosphomonoesterase Activity

*Escherichia coil* JM109/pEPI310, *Escherichia coli* JM109/pEPI320, and *Escherichia coil* JM109/pEPI330 into which the plasmids containing the genes encoding the acid phosphatases with lowered phosphomonoesterase activity had been introduced, and *Escherichia coli* JM109/pEPI305 into which the plasmid containing the wild type acid phosphatase gene had been introduced were inoculated to an L medium (50 ml) containing 100 µg/ml of ampicillin and 1 mM of IPTG, and they were cultivated at 37° C. for 16 hours.

Sodium pyrophosphate (12 g/dl) and inosine (6 g/dl) were dissolved in sodium acetate buffer (pH 4.0), to which microbial cells of each of the strains of *Escherichia coli* obtained by the cultivation described above were added to give a cell concentration of 200 mg/dl as converted into a dry weight of the microbial cells. The reaction mixture was incubated at 35° C. for 32 hours while maintaining pH at 4.0, and the amount of produced 5'-inosinic acid was measured along with passage of time. The result is shown in FIG. 7.

Figure 7:
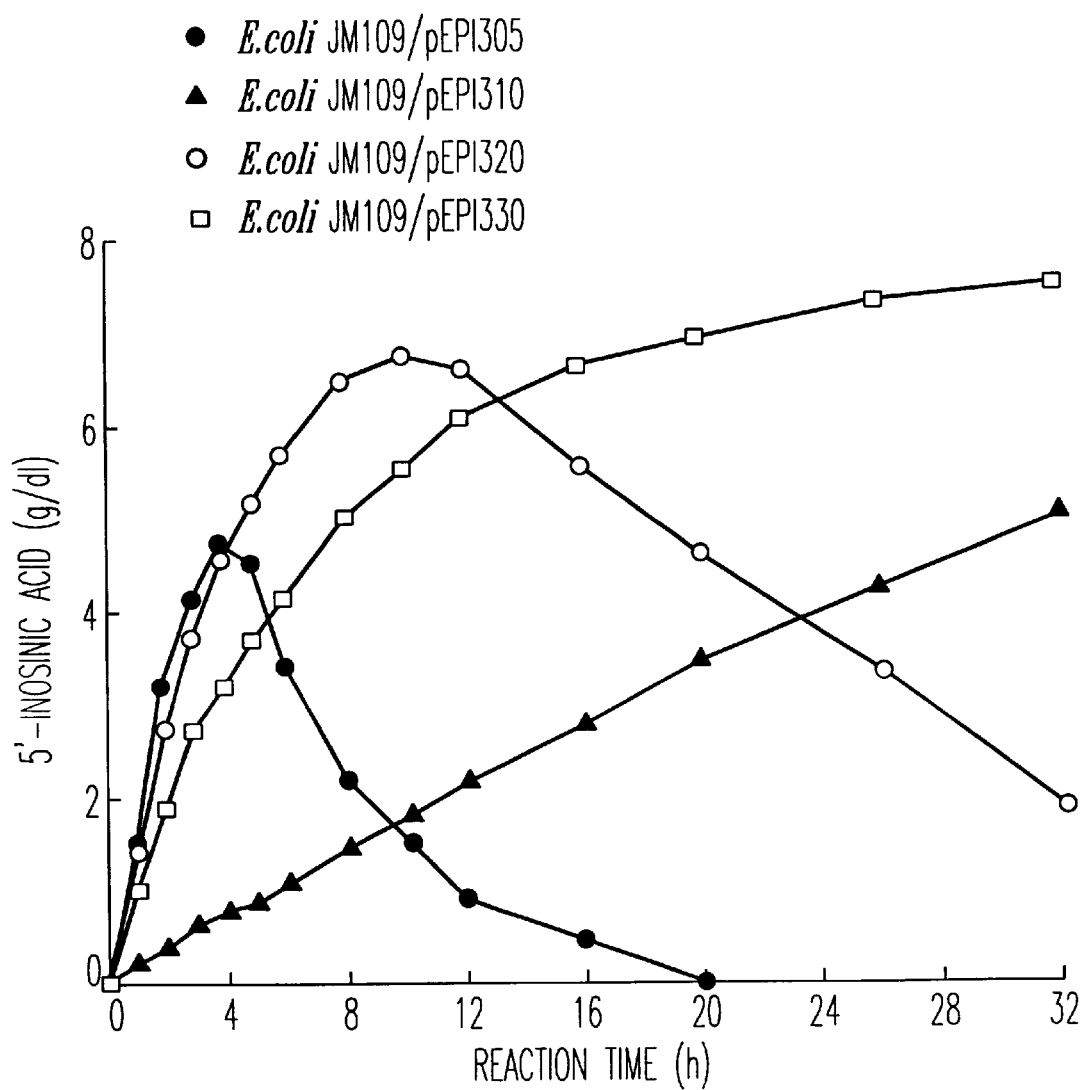
FIG. 7 illustrates the amount of 5'-inosinic acid produced in reactions performed with a strain harboring the wild-type acid phosphatase gene and a strain harboring the mutant acid phosphatase gene derived from *Escherichia blattae*.

In FIG. 7, the axis of ordinate indicates the concentration of 5'-inosinic acid (mg/dl), and the axis of abscissa indicates the reaction time (h). Progress of the reaction is indicated by solid circles for *Escherichia coli* JM109/pEPI305, solid triangles for *Escherichia coli* JM109/pEPI310, blanked circles for *Escherichia coli* JM109/pEPI320, and blanked squares for *Escherichia coil* JM109/pEPI330, as measured by using the cells of the respective strains.

The velocity of degradation of produced 5'-inosinic acid was decreased in the reaction to produce 5'-inosinic acid from inosine by using the stains harboring the acid phosphatase with lowered phosphomonoesterase activity. As a result, the yield and the accumulated amount of 5'-inosinic acid were increased. The highest accumulation of 5'-inosinic acid was exhibited by *Escherichia coli* JM109/pEPI330 as the strain harboring the gene encoding the acid phosphatase with lowered phosphomonoesterase activity in which the 74th glycine residue and the 153th isoleucine residue were substituted with the aspartic acid residue and the threonine residue respectively.

Example 17

Production of Various Nucleoside-5'-Phosphate Esters by Using The Strains Horboring a Gene Encoding The Acid Phosphatase with Lowered Phosphomonoesterase Activity

*Escherichia coli* JM109/pEPI330 into which the plasmid containing the gene encoding the acid phosphatase with lowered phosphomonoesterase activity had been introduced was inoculated to an L medium (50 ml) containing 100 µg/ml of ampicillin and 1 mM of IPTG, and it was cultivated at 37° C. for 16 hours.

Sodium pyrophosphate (12 g/dl), and inosine, guanosine, uridine, or cytidine (6 g/dl) as a phosphate group acceptor were dissolved in 100 mM sodium acetate buffer (pH 4.0), to which the microbial cells described above were added to give a cell concentration of 200 mg/dl as converted into a dry weight of the cells. The reaction mixture was incubated at 35° C. for 32 hours while maintaining pH at 4.0. Amounts of produced nucleoside-5'-phosphate esters are shown in Table 10. Produced nucleotide contained only nucleoside-5'-phosphate ester. By-production of nucleoside-2'-phosphate ester and nucleoside-3'-phosphate ester was not observed at all.

TABLE 10

| Nucleoside | Product | Amount Produced (g/dl) |
|---|---|---|
| Inosine | 5'-inosinic acid | 7.45 |
| Guanosine | 5'-guanylic acid | 4.77 |
| Uridine | 5'-uridylic acid | 8.93 |
| Cytidine | 5'-cytidylic acid | 6.60 |

Example 18

Production of 5'-Inosinic Acid from Various Phosphate Compounds as Phosphate Group Donors by Using The Strains Horboring a Gene Encoding The Acid Phosphatase with Lowered Phosphomonoesterase Activity

*Escherichia coli* JM109/pEPI330 into which the plasmid containing the mutant acid phosphatase gene had been introduced was inoculated to an L medium (50 ml) containing 100 µg/ml of ampicillin and 1 mM of IPTG, and it was cultivated at 37° C. for 16 hours.

Inosine (6 g/dl) and sodium tripolyphosphate, sodium polyphosphate (trade name: Polygon P, produced by Chiyoda Chemical), disodium phenylphosphate, or disodium carbamyl phosphate (12 g/dl) as a phosphate group donor were dissolved in 100 mM sodium acetate buffer (pH 4.0), to which the microbial cells described above were added to give a cell concentration of 200 mg/dl as converted into a dry weight of the cells. The reaction mixture was incubated at 35° C. for 32 hours while maintaining pH at 4.0. The amount of produced 5'-inosinic acid is shown in Table 11. 5'-Inosinic acid was efficiently produced and accumulated by using any of the phosphate group donors. However, the accumulated amount of 5'-inosinic acid was the highest when polyphosphoric acid was used as the phosphate group donor.

TABLE 11

| Phosphate group donor | Produced 5'-inosinic acid (g/dl) |
|---|---|
| Sodium tripolyphosphate | 5.96 |
| Sodium polyphosphate | 8.84 |
| Disodium phenylphosphate | 7.60 |
| Disodium carbamyl phosphate | 7.73 |

Example 19

Studies on Production of a New Mutant Acid Phosphatase Gene Derived from *E. blattae* JCM1650 and Enzymological Properties of the Mutant Acid Phosphatase Gene In Examples 19 to 22, the transphosphorylation activity to a nucleoside was measured under the following conditions. The reaction was conducted at 30° C. and a pH of 4.0 for 10 minutes using 1 ml of a reaction solution containing 40 µml/ml of inosine, 100 µmol/ml of sodium pyrophosphate, 100 µmol/ml of a sodium acetate buffer (pH 4.0) and an enzyme. This reaction was terminated with the addition of 200 µl of 2-N hydrochloric acid. Then, the precipitate was removed through centrifugation, and the amount of 5'-inosinic acid formed through the transphosphorylation was determined under the above-mentioned conditions. The amount of the enzyme with which to produce 1 µmol of inosinic acid under these standard reaction conditions was defined as 1 unit.

Further, the transphosphorylation activity was measured by changing the inosine concentration from 10 to 100 μmol/ml under the reaction conditions of the above-mentioned composition, and the rate constant of inosine in the tansphosphorylation activity was determined using the Hanes-Woolf plot [Biochem. J., 26, 1406 (1932), incorporated herein by reference].

As described below, the detailed analysis was conducted with respect to the mutant enzyme by which to improve the productivity of the nucleoside-5'-phosphate ester described in Example 15. Consequently, it was found that the affinity for nucleoside of the mutant enzyme was improved by 2 times as compared with that of the wild-type enzyme. Therefore, the present inventors considered that the productivity of the nucleoside-5'-phosphate ester could be improved by increasing the affinity for nucleoside of the above-mentioned enzyme, and they further modified the enzyme by the genetic engineering method.

Plasmid pEPI305 containing the gene encoding the wild-type acid phosphatase derived from *E. blattae* described in Example 15 was used, and the site specific mutation was introduced into this plasmid DNA by the genetic engineering method to produce a gene encoding the mutant acid phosphatase. pEPI305 is a plasmid DNA formed by binding a DNA fragment of 2.4 Kbp cleaved with restriction endonucleases ClaI and BamHI and containing a gene encoding a wild-type acid phosphatase derived from *E. blattae* JCM1650 to pBluescript KS(+) (supplied by Stratagene) cleaved with ClaI and BamHI. The base sequence of the gene encoding the acid phosphatase is represented by SEQ ID NO: 6 in the Sequence Listing. Further, an amino acid sequence of a precursor protein anticipated from this base sequence is represented by SEQ ID NO: 7 in the Sequence Listing. From the analytical results of the purified enzyme (described in Example 4), the amino acid sequence of the maturation protein is presumed to be represented by SEQ ID NO: 8 in the Sequence Listing.

Oligonucleotides MUT300 (SEQ ID NO: 9 in the Sequence Listing), MUT310 (SEQ ID NO: 10 in the Sequence Listing), MUT320 (SEQ ID NO: 11 in the Sequence Listing), MUT330 (SEQ ID NO: 12 in the Sequence Listing), MUT340 (SEQ ID NO: 13 in the Sequence Listing), MUT350 (SEQ ID NO: 14 in the Sequence Listing), MUT360 (SEQ ID NO: 15 in the Sequence Listing), MUT370 (SEQ ID NO: 16 in the Sequence Listing), MUT380 (SEQ ID NO: 17 in the Sequence Listing) and MUT390 (SEQ ID NO: 18 in the Sequence Listing) were synthesized by the phosphoamidite method using a DNA synthesizer (Model 394 supplied by Applied Biosystem).

One nanogram of pEPI305 as a template, 2.5 mols of M13 Primer RV (supplied by Takara Shuzo Co., Ltd.), 2.5 μmols of oligonucleotide MUT310 and 2.5 units of tac DNA polymerase (supplied by Takara Shuzo Co., Ltd.) were added to 100 μl of a Tris-hydrochloride buffer (pH 8.3) containing 200 μM of dATP, 200 M of dCTP, 200 μM of dGTP, 200 μM of dTTP, 50 mM of potassium chloride and 1.5 mM of magnesium chloride. PCR was conducted in which a three-part step, namely, at 94° C. for 30 seconds, at 55° C. for 2 minutes and at 72° C. for 3 minutes was repeated 25 times. In this reaction, a thermal cycler PJ2000 model (supplied by Takara Shuzo Co., Ltd.) was used. Separately, PCR was likewise conducted using 1 ng of plasmid DNA pEPI305 as a template, 2.5 μmols of M13 Primer M3 (supplied by Takara Shuzo Co., Ltd.) as a primer and 2.5 μmols of oligonucleotide MUT300. Each of the reaction solutions was purified through gel filtration using a microspin column S-400 (supplied by Pharmacia) to remove the primer.

One microliter of each of the PCR solutions was added to 95 μl of a 100-mM Tris-hydrochloride buffer (pH 8.3) containing 200 μM of dATP, 200 μM of dCTP, 200 μM of dGTP, 200 μM of dTTP, 50 mM of potassium chloride and 1.5 mM of magnesium chloride. The mixture was heated at 94° C. for 10 minutes, then cooled to 37° C. over the course of 60 minutes, and warmed at 37° C. for 15 minutes to form a heteroduplex. To this were added 2.5 units of tac DNA polymerase, and the reaction was conducted at 72° C. for 3 minutes to complete the heteroduplex. Subsequently, 2.5 μmols of M13 Primer RV and 2.5 μmols of M13 Primer M3 were added to the reaction solution, and PCR was conducted in which a three-part step, namely, at 94° C. for 30 seconds, at 5° C. for 2 minutes and at 72° C. for 3 minutes was repeated 10 times.

The second PCR product was cleaved with ClaI and BamHI, then extracted with a mixture of phenol and chloroform, and precipitated with ethanol. This DNA fragment was bound to pBluescript KS (+) cleaved with ClaI and BamHI. *E. coli* JM109 (supplied by Takara Shuzo Co., Ltd.) was transformed in a usual manner using the resulting plasmid DNA.

This was plated on an L agar medium containing 100 μg/mil of ampicillin to obtain a transformant. A plasmid was prepared from the transformant by an alkali bacteriolysis method, the base sequence was determined, and it was identified that the desired base was substituted. The determination of the base sequence was conducted by the method of Sanger et al. [*J. Mol. Biol.,* 143, 161 (1980)] using a Taq DyeDeoxy Terminator Cycle Sequencing Kit (supplied by Applied Biochemical). In this manner, the mutant gene encoding the mutant phosphatase in which the 74th glycine residue (GGG) of the maturation protein was substituted with the aspartic acid residue (G*A*T) was produced. This mutant gene-containing plasmid was designated pEPI310 (Example 15).

The above-mentioned procedure was repeated using the plasmid having the mutation introduced therein as a template to cumulatively introduce the site-specific mutation. A plasmid was produced from the transformant by the alkali bacteriolysis method, the base sequence was determined, and it was identified that the desired base was substituted. The resulting mutant genes encoding the mutant phosphatase and the mutation sites are shown in Table 12. The amino acid residue in the mutation site indicates an amino acid residue in the amino acid sequence of the mature protein represented by SEQ ID NO: 8 in the Sequence Listing.

TABLE 12

| plasmid name | starting material | primer | mutation position and substituted amino acid |
| --- | --- | --- | --- |
| pEPI305 | — | | wild type |
| pEPI310 | pEPI305 | MUT300 MUT310 | 74Gly(GGG)→Asp(G*A*T) |
| pEPI330 | pEPI310 | MUT300 MUT320 | 74Gly(GGG)→Asp(G*A*T) 153Ile(ATC)→Thr(A*CC) |
| pEPI340 | pEPI330 | MUT300 MUT330 | 63Leu(CTG)→Gln(C*AG) 65Ala(GCG)→Gln(*C*AG) 66Gln(GAA)→Ala(G*CA) 74Gly(GGG)→Asp(G*A*T) 153Ile(ATC)→Thr(A*CC) |
| pEPI350 | pEPI340 | MUT300 MUT340 | 63Leu(CTG)→Gln(C*AG) 65Ala(GCG)→Gln(*C*AG) 66Glu(GAA)→Ala(G*CA) 74Gly(GGG)→Asp(G*A*T) 85Ser(TCC)→Tyr(T*AC) |

TABLE 12-continued

| plasmid name | starting material | primer | mutation position and substituted amino acid |
|---|---|---|---|
| pEPI360 | pEPI340 | MUT300 MUT350 | 153Ile(ATC)→Thr(A*CC) 63Leu(CTG)→Gln(C*AG) 65Ala(GCG)→Gln(*C*AG) 66Glu(GAA)→Ala(G*CA) 74Gly(GGG)→Asp(G*A*T) 135Thr(ACC)→Lys(A*A*A) 136Glu(GAG)→Asp(GA*C) 153Ile(ATC)→Thr(A*CC) |
| pEPI370 | pEPI360 | MUT300 MUT360 | 63Leu(CTG)→Gln(G*AG) 65Ala(GCG)→Gln(*C*AG) 66Glu(GAA)→Ala(G*CA) 69Asn(ACC)→Asp(*GAC) 71Ser(AGC)→Ala(*G*CC) 72Ser(AGT)→Ala(*G*CT) 74Gly(GGG)→Asp(G*A*T) 135Thr(ACC)→Lys(A*A*A) 136Glu(GAG)→Asp(GA*C) 153Ile(ATC)→Thr(A*CC) |
| pEPI380 | pEPI370 | MUT300 MUT370 | 63Leu(CTG)→Gln(C*AG) 65Ala(GCG)→Gln(*C*AG) 66Glu(GAA)→Ala(G*CA) 69Asn(AAC)→Asp(*GAC) 71Ser(AGC)→Ala(*G*CC) 72Ser(AGT)→Ala(*G*CT) 74Gly(GGG)→Asp(G*A*T) 116Asp(GAT)→Glu(GA*A) 135Thr(ACC)→Lys(A*A*A) 136Glu(GAG)→Asp(GA*C) 153Ile(ATC)→Thr(A*CC) |
| pEPI390 | pEPI380 | MUT300 MUT380 | 63Leu(CTG)→Gln(C*AG) 65Ala(GCG)→Gln(*C*AG) 66Glu(GAA)→Ala(G*CA) 69Asn(AAC)→Asp(*GAC) 71Ser(AGC)→Ala(*G*CC) 72Ser(AGT)→Ala(*G*CT) 74Gly(GGG)→Asp(G*A*T) 116Asp(GAT)→Glu(GA*A) 130Ser(TCT)→Glu(*G*A*A) 135Thr(ACC)→Lys(A*A*A) 136Glu(GAG)→Asp(GA*C) 153Ile(ATC)→Thr(A*CC) |
| pEPI400 | pEPI380 | MUT300 MUT390 | 63Leu(CTG)→Gln(C*AG) 65Ala(GCG)→Gln(*C*AG) 66Glu(GAA)→Ala(G*CA) 69Asn(AAC)→Asp(*GAC) 71Ser(AGC)→Ala(*G*CC) 72Ser(AGT)→Ala(*G*CT) 74Gly(GGG)→Asp(G*A*T) 92Ala(GCC)→Ser(*A*GC) 94Ala(GCG)→Glu(G*A*A) 116Asp(GAT)→Glu(GA*A) 135Thr(ACC)→Lye(A*A*A) 136Glu(GAG)→Asp(GA*C) 153Ile(ATC)→Thr(A*CC) |

Each of *E. coli* JM109/pEPI330, *E. coli* JM109/pEPI340, *E. coli* JM109/pEPI350, *E. coli* JM109/pEPI360, *E. coli* JM109/pEPI370, *E. coli* JM109/pEPI380, *E. coli* JM109/pEPI390 and *E. coli* JM109/pEPI400 each having introduced therein a plasmid containing the mutant acid phosphatase gene and *E. coli* JM109/pEPI305 having introduced therein a plasmid containing a wild-type acid phosphatase gene was inoculated into 50 ml of an L medium containing 100 μg/ml of ampicillin and 1 mM of IPTG, and incubated at 37° C. for 16 hours. The cells were collected from 2 liters of the culture solution of each of the strains through centrifugation, and washed once with a physiological saline solution. The cells were suspended in 50 ml of a 100-mM phosphate buffer (pH 7.0), and sonicated at 4° C. for 20 minutes to disrupt the cells. The thus-treated solution was centrifuged to remove insoluble fractions and prepare a cell-free extract. Each of the acid phosphatases was purified from each of the cell-free extracts by the method described in Example 4. Each of the enzyme products was uniform in the SDS-polyacrylamide electrophoresis.

The rate constant of inosine in the transphosphorylation of the purified mutant acid phosphatases and wild-type acid phosphatase was measured, and the results are shown in Table 13. It was found that the mutant enzyme expressed in *E. coli* JM109/pEPI330 having the improved productivity of the nucleoside-5'-phosphate ester as described in Example 15 has decreased $V_{max}$ but greatly decreased the $K_m$ value to inosine which means the increased affinity for inosine by twice or more as compared with the wild-type enzyme expressed in *E. coli* JM109/pEPI305. This suggested that the productivity of the nucleoside-5'-phosphate ester of this mutant enzyme was greatly improved not only because of the decrease in the nucleotidase activity but also because of the improvement in the affinity for nucleoside which was an important factor. Accordingly, it was expected that the increase in the affinity for nucleoside leads to the improvement in the productivity.

The new mutant enzymes expressed in *E. coli* JM109 having been introduced therein with the new mutant enzyme gene produced in this Example exhibited the affinity for inosine which was more improved than that of *E. coli* JM109/pEPI330 described in Example 15. Thus, it was expected that the productivity of the nucleoside-5'-phosphate ester was improved. Further, the mutant enzyme expressed in *E. coli* JM109/pEPI380 not only improved the affinity for inosine but also increased the $V_{max}$ value as compared with the wild-type enzyme. Still further, it was expected that the productivity of the nucleoside-5'-phosphate ester was improved.

TABLE 13

| Strain of an enzyme | $K_m$ (mM) | $V_{max}$ (unit/mg) |
|---|---|---|
| *E. coli* JM109/pEPI305 | 202 | 1.83 |
| *E. coli* JM109/pEPI330 | 109 | 1.39 |
| *E. coli* JM109/pEPI340 | 85 | 1.03 |
| *E. coli* JM109/pEPI350 | 85 | 0.93 |
| *E. coli* JM109/pEPI360 | 55 | 1.33 |
| *E. coli* JM109/pBPI370 | 42 | 1.15 |
| *E. coli* JM109/pEPI380 | 42 | 2.60 |
| *E. coli* JM109/pEPI390 | 42 | 2.58 |
| *E. coli* JM109/pEPI400 | 43 | 2.11 |

Example 20

Production of 5'-inosinic Acid using a New Mutant Acid Phosphatase Gene-Containing Strain Each of *E. coli* JM109/pEPI330, *E. coli* JM109/pEPI340, *E. coli* JM109/pEPI360, *E. coli* JM109/pEPI370 and *E. coli* JM109/pEPI380 each having introduced therein the plasmid containing the mutant acid phosphatase gene was inoculated into 50 ml of an L medium containing 100 μg/ml of ampicillin and 1 mM of IPTG, and incubated at 37° C. for 16 hours.

Figure 8:
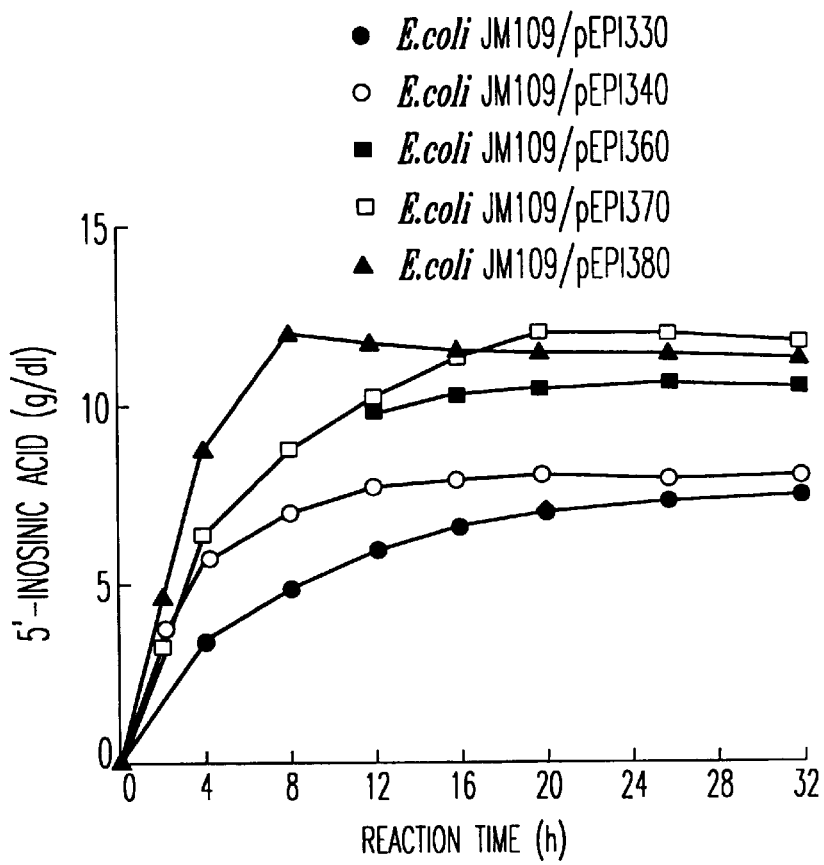
FIG. 8 illustrates the amount of 5'-inosinic acid produced in a reaction performed with a strain harboring the new mutant acid phosphatase gene derived from *Escherichia blattae*.

Pyrophosphoric acid (15 g/dl) and 8 g/dl of inosine were dissolved in an acetate buffer (pH 4.0). To the solution was added *E coil* JM109 strain having introduced therein the above-mentioned mutant and wild-type acid phosphatase genes such that the concentration reached 200 mg/dl in terms of the dry cell weight. The reaction was conducted at 35° C. for 32 hours while maintaining the pH at 4.0, and the amount of 5'-inosinic acid formed over the course of time was measured. Inosinic acid formed was only 5'-inosinic acid, and the formation of 2'-inosinic acid and 3'-inosinic acid as by-products was not observed at all. The results are shown in FIG. 8.

E. coli JM109/pEPI330 described in Example 15 showed the accumulation of 5'-inosinic acid in a large amount. Although the substrate still remained, the formation of 5'-inosinic acid stopped when the amount of 5'-inosinic acid accumulated reached 7.5 g/dl, and the amount of 5'-inosinic acid was no longer increased. By contrast, the new mutant acid phosphatase gene-containing strains provided the large amount of 5'-inosinic acid accumulated. Especially, in the reaction using E. coli JM109/pEPI370 and E. coli JM109/pEPI380, the larger amount of 5'-inosinic acid accumulated was provided. In addition, the reaction rate was high, showing that the productivity of 5'-inosinic acid was further improved greatly. In particular, in E. coli JM109/pEPI380, the reaction rate was high, and quite a high reactivity was shown.

Example 21

Production of Various Nucleoside-5'-phosphate Esters using a New Mutant Acid Phosphatase Gene-Containing Strain E. coli JM109/pEPI380 having introduced therein the plasmid containing the new mutant acid phosphatase gene was inoculated into 50 ml of an L medium containing 100 μg/ml of ampicillin and 1 mM of IPTG, and incubated at 37° C. for 16 hours.

Pyrophosphoric acid (15 g/dl) and 8 g/dl of inosine, guanine, uridine or cytidine as a phosphate acceptor were dissolved in a 100 mM acetate buffer (pH 4.5). To this was added the above-mentioned strain such that the concentration reached 100 mg/dl in terms of the dry cell weight. The reaction was conducted at 35° C. for 12 hours while maintaining the pH at 4.0. The amount of the nucleoside-5'-phosphate ester formed is shown in Table 14. The phosphorylation proceeded well with any of the nucleosides to form and accumulate the corresponding nucleoside-5'-phosphate esters. The nucleotide formed was only the nucleoside-5'-phosphate ester, and the formation of a nucleoside-2'-phosphate ester and a nucleoside-3'-phosphate ester as by-products was not observed at all.

TABLE 14

| Nucleoside | Product | Amount of the Product (g/dl) |
|---|---|---|
| inosine | 5'-inosinic acid | 12.05 |
| guanosine | 5'-guanylic acid | 5.78 |
| uridine | 5'-uridylic acid | 13.28 |
| cytidine | 5'-cytidylic acid | 10.65 |

Example 22

Production of 5'-Inosinic Acid Using a New Acid Phosphatase Gene-Containing Strain and Various Phosphoric Acid Compounds as a Phosphate Donor E. coli JM109/pEPI380 having introduced therein the plasmid containing the new mutant acid phosphatase gene was inoculated into 50 ml of an L medium containing 100 μg/ml of ampicillin and 1 mM of IPTG, and incubated at 37 C. for 16 hours.

Inosine (6 g/dl) and 15 g/dl of a tripolyphosphate, a polyphosphate ("Polygon P", a trade name for a product of Chiyoda Kagaku K.K.), disodium phenylacetate or disodium carbamylphosphate were dissolved in a 100-mM acetate buffer (pH 4.0). To this was added the above-mentioned strain such that the concentration reached 100 mg/dl in terms of the dry cell weight. The reaction was conducted at 35° C. for 12 hours while maintaining the pH at 4.0. The amount of 5'-inosinic acid formed was shown in Table 15. 5'-Inosinic acid was formed and accumulated at good efficiency with any of the phosphate donors. Especially when a polyphosphate was used as a phosphate donor, 5'-inosinic acid was accumulated in the largest amount.

TABLE 15

| Phosphate donor | Amount of 5'-inosinic acid formed (g/dl) |
|---|---|
| sodium tripolyphosphate | 10.84 |
| sodium polyphosphate | 13.35 |
| disodium phenylphosphate | 12.84 |
| disodium carbamylphosphate | 12.42 |
| potassium lithium acetylphosphate | 10.65 |

Example 23

Isolation of Acid Phosphatase Gene Derived from Chromosome of *Providencia stuartii* and Determination of Nucleotide Sequence of the Gene Oligonucleotides, PRP1 and PRP2, having nucleotide sequences illustrated in SEQ ID NO: 19 and 20 in the Sequence Listing, respectively, were synthesized. These oligonucleotides are designed to amplify a gene coding for acid phosphatase of *Providencia stuartii* on the basis of known nucleotide sequence of the gene coding for acid phosphatase of *Providencia stuartii* (Database of EMBL Accession number X64820).

Chromosomal DNA was extracted from cultivated microbial cells of *Providencia stuartii* ATCC 29851 in accordance with a method of Murray and Thomson (*Nucl. Acid Res.,* 4321, 8 (1980)). The chromosomal DNA (0.1 ng) as a template, oligonucleotides PRP1 and PRP2 (each 2.5 μmol) as primers, and Taq DNA polymerase (2.5 units, produced by Takara Shuzo) were added to 100 mM Tris-HCl buffer (pH 8.3, 100 l) containing dATP, dCTP, dGTP, dTTP (each 200 μM), potassium chloride (50 mM), and magnesium chloride (1.5 mM) to perform a PCR reaction in which a cycle comprising periods of 30 seconds at 94° C., 2 minutes at 55° C., and 3 minutes at 72° C. was repeated 30 times. The reaction solution was subjected to agarose gel electrophoresis, followed by recovering the amplified DNA fragment of about 1 kbp by means of glass powders (made by Takara Shuzo). The gene fragment was digested with BamHI, which was ligated with pUC118 digested with BamHI. The plasmid obtained as described above was designated as pPRP100.

Phosphomonoesterase activity and transphosphorylation activity of *Escherichia coli* JM109/pPRP100, a transformant to which pPRP100 was introduced, were measured. As a result, the strain showed an activity to transphosphorylate to nucleoside as well as phosphomonoesterase activity.

The plasmid was extracted in accordance with the alkaline lysis method from the transformant of *Escherichia coli* JM109/pPRP100 to determine the nucleotide sequence. A nucleotide sequence of a determined open reading frame and an amino acid sequence of the protein deduced from the nucleotide sequence are shown in SEQ ID NO: 21 and 22 in the Sequence Listing. The nucleotide sequence of the open reading frame is completely coincident with the nucleotide sequence of the known acid phosphatase gene of *Providencia stuartii*.

Example 24

Isolation of Acid Phosphatase Genes Derived from Chromosomes of *Enterobacter aerogenes*, *Klebsiella planticola* and *Serratia ficaria* and Determination of Nucleotide Sequences of the Genes Chromosomal DNA was extracted from cultivated microbial cells of *Enterobacter aerogenes* IFO 12010, *Klebsiella planticola* IFO 14939 and *Serratia ficaria* IAM 13540 in accordance with a method of Murray and Thomson (*Nucl. Acid Res.*, 4321, 8 (1980)). Then, in accordance with the method described in Example 7(2), a chromosomal gene expression library comprising about 20,000 transformants of *Escherichia coli* JM109 was constructed and screened to obtain transformants which showed transphosphorylation activity. It was considered that each of these transformants harbors the acid phosphatase gene derived from each of the original strains.

Figure 9:
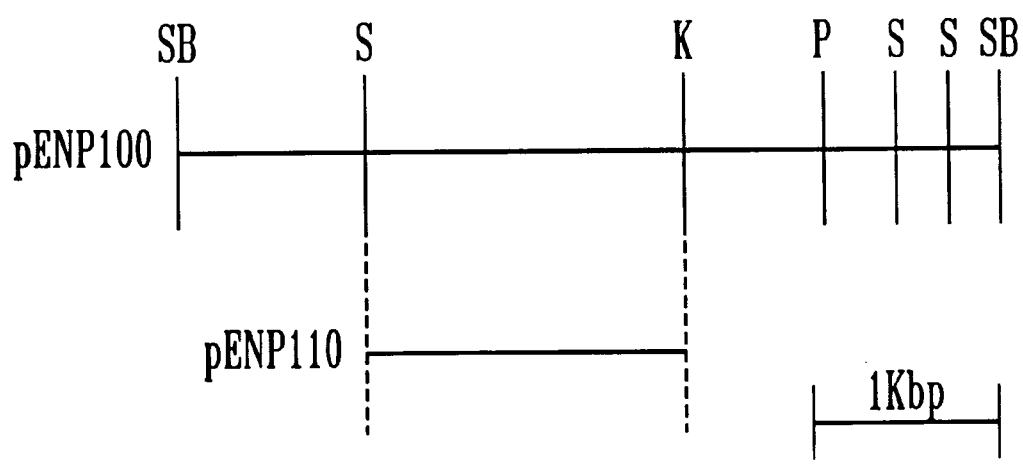
FIG. 9 illustrates a restriction enzyme map of a chromosomal DNA fragment derived from *Enterobacter aerogenes* which contains the gene coding for an acid phosphatase.

Plasmid DNA was extracted from one of the transformants of *Escherichia coli* which was considered to have the acid phosphatase gene derived from *Enterobacter aerogenes* IFO 12010 in accordance with an alkaline lysis method and the inserted DNA of the plasmid was analyzed. The above plasmid was designated as pENP100. A restriction enzyme map of the inserted DNA derived from *Enterobacter aerogenes* IFO 12010 is shown in FIG. 9.

As a result of specifying the region of acid phosphatase gene by subcloning, it was suggested that the acid phosphatase gene is contained in the 1.6 kbp fragment excised by restriction enzymes SalI and KpnI. Then, the SalI- KpnI fragment was ligated with pUC118 which was digested with SalI and KpnI to construct a plasmid. The resulting plasmid was designated as pENP110.

Figure 10:
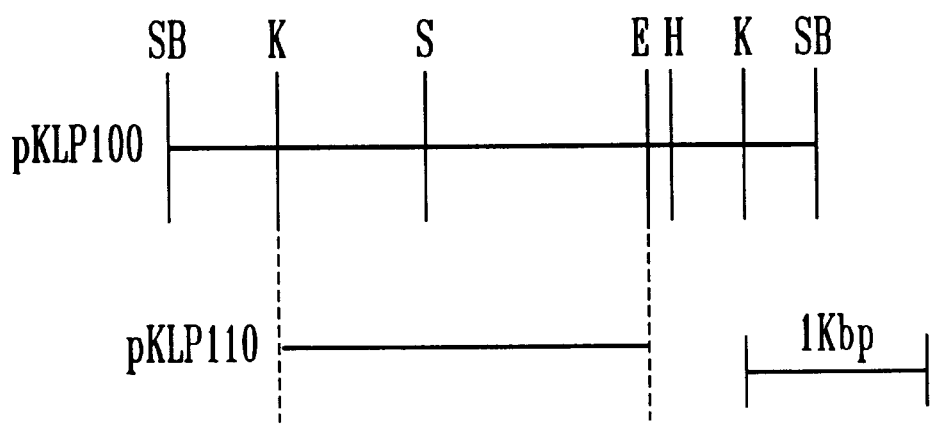
FIG. 10 illustrates a restriction enzyme map of a chromosomal DNA fragment derived from *Klebsiella planticola* which contains the gene coding for an acid phosphatase.

According to the procedure as described above, plasmid DNA was extracted from one of the transformants of *Escherichia coli* which was considered to have the acid phosphatase gene derived from *Klebsiella planticola* IFO 14939 in accordance with an alkaline lysis method and the insert DNA of the plasmid was analyzed. The above plasmid was designated as pKLP100. A restriction enzyme map of the inserted DNA derived from *Klebsiella planticola* IFO 14939 is shown in FIG. 10.

As a result of specifying the region of acid phosphatase gene by subcloning, it was suggested that the acid phosphatase gene is contained in the 2.2 kbp fragment excised by restriction enzymes KpnI and EcoRI. Then, the KpnI- EcoRI fragment was ligated with pUC118 which was digested with KpnI and EcoRI to construct a plasmid. The resulting plasmid was designated as pKLP110.

Figure 11:
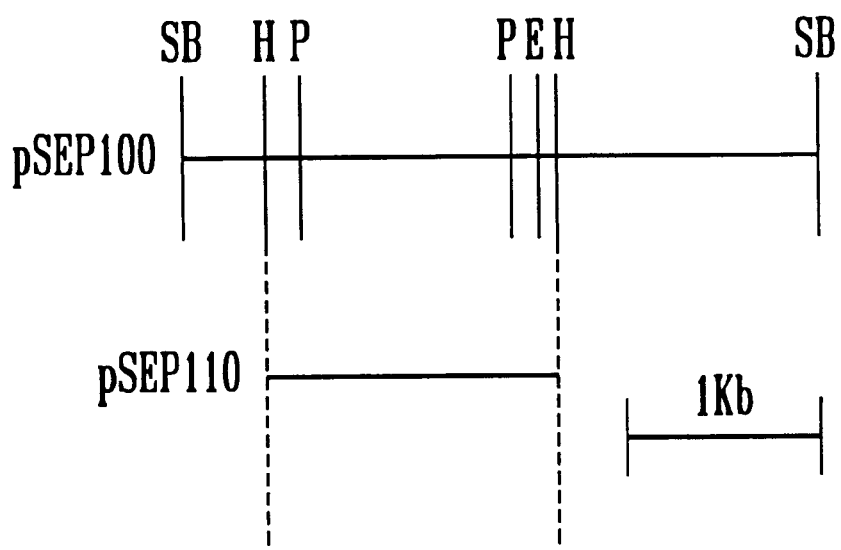
FIG. 11 illustrates a restriction enzyme map of a chromosomal DNA fragment derived from *Serratia ficaria* which contains the gene coding for an acid phosphatase.

Similarly, plasmid DNA was extracted from one of the transformants of *Escherichia coli* which was considered to have the acid phosphatase gene derived from *Serratia ficaria* IAM 13540 in accordance with an alkane lysis method and the inserted DNA of the plasmid was analyzed. The above plasmid was designated as pSEP100. A restriction enzyme map of the inserted DNA derived from *Serratia ficaria* IAM 13540 is shown in FIG. 11.

As a result of specifying the region of acid phosphatase gene by subcloning, it was suggested that the acid phosphatase gene is contained in the 1.4 kbp fragment excised by restriction enzymes HindIII. Then, the HindIII fragment was ligated with pUC118 which was digested with HindIII to construct a plasmid. The resulting plasmid was designated as pSEP110.

Then, the plasmid DNAs were extracted from the trasformants, *Escherichia coli* JM109/pENP110, *Escherichia coli* JM109/pKLP110 and *Escherichia coli* JM109/pSEP110, to which pENP110 pKLP110 and pSEP110 had been introduced, respectively, in accordance with an alkaline lysis method. The nucleotide sequences of inserts of these plasmids were determined in accordance with the method described in Example 8. The determined nucleotide sequences of open reading frames of the inserts are shown in SEQ ID NO :23 for *Enterobacter aerogenes* IFO 12010, in SEQ ID NO: 25 for *Klebsiella planticola* IFO 14939 and in SEQ ID NO: 27 for *Serratia ficaria* IAM 13540. Additionally, the deduced amino acid sequences are shown in SEQ ID NO: 24, 26 and 28, respectively. Because of the fact that the transformants harboring the plasmids containing these fragments exhibited the transphosphorylation activity, it was identified that these open reading frames were the objective acid phosphatase genes.

The nucleotide sequences and the deduced amino acid sequences were respectively compared with known sequences for homology. Data bases of EMBL and SWISS-PROT were used. As a result, it has been revealed that the genes illustrated in SEQ ID NO: 23, 25 and 27 in the Sequence Listing are new genes. It is assumed that the protein encoded by the gene derived from *Enterobacter aerogenes* IFO 12010 comprises 248 amino acid residues, the protein encoded by the gene derived from *Klebsiella planticola* IFO 14939 comprises 248 amino acid residues and the protein encoded by the gene derived from *Serratia ficaria* IAM 13540 comprises 244 amino acid residues. There is a possibility that these proteins may be precursor proteins like the acid phosphatases derived from *Morganella morganii* and *Escherichia blattae*.

The amino acid sequences deduced from the nucleotide sequences are shown in FIG. 12 in one-letter symbols together with the deduced amino acid sequence of the acid phosphatase derived from *Morganella morganii* NCIMB 10466 obtained in Example 8, that of *Escherichia blattae* JCM 1650 obtained in Example 12 and the known amino acid sequence of the acid phosphatase of *Providencia stuartii* (EMBL Accession number X64820). Common amino acid residues among all of the amino acids sequences are indicated with asterisks under the sequences in FIG. 12.

As shown in FIG. 12, the amino acid sequences of the acid phosphatases derived from six strains are highly homologous each other and 130 amino acid residues are common among all of the amino acid sequences. Thus, it is assumed that these acid phosphatases have similar functions.

Example 25

Amplification of Activity by Expressing Gene of Acid Phosphatase Derived from *Enterobacter aerogenes*, *Klebsiella planticola* and *Serratia ficaria*

*Escherichia coli* JM109/pPRP100 constructed in Example 23, *Escherichia coli* JM109/pENP110, *Escherichia coil* JM109/pKLP110 and *Escherichia coil* JM109/pSEP110 constructed in Example 24 were inoculated to an L-medium (50 ml) containing 100 μg/ml of ampicillin and 1 mM of IPTG, and were cultivated at 37° C. for 16 hours. Microbial cells were harvested from these cultures by centrifugation, and they were washed once with physiological saline. The microbial cells were suspended in 100 mM potassium phosphate buffer (5 ml, pH 7.0), and they were disrupted by means of a ultrasonic treatment performed at 4° C. for 20 minutes. The treated solutions were centrifuged to remove an insoluble fraction, and thus cell-free extracts were prepared.

The transphosphorylation activities of the obtained cell-free extracts were measured while using controls of cell-free extracts prepared from *Providencia stuartii* ATCC 29851, *Enterobacter aerogenes* IFO 12010, *Klebsiella planticola* IFO 14939, *Serratia ficaria* IAM 13450, and *Escherichia coil* JM109 transformed with the plasmid pUC118 in the same manner as described above. The results are shown in Table 16. The transphosphorylation activities were low in all of the wild type strains. The transphosphorylation activity was not detected in *Escherichia coli* JM109/pUC118. On the other hand, the transformants of *Escherichia coli* JM109 to which the acid phosphatase genes were introduced exhibited high transphosphorylation activities in comparison with wild type strains. According to the result, it has been demonstrated that each of the introduced DNA fragment allow *Escherichia coli* to express the acid phosphatase at a high level.

TABLE 16

| Microbial strain | Transphosphrylation Activity (units/mg) |
| --- | --- |
| *Providencia stuartii* ATCC 29851 | 0.005 |
| *Enterobacter aerogenes* IFO 12010 | 0.002 |
| *Klebsiella planticola* IFO 14939 | 0.002 |
| *Serratia ficaria* IAM 13450 | 0.001 |
| *Escherichia coli* JM109/pUC118 | not detected |
| *Escherichia coli* JM109/pPRP100 | 0.833 |
| *Escherichia coli* JM109/pENP110 | 0.301 |
| *Escherichia coli* JM109/pKLP110 | 0.253 |
| *Escherichia coli* JM109/pSEP110 | 0.123 |

Example 26

Production of a Mutant Acid Phosphatase Gene Having an Improved Temperature Stability:

As described in Examples 20, 21 and 22, the *E. blattae*-derived mutant acid phosphatase gene-containing strain produced in Example 19 expressed the considerable amount of the acid phosphatase. In the production of 5'-inosinic acid from pyrophosphoric acid and inosine using this strain, 5'-inosinic acid was formed and accumulated in the high conversion yield. The optimum reaction temperature of this acid phosphatase was 35° C. However, when this reaction was conducted at a higher temperature, the reaction rate was increased, and the reaction was conducted upon increasing the nucleoside concentration of the phosphate acceptor in the reaction solution. Accordingly, it was expected that the nucleoside-5'-phosphate ester could be produced more efficiently for a shorter period of time. Thus, the temperature stability of the enzyme was improved upon introducing the mutation into the *E. blattae*-derived acid phosphatase gene cloned in Example 19 by the site specific mutation method using PCR.

Plasmid pEPI380 containing the gene encoding the *E. blattae* JCM1650-derived mutant acid phosphatase described in Example 19 was used, and the site specific mutation was introduced into this plasmid DNA by the genetic engineering method to produce the gene encoding the mutant acid phosphatase having the increased temperature stability. pEPI380 is a plasmid DNA obtained by binding a DNA fragment of 2.4 Kbp containing the gene encoding the mutant acid phosphatase derived from *E. blattae* JCM1650 and cleaved with restriction endonucleases ClaI and BamHI to pBluescript KS(+) (supplied by Stratagene) cleaved with ClaI and BamHI. The amino acid sequence of the mature protein anticipated from the base sequence of the gene encoding the acid phosphatase is presumed to be 11 amino acid resides shown in Table 12 in Example 19 in the sequence represented by SEQ ID NO: 8 in the Sequence Listing.

Oligonucleotides MUT300 (SEQ ID NO: 9 in the Sequence Listing), MUT400 (SEQ ID NO: 29 in the Sequence Listing) and MUT410 (SEQ ID NO: 30 in the Sequence Listing) having the sequences shown in the Sequence Table were synthesized by the phosphoamidite method using a DNA synthesizer (Model 394 supplied by Applied Biosystem).

A mutant gene encoding a mutant phosphatase in which the 104th glutamic acid residue (GAG) of a maturation protein was substituted with a glycine residue (GG*T*) was produced by the method with PCR as in Example 15 using pEPI380 described in Example 19 as a template and MUT300 and MUT410 as primers for introduction of mutation. This mutant gene-containing plasmid was designated pEPI410. Likewise, a mutant gene encoding a mutant phosphatase in which the 151st threonine residue (ACC) was substituted with an alanine residue (G*CC) was produced using pEPI380 as a template and oligonucleotides MUT300, MUT310 and MUT420 as primers for introduction of mutation. This mutant gene-containing plasmid was designated pEPI420.

A plasmid was produced from the transformant of *E. coli* JM109 having introduced therein plasmids pEPI410 and pEPI420 containing the mutant phosphatase gene by the alkali bacteriolysis method, the base sequence was determined, and it was identified that the desired base was substituted.

Each of *E. coli* JM109/pEPI410 and *E. coli* JM109/pEPI420 having introduced therein the mutant acid phosphatase gene as produced in this Example and *E. coli* JM109/pEPI380 described in Example 19 was inoculated in 50 ml of an L medium containing 100 μg/ml of ampicillin and 1 mM of IPTG, and incubated at 37° C. for 16 hours. The cells were collected from 50 ml of the culture solution of each of the strains, and washed once with a physiological saline solution. These cells were suspended in 5 ml of a 100-mM phosphate buffer (pH 7.0), and sonicated at 4° C. for 20 minutes to mill the cells. The thus-treated solution was centrifuged to remove insoluble fractions and prepare a cell-free extract.

Figure 13:
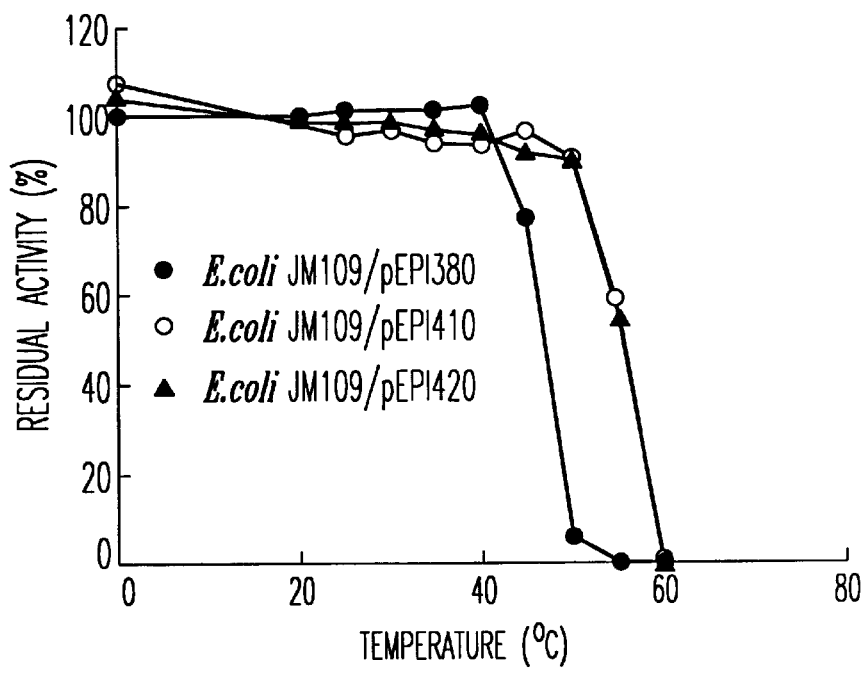
FIG. 13 illustrates a graph of the temperature stability of the acid phosphatase activity in the cell free extract solution prepared from a strain harboring the new mutant phosphatase gene derived from *Escherichia blattae*.

The cell-free extract formed from each of the strains was warmed at temperatures ranging from 0° C. to 80° C. with a pH of 7.0 for 30 minutes. After the completion of the warming, the transphosphorylation was conducted under the standard reaction conditions of pH of 4.0 and 30° C. using the cell-free extracts treated at various temperatures, and the residual activity was measured. The results are shown in FIG. 13. The mutant enzyme expressed in *E. coli* JM109/pEPI380 described in Example 19 was stable in the treatment at 40° C. for 30 minutes, but the decrease in the activity was observed at higher temperatures. By contrast, the new mutant enzyme expressed in *E. coli* JM109/pEPI410 and *E. coli* JM109/pEPI420 having introduced therein the new mutant enzyme gene as produced in this Example improved the temperature stability, and the decrease in the activity was not observed even through the treatment at 50° C. for 30 minutes. It was thus expected that when a nucleoside-5'-phosphate ester was produced using these strains at a high temperature, the productivity was further improved.

Example 27

Production of 5'-Inosinic Acid and 5'-Guanylic Acid using a Mutant Acid Phosphatase Gene-Containing Strain Having an Improved Temperature Stability Each of *E. coli* JM109/pEPI410 and *E. coli* JM109/pEPI420 having been introduced therein with the mutant acid phosphatase gene and *E. coli* JM109/pEPI380 described in Example 19 was inoculated in 50 ml of an L medium containing 100 μg/ml of ampicillin and 1 mM of IPTG, and incubated at 37° C. for 16 hours.

Pyrophosphoric acid (15 g/dl) and 8 g/dl of inosine or guanosine were dissolved in an acetate buffer (pH 4.0). To this was added *E. coli* JM109 strain having introduced therein each mutant acid phosphatase gene such that the concentration reached 100 mg/dl in terms of the dry cell weight. The reaction was conducted at 50° C. for 9 hours while maintaining the pH at 4.0, and the amount of 5'-inosinic acid or 5'-guanylic acid formed was measured. The results are shown in Table 17. The nucleoside phosphate ester formed was only a nucleoside-5'-phosphate ester, and the production of a nucleoside-2'-phosphate ester and a nucleoside-3'-phosphate ester as by-products was not observed at all. The reaction was also conducted at 30° C. for 12 hours using *E. coli* JM109/pEPI380 strain as a control. The results are also shown in Table 17.

As described in Example 21, the nucleoside-5'-phosphate ester was formed and accumulated efficiently with *E. coli* JM109/pEPI380. By contrast, when the reaction was conducted using *E. coli* JM109/pEPI410 and *E. coli* JM109/pEPI420 having been introduced therein with the new mutant acid phosphatase gene derived from *E. blattae* as produced in Example 26, 5'-inosinic acid or 5'-guanylic acid in the same amount was formed and accumulated for a shorter period of time. Thus, the nucleoside-5'-phosphate ester could be produced more efficiently. Especially when using *E. coli* JM109/pEPI420, not only was the reaction time shortened, but also were 5'-inosinic acid and 5'-guanylic acid accumulated in larger amounts, and quite a high productivity was shown.

Application No. 161674/1997, filed Jun. 18, 1997, both of which are incorporated herein by reference in their entirety.

TABLE 17

| Strain | Reaction temperature (° C.) | Reaction time (hr) | Amount of 5'-inosinc acid formed (g/dl) | Amount of 5'-guanylic acid formed (g/dl) |
| --- | --- | --- | --- | --- |
| *E. coli* JM109/pEPI380 | 30 | 12 | 12.05 | 5.78 |
| *E. coli* JM109/pEPI410 | 50 | 9 | 11.85 | 5.80 |
| *E. coli* JM109/pEIP420 | 50 | 9 | 12.60 | 6.11 |

Obviously, numerous modifications and variations of the present invention are possible in light of the above teachings. It is therefore to be understood that within the scope of the appended claims, the invention may be practiced otherwise than as specifically described herein.

This application is based on Japanese Patent Application No. 311103/1996, filed Nov. 21, 1996, and Japanese Patent

What is claimed as new and desired to be secured by Letters Patent of the United States is:

1. A mutant acid phosphatase wherein the wild-type acid phosphatase comprising an amino acid sequence selected from the group consisting of SEQ ID Nos: 4, 8, 24, 26, and 28, and said acid phosphatase has a mutation which decreases the $K_m$ value for a nucleoside and/or increases the temperature stability as compared to said wild-type acid phosphatase; wherein said nucleoside is selected from the group consisting of inosine, guanosine, adenosine, xanthosine, purine riboside, 6-methoxypurine riboside, 2,6-diaminopurine riboside, 6-fluoropurine riboside, 6-thiopurine riboside, 2-amino-6-thiopurine riboside, mercaptoguanosine uridine, cytidine, 5-aminouridine, 5-hydroxyuridine, 5-bromouridine, and 6-azauridine; and wherein the Km value for the nucleoside is determined by measuring the transphosphorylation activity of the acid phosphatase at 30° C. and pH4.0 in the presence of 100 µmol/ml of sodium pyrophosphate.

2. The mutant acid phosphatase of claim 1, wherein said mutation comprises substitution of the amino acid residue corresponding to the 63rd leucine residue, the 65th alanine residue, the 66th glutamic acid residue, the 69th asparagine residue, the 71st serine residue, the 72nd serine residue, the 74th glycine residue, the 85th serine residue, the 92nd alanine residue, the 94th alanine residue, the 104th glutamic acid residue, the 116th aspartic acid residue, the 130th serine residue, the 135th threonine residue, the 136th glutamic acid residue, the 15th threonine residue and the 153rd isoleucine residue of SEQ ID NO:8 with another amino acid.

3. The mutant acid phosphatase of claim 1, wherein said amino acid sequence is SEQ ID NO: 8.

* * * * *

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (v) FRAGMENT TYPE: N-terminal (vi) ORIGINAL SOURCE:
      (A) ORGANISM: Morganella morganii
      (B) STRAIN: NCIMB 10466

(xi) SEQUENCE DESCRIPTION: SEQ ID NO: 1:

```
Ala Ile Pro Ala Gly Asn Asp Ala Thr Thr Lys Pro Asp Leu Tyr Tyr
 1               5                  10                  15

Leu Lys Asn Glu
            20
```

(2) INFORMATION FOR SEQ ID NO: 2:

(i) SEQUENCE CHARACTERISTICS:
      (A) LENGTH: 750 base pairs
      (B) TYPE: nucleic acid
      (C) STRANDEDNESS: double
      (D) TOPOLOGY: linear (ii) MOLECULE TYPE: genomic DNA (iii) HYPOTHETICAL: NO (iv) ANTI-SENSE: NO (vi) ORIGINAL SOURCE:
      (A) ORGANISM: Morganella morganii
      (B) STRAIN: NCIMB 10466

(ix) FEATURE:
      (A) NAME/KEY: CDS
      (B) LOCATION: 1..747

(ix) FEATURE:
      (A) NAME/KEY: sig_peptide
      (B) LOCATION: 1..60

(ix) FEATURE:
      (A) NAME/KEY:mat_peptide
      (B) LOCATION:61..747

(xi) SEQUENCE DESCRIPTION: SEQ ID NO: 2:

```
ATG AAG AAG AAT ATT ATC GCC GGT TGT CTG TTC TCA CTG TTT TCC CTT      48
Met Lys Lys Asn Ile Ile Ala Gly Cys Leu Phe Ser Leu Phe Ser Leu
-20             -15                 -10                 -5

TCC GCG CTG GCC GCG ATC CCG GCG GGC AAC GAT GCC ACC ACC AAG CCG      96
Ser Ala Leu Ala Ala Ile Pro Ala Gly Asn Asp Ala Thr Thr Lys Pro
                 1               5                  10

GAT TTA TAT TAT CTG AAA AAT GAA CAG GCT ATC GAC AGC CTG AAA CTG     144
Asp Leu Tyr Tyr Leu Lys Asn Glu Gln Ala Ile Asp Ser Leu Lys Leu
            15                  20                  25

TTA CCG CCA CCG CCG GAA GTC GGC AGT ATT CAG TTT TTA AAT GAT CAG     192
Leu Pro Pro Pro Pro Glu Val Gly Ser Ile Gln Phe Leu Asn Asp Gln
        30                  35                  40
```

```
GCA ATG TAT GAG AAA GGC CGT ATG CTG CGC AAT ACC GAG CGC GGA AAA        240
Ala Met Tyr Glu Lys Gly Arg Met Leu Arg Asn Thr Glu Arg Gly Lys
 45              50                  55                  60

CAG GCA CAG GCA GAT GCT GAC CTG GCC GCA GGG GGT GTG GCA ACC GCA        288
Gln Ala Gln Ala Asp Ala Asp Leu Ala Ala Gly Gly Val Ala Thr Ala
                 65                  70                  75

TTT TCA GGG GCA TTC GGC TAT CCG ATA ACC GAA AAA GAC TCT CCG GAG        336
Phe Ser Gly Ala Phe Gly Tyr Pro Ile Thr Glu Lys Asp Ser Pro Glu
             80                  85                  90

CTG TAT AAA CTG CTG ACC AAT ATG ATT GAG GAT GCC GGT GAT CTT GCC        384
Leu Tyr Lys Leu Leu Thr Asn Met Ile Glu Asp Ala Gly Asp Leu Ala
         95                 100                 105

ACC CGC TCC GCC AAA GAA CAT TAC ATG CGC ATC CGG CCG TTT GCG TTT        432
Thr Arg Ser Ala Lys Glu His Tyr Met Arg Ile Arg Pro Phe Ala Phe
110                 115                 120

TAC GGC ACA GAA ACC TGT AAT ACC AAA GAT CAG AAA AAA CTC TCC ACC        480
Tyr Gly Thr Glu Thr Cys Asn Thr Lys Asp Gln Lys Lys Leu Ser Thr
125                 130                 135                 140

AAC GGA TCT TAC CCG TCA GGT CAT ACG TCT ATC GGC TGG GCA ACC GCA        528
Asn Gly Ser Tyr Pro Ser Gly His Thr Ser Ile Gly Trp Ala Thr Ala
                145                 150                 155

CTG GTG CTG GCG GAA GTG AAC CCG GCA AAT CAG GAT GCG ATT CTG GAA        576
Leu Val Leu Ala Glu Val Asn Pro Ala Asn Gln Asp Ala Ile Leu Glu
            160                 165                 170

CGG GGT TAT CAG CTC GGA CAG AGC CGG GTG ATT TGC GGC TAT CAC TGG        624
Arg Gly Tyr Gln Leu Gly Gln Ser Arg Val Ile Cys Gly Tyr His Trp
        175                 180                 185

CAG AGT GAT GTG GAT GCC GCG CGG ATT GTC GGT TCA GCC GCT GTC GCG        672
Gln Ser Asp Val Asp Ala Ala Arg Ile Val Gly Ser Ala Ala Val Ala
190                 195                 200

ACA TTA CAT TCC GAT CCG GCA TTT CAG GCG CAG TTA GCG AAA GCC AAA        720
Thr Leu His Ser Asp Pro Ala Phe Gln Ala Gln Leu Ala Lys Ala Lys
205                 210                 215                 220

CAG GAA TTT GCA CAA AAA TCA CAG AAA TAA                                750
Gln Glu Phe Ala Gln Lys Ser Gln Lys
                225                 229

(2) INFORMATION FOR SEQ ID NO: 3:

(i) SEQUENCE CHARACTERISTICS:
        (A) LENGTH: 249 amino acids
        (B) TYPE: amino acid
        (D) TOPOLOGY: linear (ii) MOLECULE TYPE: protein (vi) ORIGINAL SOURCE:
        (A) ORGANISM: Morganella morganii
        (B) STRAIN: NCIMB 10466

(xi) SEQUENCE DESCRIPTION: SEQ ID NO: 3:

Met Lys Lys Asn Ile Ile Ala Gly Cys Leu Phe Ser Leu Phe Ser Leu
-20             -15                 -10                  -5

Ser Ala Leu Ala Ala Ile Pro Ala Gly Asn Asp Ala Thr Thr Lys Pro
                  1                   5                  10

Asp Leu Tyr Tyr Leu Lys Asn Glu Gln Ala Ile Asp Ser Leu Lys Leu
            15                  20                  25

Leu Pro Pro Pro Glu Val Gly Ser Ile Gln Phe Leu Asn Asp Gln
        30                  35                  40

Ala Met Tyr Glu Lys Gly Arg Met Leu Arg Asn Thr Glu Arg Gly Lys
 45              50                  55                  60
```

```
Gln Ala Gln Ala Asp Ala Asp Leu Ala Ala Gly Gly Val Ala Thr Ala
                    65                  70                  75
Phe Ser Gly Ala Phe Gly Tyr Pro Ile Thr Glu Lys Asp Ser Pro Glu
                80                  85                  90
Leu Tyr Lys Leu Leu Thr Asn Met Ile Glu Asp Ala Gly Asp Leu Ala
            95                 100                 105
Thr Arg Ser Ala Lys Glu His Tyr Met Arg Ile Arg Pro Phe Ala Phe
       110                 115                 120
Tyr Gly Thr Glu Thr Cys Asn Thr Lys Asp Gln Lys Lys Leu Ser Thr
125                 130                 135                 140
Asn Gly Ser Tyr Pro Ser Gly His Thr Ser Ile Gly Trp Ala Thr Ala
                145                 150                 155
Leu Val Leu Ala Glu Val Asn Pro Ala Asn Gln Asp Ala Ile Leu Glu
                160                 165                 170
Arg Gly Tyr Gln Leu Gly Gln Ser Arg Val Ile Cys Gly Tyr His Trp
                175                 180                 185
Gln Ser Asp Val Asp Ala Ala Arg Ile Val Gly Ser Ala Ala Val Ala
                190                 195                 200
Thr Leu His Ser Asp Pro Ala Phe Gln Ala Gln Leu Ala Lys Ala Lys
205                 210                 215                 220
Gln Glu Phe Ala Gln Lys Ser Gln Lys
                225                 229

(2) INFORMATION FOR SEQ ID NO: 4:

(i) SEQUENCE CHARACTERISTICS:
        (A) LENGTH: 229 amino acids
        (B) TYPE: amino acid
        (D) TOPOLOGY: linear (ii) MOLECULE TYPE: protein (vi) ORIGINAL SOURCE:
        (A) ORGANISM: Morganella morganii
        (B) STRAIN: NCIMB 10466

(xi) SEQUENCE DESCRIPTION: SEQ ID NO: 4:

Ala Ile Pro Ala Gly Asn Asp Ala Thr Thr Lys Pro Asp Leu Tyr Tyr
 1               5                  10                  15
Leu Lys Asn Glu Gln Ala Ile Asp Ser Leu Lys Leu Leu Pro Pro Pro
                20                  25                  30
Pro Glu Val Gly Ser Ile Gln Phe Leu Asn Asp Gln Ala Met Tyr Glu
            35                  40                  45
Lys Gly Arg Met Leu Arg Asn Thr Glu Arg Gly Lys Gln Ala Gln Ala
50                  55                  60
Asp Ala Asp Leu Ala Ala Gly Gly Val Ala Thr Ala Phe Ser Gly Ala
65                  70                  75                  80
Phe Gly Tyr Pro Ile Thr Glu Lys Asp Ser Pro Glu Leu Tyr Lys Leu
                85                  90                  95
Leu Thr Asn Met Ile Glu Asp Ala Gly Asp Leu Ala Thr Arg Ser Ala
            100                 105                 110
Lys Glu His Tyr Met Arg Ile Arg Pro Phe Ala Phe Tyr Gly Thr Glu
        115                 120                 125
Thr Cys Asn Thr Lys Asp Gln Lys Lys Leu Ser Thr Asn Gly Ser Tyr
    130                 135                 140
Pro Ser Gly His Thr Ser Ile Gly Trp Ala Thr Ala Leu Val Leu Ala
145                 150                 155                 160
```

```
Glu Val Asn Pro Ala Asn Gln Asp Ala Ile Leu Glu Arg Gly Tyr Gln
            165                 170                 175

Leu Gly Gln Ser Arg Val Ile Cys Gly Tyr His Trp Gln Ser Asp Val
        180                 185                 190

Asp Ala Ala Arg Ile Val Gly Ser Ala Ala Val Ala Thr Leu His Ser
        195                 200                 205

Asp Pro Ala Phe Gln Ala Gln Leu Ala Lys Ala Lys Gln Glu Phe Ala
    210                 215                 220

Gln Lys Ser Gln Lys
225             229
```

(2) INFORMATION FOR SEQ ID NO: 5:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Escherichia blattae
        (B) STRAIN: JCM 1650

(xi) SEQUENCE DESCRIPTION: SEQ ID NO: 5:

```
Leu Ala Leu Val Ala Thr Gly Asn Asp Thr Thr Thr Lys Pro Asp Leu
 1               5                  10                  15
```

(2) INFORMATION FOR SEQ ID NO: 6:

(i) SEQUENCE CHARACTERISTICS:
        (A) LENGTH: 750 base pairs
        (B) TYPE: nucleic acid
        (C) STRANDEDNESS: double
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (A) ORGANISM: Escherichia blattae
        (B) STRAIN: JCM 1650

(ix) FEATURE:
        (A) NAME/KEY: CDS
        (B) LOCATION: 1..747

(ix) FEATURE:
        (A) NAME/KEY: sig_peptide
        (B) LOCATION: 1..54

(ix) FEATURE:
        (A) NAME/KEY: mat_peptide
        (B) LOCATION: 55..747

(xi) SEQUENCE DESCRIPTION: SEQ ID NO: 6:

```
ATG AAA AAA CGT GTT CTG GCA GTT TGT TTT GCC GCA TTG TTC TCT TCT      48
Met Lys Lys Arg Val Leu Ala Val Cys Phe Ala Ala Leu Phe Ser Ser
-18         -15                 -10                 -5

CAG GCC CTG GCG CTG GTC GCT ACC GGC AAC GAC ACT ACC ACG AAA CCG      96
Gln Ala Leu Ala Leu Val Ala Thr Gly Asn Asp Thr Thr Thr Lys Pro
            1               5                   10

GAT CTC TAC TAC CTC AAG AAC AGT GAA GCC ATT AAC AGC CTG GCG CTG     144
```

```
Asp Leu Tyr Tyr Leu Lys Asn Ser Glu Ala Ile Asn Ser Leu Ala Leu
 15                  20                  25                  30

TTG CCG CCA CCA CCG GCG GTG GGC TCC ATT GCG TTT CTC AAC GAT CAG      192
Leu Pro Pro Pro Pro Ala Val Gly Ser Ile Ala Phe Leu Asn Asp Gln
                 35                  40                  45

GCC ATG TAT GAA CAG GGG CGC CTG CTG CGC AAC ACC GAA CGC GGT AAG      240
Ala Met Tyr Glu Gln Gly Arg Leu Leu Arg Asn Thr Glu Arg Gly Lys
             50                  55                  60

CTG GCG GCG GAA GAT GCA AAC CTG AGC AGT GGC GGG GTG GCG AAT GCT      288
Leu Ala Ala Glu Asp Ala Asn Leu Ser Ser Gly Gly Val Ala Asn Ala
             65                  70                  75

TTC TCC GGC GCG TTT GGT AGC CCG ATC ACC GAA AAA GAC GCC CCG GCG      336
Phe Ser Gly Ala Phe Gly Ser Pro Ile Thr Glu Lys Asp Ala Pro Ala
         80                  85                  90

CTG CAT AAA TTA CTG ACC AAT ATG ATT GAG GAC GCC GGG GAT CTG GCG      384
Leu His Lys Leu Leu Thr Asn Met Ile Glu Asp Ala Gly Asp Leu Ala
 95                 100                 105                 110

ACC CGC AGC GCG AAA GAT CAC TAT ATG CGC ATT CGT CCG TTC GCG TTT      432
Thr Arg Ser Ala Lys Asp His Tyr Met Arg Ile Arg Pro Phe Ala Phe
                115                 120                 125

TAT GGG GTC TCT ACC TGT AAT ACC ACC GAG CAG GAC AAA CTG TCC AAA      480
Tyr Gly Val Ser Thr Cys Asn Thr Thr Glu Gln Asp Lys Leu Ser Lys
            130                 135                 140

AAT GGC TCT TAT CCG TCC GGG CAT ACC TCT ATC GGC TGG GCT ACT GCG      528
Asn Gly Ser Tyr Pro Ser Gly His Thr Ser Ile Gly Trp Ala Thr Ala
            145                 150                 155

CTG GTG CTG GCA GAG ATC AAC CCT CAG CGC CAG AAC GAG ATC CTG AAA      576
Leu Val Leu Ala Glu Ile Asn Pro Gln Arg Gln Asn Glu Ile Leu Lys
        160                 165                 170

CGC GGT TAT GAG CTG GGC CAG AGC CGG GTG ATT TGC GGC TAC CAC TGG      624
Arg Gly Tyr Glu Leu Gly Gln Ser Arg Val Ile Cys Gly Tyr His Trp
175                 180                 185                 190

CAG AGT GAT GTG GAT GCC GCG CGG GTA GTG GGA TCT GCC GTT GTG GCG      672
Gln Ser Asp Val Asp Ala Ala Arg Val Val Gly Ser Ala Val Val Ala
                195                 200                 205

ACC CTG CAT ACC AAC CCG GCG TTC CAG CAG CAG TTG CAG AAA GCG AAG      720
Thr Leu His Thr Asn Pro Ala Phe Gln Gln Gln Leu Gln Lys Ala Lys
            210                 215                 220

GCC GAA TTC GCC CAG CAT CAG AAG AAA TAA                              750
Ala Glu Phe Ala Gln His Gln Lys Lys
            225                 230

(2) INFORMATION FOR SEQ ID NO: 7:

(i) SEQUENCE CHARACTERISTICS:
        (A) LENGTH: 249 amino acids
        (B) TYPE: amino acid
        (D) TOPOLOGY: linear (ii) MOLECULE TYPE: protein (vi) ORIGINAL SOURCE:
        (A) ORGANISM: Escherichia blattae
        (B) STRAIN: JCM 1650

(xi) SEQUENCE DESCRIPTION: SEQ ID NO: 7:

Met Lys Lys Arg Val Leu Ala Val Cys Phe Ala Ala Leu Phe Ser Ser
-18             -15                 -10                 -5

Gln Ala Leu Ala Leu Val Ala Thr Gly Asn Asp Thr Thr Thr Lys Pro
 1               5                  10

Asp Leu Tyr Tyr Leu Lys Asn Ser Glu Ala Ile Asn Ser Leu Ala Leu
 15                  20                  25                  30
```

```
Leu Pro Pro Pro Ala Val Gly Ser Ile Ala Phe Leu Asn Asp Gln
            35                  40                  45

Ala Met Tyr Glu Gln Gly Arg Leu Leu Arg Asn Thr Glu Arg Gly Lys
        50                  55                  60

Leu Ala Ala Glu Asp Ala Asn Leu Ser Ser Gly Gly Val Ala Asn Ala
            65                  70                  75

Phe Ser Gly Ala Phe Gly Ser Pro Ile Thr Glu Lys Asp Ala Pro Ala
    80                  85                  90

Leu His Lys Leu Leu Thr Asn Met Ile Glu Asp Ala Gly Asp Leu Ala
95                  100                 105                 110

Thr Arg Ser Ala Lys Asp His Tyr Met Arg Ile Arg Pro Phe Ala Phe
            115                 120                 125

Tyr Gly Val Ser Thr Cys Asn Thr Thr Glu Gln Asp Lys Leu Ser Lys
            130                 135                 140

Asn Gly Ser Tyr Pro Ser Gly His Thr Ser Ile Gly Trp Ala Thr Ala
            145                 150                 155

Leu Val Leu Ala Glu Ile Asn Pro Gln Arg Gln Asn Glu Ile Leu Lys
    160                 165                 170

Arg Gly Tyr Glu Leu Gly Gln Ser Arg Val Ile Cys Gly Tyr His Trp
175                 180                 185                 190

Gln Ser Asp Val Asp Ala Ala Arg Val Val Gly Ser Ala Val Val Ala
            195                 200                 205

Thr Leu His Thr Asn Pro Ala Phe Gln Gln Gln Leu Gln Lys Ala Lys
            210                 215                 220

Ala Glu Phe Ala Gln His Gln Lys Lys
            225                 230

(2) INFORMATION FOR SEQ ID NO: 8:

(i) SEQUENCE CHARACTERISTICS:
        (A) LENGTH: 231 amino acids
        (B) TYPE: amino acid
        (D) TOPOLOGY: linear (ii) MOLECULE TYPE: protein (vi) ORIGINAL SOURCE:
        (A) ORGANISM: Escherichia blattae
        (B) STRAIN: JCM 1650

(xi) SEQUENCE DESCRIPTION: SEQ ID NO: 8:

Leu Ala Leu Val Ala Thr Gly Asn Asp Thr Thr Thr Lys Pro Asp Leu
1               5                   10                  15

Tyr Tyr Leu Lys Asn Ser Glu Ala Ile Asn Ser Leu Ala Leu Leu Pro
            20                  25                  30

Pro Pro Pro Ala Val Gly Ser Ile Ala Phe Leu Asn Asp Gln Ala Met
            35                  40                  45

Tyr Glu Gln Gly Arg Leu Leu Arg Asn Thr Glu Arg Gly Lys Leu Ala
        50                  55                  60

Ala Glu Asp Ala Asn Leu Ser Ser Gly Gly Val Ala Asn Ala Phe Ser
65                  70                  75                  80

Gly Ala Phe Gly Ser Pro Ile Thr Glu Lys Asp Ala Pro Ala Leu His
            85                  90                  95

Lys Leu Leu Thr Asn Met Ile Glu Asp Ala Gly Asp Leu Ala Thr Arg
            100                 105                 110

Ser Ala Lys Asp His Tyr Met Arg Ile Arg Pro Phe Ala Phe Tyr Gly
            115                 120                 125
```

```
Val Ser Thr Cys Asn Thr Thr Glu Gln Asp Lys Leu Ser Lys Asn Gly
    130                 135                 140

Ser Tyr Pro Ser Gly His Thr Ser Ile Gly Trp Ala Thr Ala Leu Val
145                 150                 155                 160

Leu Ala Glu Ile Asn Pro Gln Arg Gln Asn Glu Ile Leu Lys Arg Gly
                165                 170                 175

Tyr Glu Leu Gly Gln Ser Arg Val Ile Cys Gly Tyr His Trp Gln Ser
            180                 185                 190

Asp Val Asp Ala Ala Arg Val Val Gly Ser Ala Val Val Ala Thr Leu
        195                 200                 205

His Thr Asn Pro Ala Phe Gln Gln Gln Leu Gln Lys Ala Lys Ala Glu
    210                 215                 220

Phe Ala Gln His Gln Lys Lys
225                 230
```

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 9:

CCTCGAGGTC GACGGTATCG                                                     20

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other DNA..synthetic DNA (iii) HYPOTHETICAL: NO (iv) ANTI-SENSE: YES (xi) SEQUENCE DESCRIPTION: SEQ ID NO: 10:

ATTCGCCACA TCGCCACTGC T                                               21

(2) INFORMATION FOR SEQ ID NO: 11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 11:

TAGCCCAGCC GGTAGAGGTA TG                                           22

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 12:

TGCATCTGCC TGCGCCTGCT TAC                                  23

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 13:

AACGCGCCGT AGAAAGCATT                                    20

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 14:

GTCCTGGTCT TTGGTATTAC A                                    21

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 15:

CACATCGCCA GCGGCCAGGT CTGCAT                            26

(2) INFORMATION FOR SEQ ID NO: 16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 16:

GCATATAGTG TTCTTTCGCG C                                              21

(2) INFORMATION FOR SEQ ID NO: 17:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 17:

ATTACAGGTT TCGACCCCAT AA                                             22

(2) INFORMATION FOR SEQ ID NO: 18:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 18:

TGATGCATGT CCGGGCTGTC TTTTT                                          25

(2) INFORMATION FOR SEQ ID NO: 19:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other DNA..synthetic DNA (iii) HYPOTHETICAL: NO (iv) ANTI-SENSE: YES (xi) SEQUENCE DESCRIPTION: SEQ ID NO: 19:

CTGGATCCTG TGGCTATCAT CACCT                                          25

(2) INFORMATION FOR SEQ ID NO: 20:

(i) SEQUENCE CHARACTERISTICS:
            (A) LENGTH: 25 base pairs
            (B) TYPE: nucleic acid (C) STRANDEDNESS: single
        (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 20:

CTGGATCCGA CGCGATTTTA CCATA                                              25

(2) INFORMATION FOR SEQ ID NO: 21:

(i) SEQUENCE CHARACTERISTICS:
        (A) LENGTH: 747 base pairs
        (B) TYPE: nucleic acid
        (C) STRANDEDNESS: double
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (A) ORGANISM: Providencia stuartii
        (B) STRAIN: ATCC 29851

(ix) FEATURE:
        (A) NAME/KEY: CDS
        (B) LOCATION: 1..744

(xi) SEQUENCE DESCRIPTION: SEQ ID NO: 21:

```
ATG AAA AAA CTA TTA GCA GTA TTC TGC GCA GGG GCT TTT GTT TCA ACC           48
Met Lys Lys Leu Leu Ala Val Phe Cys Ala Gly Ala Phe Val Ser Thr
 1               5                  10                  15

AGT GTA TTT GCG GCG ATC CCT CCC GGC AAT GAT GTG ACA ACT AAA CCC           96
Ser Val Phe Ala Ala Ile Pro Pro Gly Asn Asp Val Thr Thr Lys Pro
                20                  25                  30

GAT CTT TAT TAT TTA AAA AAC TCA CAG GCT ATT GAT AGT TTA GCG TTA          144
Asp Leu Tyr Tyr Leu Lys Asn Ser Gln Ala Ile Asp Ser Leu Ala Leu
            35                  40                  45

TTG CCG CCA CCA CCT GAA GTG GGC AGT ATC TTA TTT TTA AAC GAC CAA          192
Leu Pro Pro Pro Pro Glu Val Gly Ser Ile Leu Phe Leu Asn Asp Gln
    50                  55                  60

GCG ATG TAT GAA AAA GGC CGT TTA TTG CGA AAT ACT GAG CGT GGA GAA          240
Ala Met Tyr Glu Lys Gly Arg Leu Leu Arg Asn Thr Glu Arg Gly Glu
65                  70                  75                  80

CAA GCC GCT AAG GAT GCT GAT CTG GCT GCG GGC GGT GTT GCG AAC GCA          288
Gln Ala Ala Lys Asp Ala Asp Leu Ala Ala Gly Gly Val Ala Asn Ala
                85                  90                  95

TTT TCT GAA GCT TTT GGT TAT CCC ATT ACC GAA AAG GAT GCG CCT GAA          336
Phe Ser Glu Ala Phe Gly Tyr Pro Ile Thr Glu Lys Asp Ala Pro Glu
                100                 105                 110

ATT CAT AAA TTG CTG ACG AAT ATG ATT GAA GAT GCG GGG GAT TTA GCA          384
Ile His Lys Leu Leu Thr Asn Met Ile Glu Asp Ala Gly Asp Leu Ala
            115                 120                 125

ACT CGC TCA GCC AAA GAG AAA TAC ATG CGC ATT CGT CCA TTT GCG TTC          432
Thr Arg Ser Ala Lys Glu Lys Tyr Met Arg Ile Arg Pro Phe Ala Phe
        130                 135                 140

TAC GGT GTT GCT ACC TGT AAC ACG AAA GAT CAG GAC AAA TTA TCT AAG          480
Tyr Gly Val Ala Thr Cys Asn Thr Lys Asp Gln Asp Lys Leu Ser Lys
145                 150                 155                 160

AAT GGC TCT TAT CCT TCT GGA CAC ACC GCA ATT GGC TGG GCA TCT GCA          528
Asn Gly Ser Tyr Pro Ser Gly His Thr Ala Ile Gly Trp Ala Ser Ala
```

```
                                                                                   -continued Asn Gly Ser Tyr Pro Ser Gly His Thr Ala Ile Gly Trp Ala Ser Ala
                165                 170                 175

CTC GTA TTG TCA GAA ATT AAC CCA GAA AAC CAA GAT AAA ATT TTA AAA        576
Leu Val Leu Ser Glu Ile Asn Pro Glu Asn Gln Asp Lys Ile Leu Lys
            180                 185                 190

CGT GGT TAT GAA CTT GGC CAA AGC CGA GTC ATC TGT GGT TAC CAT TGG        624
Arg Gly Tyr Glu Leu Gly Gln Ser Arg Val Ile Cys Gly Tyr His Trp
        195                 200                 205

CAA AGT GAT GTT GAT GCA GCT CGT ATC GTT GCA TCG GGT GCG GTA GCA        672
Gln Ser Asp Val Asp Ala Ala Arg Ile Val Ala Ser Gly Ala Val Ala
    210                 215                 220

ACT TTA CAC TCC AAC CCT GAA TTC CAA AAA CAG TTA CAA AAA GCC AAA        720
Thr Leu His Ser Asn Pro Glu Phe Gln Lys Gln Leu Gln Lys Ala Lys
225                 230                 235                 240

GAC GAA TTT GCT AAA CTG AAA AAA TAG                                    747
Asp Glu Phe Ala Lys Leu Lys Lys
                245

(2) INFORMATION FOR SEQ ID NO: 22:

(i) SEQUENCE CHARACTERISTICS:
        (A) LENGTH: 248 amino acids
        (B) TYPE: amino acid
        (D) TOPOLOGY: linear (ii) MOLECULE TYPE: protein (vi) ORIGINAL SOURCE:
         (A) ORGANISM: Providencia stuartii
         (B) STRAIN: ATCC 29851

(xi) SEQUENCE DESCRIPTION: SEQ ID NO: 22:

Met Lys Lys Leu Leu Ala Val Phe Cys Ala Gly Ala Phe Val Ser Thr
  1               5                  10                  15

Ser Val Phe Ala Ala Ile Pro Pro Gly Asn Asp Val Thr Thr Lys Pro
                20                  25                  30

Asp Leu Tyr Tyr Leu Lys Asn Ser Gln Ala Ile Asp Ser Leu Ala Leu
            35                  40                  45

Leu Pro Pro Pro Glu Val Gly Ser Ile Leu Phe Leu Asn Asp Gln
        50                  55                  60

Ala Met Tyr Glu Lys Gly Arg Leu Leu Arg Asn Thr Glu Arg Gly Glu
 65                 70                  75                  80

Gln Ala Ala Lys Asp Ala Asp Leu Ala Ala Gly Val Ala Asn Ala
                85                  90                  95

Phe Ser Glu Ala Phe Gly Tyr Pro Ile Thr Glu Lys Asp Ala Pro Glu
                100                 105                 110

Ile His Lys Leu Leu Thr Asn Met Ile Glu Asp Ala Gly Asp Leu Ala
            115                 120                 125

Thr Arg Ser Ala Lys Glu Lys Tyr Met Arg Ile Arg Pro Phe Ala Phe
        130                 135                 140

Tyr Gly Val Ala Thr Cys Asn Thr Lys Asp Gln Asp Lys Leu Ser Lys
145                 150                 155                 160

Asn Gly Ser Tyr Pro Ser Gly His Thr Ala Ile Gly Trp Ala Ser Ala
                165                 170                 175

Leu Val Leu Ser Glu Ile Asn Pro Glu Asn Gln Asp Lys Ile Leu Lys
            180                 185                 190

Arg Gly Tyr Glu Leu Gly Gln Ser Arg Val Ile Cys Gly Tyr His Trp
        195                 200                 205

Gln Ser Asp Val Asp Ala Ala Arg Ile Val Ala Ser Gly Ala Val Ala
```

```
              210                 215                 220
Thr Leu His Ser Asn Pro Glu Phe Gln Lys Gln Leu Gln Lys Ala Lys
225                 230                 235                 240

Asp Glu Phe Ala Lys Leu Lys Lys
                245
```

(2) INFORMATION FOR SEQ ID NO: 23:

(i) SEQUENCE CHARACTERISTICS:
        (A) LENGTH: 747 base pairs
        (B) TYPE: nucleic acid
        (C) STRANDEDNESS: double
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (A) ORGANISM: Enterobacter aerogenes
        (B) STRAIN: IFO 12010

(ix) FEATURE:
        (A) NAME/KEY: CDS
        (B) LOCATION: 1..744

(xi) SEQUENCE DESCRIPTION: SEQ ID NO: 23:

```
ATG AAA AAG CGC GTT CTC GCC CTC TGC CTC GCC AGC CTG TTT TCC GTT      48
Met Lys Lys Arg Val Leu Ala Leu Cys Leu Ala Ser Leu Phe Ser Val
 1               5                  10                  15

AAC GCT TTC GCG CTG GTC CCT GCC GGC AAT GAT GCA ACC ACC AAA CCG      96
Asn Ala Phe Ala Leu Val Pro Ala Gly Asn Asp Ala Thr Thr Lys Pro
             20                  25                  30

GAT CTC TAT TAT CTG AAA AAT GCA CAG GCC ATC GAT AGT CTG GCG CTG     144
Asp Leu Tyr Tyr Leu Lys Asn Ala Gln Ala Ile Asp Ser Leu Ala Leu
         35                  40                  45

TTG CCG CCG CCG CCG GAA GTT GGC AGC ATC GCA TTT TTA AAC GAT CAG     192
Leu Pro Pro Pro Pro Glu Val Gly Ser Ile Ala Phe Leu Asn Asp Gln
     50                  55                  60

GCG ATG TAT GAG AAA GGA CGG CTG TTG CGC AAT ACC GAA CGT GGC AAG     240
Ala Met Tyr Glu Lys Gly Arg Leu Leu Arg Asn Thr Glu Arg Gly Lys
 65                  70                  75                  80

CTG GCG GCT GAA GAT GCT AAC CTG AGC GCC GGC GGC GTC GCG AAT GCC     288
Leu Ala Ala Glu Asp Ala Asn Leu Ser Ala Gly Gly Val Ala Asn Ala
                 85                  90                  95

TTC TCC AGC GCT TTT GGT TCG CCC ATC ACC GAA AAA GAC GCG CCG CAG     336
Phe Ser Ser Ala Phe Gly Ser Pro Ile Thr Glu Lys Asp Ala Pro Gln
            100                 105                 110

TTA CAT AAG CTG CTG ACA AAT ATG ATT GAG GAT GCC GGC GAT CTG GCC     384
Leu His Lys Leu Leu Thr Asn Met Ile Glu Asp Ala Gly Asp Leu Ala
        115                 120                 125

ACC CGC AGC GCG AAA GAG AAA TAT ATG CGC ATT CGC CCG TTT GCG TTC     432
Thr Arg Ser Ala Lys Glu Lys Tyr Met Arg Ile Arg Pro Phe Ala Phe
    130                 135                 140

TAC GGC GTT TCA ACC TGT AAC ACT ACC GAG CAG GAC AAG CTG TCG AAA     480
Tyr Gly Val Ser Thr Cys Asn Thr Thr Glu Gln Asp Lys Leu Ser Lys
145                 150                 155                 160

AAC GGA TCT TAC CCT TCC GGC CAT ACC TCT ATC GGT TGG GCA ACC GCG     528
Asn Gly Ser Tyr Pro Ser Gly His Thr Ser Ile Gly Trp Ala Thr Ala
                165                 170                 175

CTG GTA CTG GCG GAG ATC AAT CCG CAG CGG CAA AAC GAA ATT CTC AAA     576
Leu Val Leu Ala Glu Ile Asn Pro Gln Arg Gln Asn Glu Ile Leu Lys
```

```
                 180             185             190
CGC GGC TAT GAA TTG GGC GAA AGC CGG GTT ATC TGC GGC TAT CAT TGG    624
Arg Gly Tyr Glu Leu Gly Glu Ser Arg Val Ile Cys Gly Tyr His Trp
        195             200             205

CAG AGC GAT GTC GAT GCG GCG CGG ATA GTC GGC TCG GCG GTG GTG GCG    672
Gln Ser Asp Val Asp Ala Ala Arg Ile Val Gly Ser Ala Val Val Ala
        210             215             220

ACC CTG CAT ACC AAC CCG GCC TTC CAA CAG CAG TTG CAG AAA GCA AAG    720
Thr Leu His Thr Asn Pro Ala Phe Gln Gln Gln Leu Gln Lys Ala Lys
225             230             235             240

GAT GAA TTC GCC AAA ACG CAG AAG TAA                                747
Asp Glu Phe Ala Lys Thr Gln Lys
            245
```

(2) INFORMATION FOR SEQ ID NO: 24:

(i) SEQUENCE CHARACTERISTICS:
        (A) LENGTH: 248 amino acids
        (B) TYPE: amino acid
        (D) TOPOLOGY: linear (ii) MOLECULE TYPE: protein (vi) ORIGINAL SOURCE:
        (A) ORGANISM: Enterobacter aerogenes
        (B) STRAIN: IFO 12010

(xi) SEQUENCE DESCRIPTION: SEQ ID NO: 24:

```
Met Lys Lys Arg Val Leu Ala Leu Cys Leu Ala Ser Leu Phe Ser Val
 1               5                  10                  15

Asn Ala Phe Ala Leu Val Pro Ala Gly Asn Asp Ala Thr Thr Lys Pro
            20                  25                  30

Asp Leu Tyr Tyr Leu Lys Asn Ala Gln Ala Ile Asp Ser Leu Ala Leu
        35                  40                  45

Leu Pro Pro Pro Glu Val Gly Ser Ile Ala Phe Leu Asn Asp Gln
    50                  55                  60

Ala Met Tyr Glu Lys Gly Arg Leu Leu Arg Asn Thr Glu Arg Gly Lys
65                  70                  75                  80

Leu Ala Ala Glu Asp Ala Asn Leu Ser Ala Gly Gly Val Ala Asn Ala
                85                  90                  95

Phe Ser Ser Ala Phe Gly Ser Pro Ile Thr Glu Lys Asp Ala Pro Gln
            100                 105                 110

Leu His Lys Leu Leu Thr Asn Met Ile Glu Asp Ala Gly Asp Leu Ala
        115                 120                 125

Thr Arg Ser Ala Lys Glu Lys Tyr Met Arg Ile Arg Pro Phe Ala Phe
130                 135                 140

Tyr Gly Val Ser Thr Cys Asn Thr Thr Glu Gln Asp Lys Leu Ser Lys
145                 150                 155                 160

Asn Gly Ser Tyr Pro Ser Gly His Thr Ser Ile Gly Trp Ala Thr Ala
                165                 170                 175

Leu Val Leu Ala Glu Ile Asn Pro Gln Arg Gln Asn Glu Ile Leu Lys
            180                 185                 190

Arg Gly Tyr Glu Leu Gly Glu Ser Arg Val Ile Cys Gly Tyr His Trp
        195                 200                 205

Gln Ser Asp Val Asp Ala Ala Arg Ile Val Gly Ser Ala Val Val Ala
        210                 215                 220

Thr Leu His Thr Asn Pro Ala Phe Gln Gln Gln Leu Gln Lys Ala Lys
225                 230                 235                 240
```

Asp Glu Phe Ala Lys Thr Gln Lys
            245

(2) INFORMATION FOR SEQ ID NO: 25:

(i) SEQUENCE CHARACTERISTICS:
        (A) LENGTH: 747 base pairs
        (B) TYPE: nucleic acid
        (C) STRANDEDNESS: double
        (D) TOPOLOGY: linear (ii) MOLECULE TYPE: genomic DNA (iii) HYPOTHETICAL: NO (iv) ANTI-SENSE: NO (vi) ORIGINAL SOURCE:
        (A) ORGANISM: Klevsiella planticola
        (B) STRAIN: IFO 14939

(ix) FEATURE:
        (A) NAME/KEY: CDS
        (B) LOCATION: 1..747

(xi) SEQUENCE DESCRIPTION: SEQ ID NO: 25:

```
ATG AAA AAG CGT GTA CTC GCC CTT TGC CTT GCC AGC CTC TTT TCA GTT        48
Met Lys Lys Arg Val Leu Ala Leu Cys Leu Ala Ser Leu Phe Ser Val
 1               5                  10                  15

AGC GCC TTT GCG CTG GTT CCC GCC GGC AAT GAT GCC ACC ACC AAG CCC        96
Ser Ala Phe Ala Leu Val Pro Ala Gly Asn Asp Ala Thr Thr Lys Pro
             20                  25                  30

GAT CTC TAC TAT CTG AAA AAT GCC CAG GCC ATT GAC AGC CTG GCG CTG       144
Asp Leu Tyr Tyr Leu Lys Asn Ala Gln Ala Ile Asp Ser Leu Ala Leu
         35                  40                  45

TTG CCA CCG CCG CCG GAA GTG GGC AGC ATT GCG TTT TTA AAC GAT CAG       192
Leu Pro Pro Pro Pro Glu Val Gly Ser Ile Ala Phe Leu Asn Asp Gln
     50                  55                  60

GCG ATG TAT GAG AAA GGC CGT CTG CTG CGC GCC ACC GCC CGC GGC AAG       240
Ala Met Tyr Glu Lys Gly Arg Leu Leu Arg Ala Thr Ala Arg Gly Lys
 65                  70                  75                  80

TTG GCG GCA GAA GAT GCC AAC CTG AGC GCG GGT GGC GTG GCC AAC GCC       288
Leu Ala Ala Glu Asp Ala Asn Leu Ser Ala Gly Gly Val Ala Asn Ala
                 85                  90                  95

TTC TCC GCA GCA TTC GGC TCC CCG ATC AGC GAA AAA GAC GCC CCG GCG       336
Phe Ser Ala Ala Phe Gly Ser Pro Ile Ser Glu Lys Asp Ala Pro Ala
            100                 105                 110

CTG CAC AAA CTG CTC ACC AAC ATG ATT GAA GAC GCG GGC GAT CTG GCG       384
Leu His Lys Leu Leu Thr Asn Met Ile Glu Asp Ala Gly Asp Leu Ala
        115                 120                 125

ACC CGA GGC GCG AAA GAG AAG TAT ATG CGT ATT CGT CCG TTT GCC TTC       432
Thr Arg Gly Ala Lys Glu Lys Tyr Met Arg Ile Arg Pro Phe Ala Phe
    130                 135                 140

TAC GGC GTG TCC ACC TGC AAT ACC ACC GAA CAG GAT AAG CTG TCG AAA       480
Tyr Gly Val Ser Thr Cys Asn Thr Thr Glu Gln Asp Lys Leu Ser Lys
145                 150                 155                 160

AAC GGC TCC TAC CCT TCC GGA CAC ACC TCT ATC GGC TGG GCG ACC GCC       528
Asn Gly Ser Tyr Pro Ser Gly His Thr Ser Ile Gly Trp Ala Thr Ala
                165                 170                 175

CTG GTG CTG GCC GAA ATC AAC CCG CAG CGC CAG AAT GAG ATT CTC AAG       576
Leu Val Leu Ala Glu Ile Asn Pro Gln Arg Gln Asn Glu Ile Leu Lys
            180                 185                 190

CGC GGC TAT GAG CTC GGT GAA AGT CGG GTG ATC TGC GGT TAC CAC TGG       624
Arg Gly Tyr Glu Leu Gly Glu Ser Arg Val Ile Cys Gly Tyr His Trp
        195                 200                 205
```

```
CAG AGC GAT GTT GAC GCC GCG CGG ATT GTC GGC TCG GCG GTG GTT GCA      672
Gln Ser Asp Val Asp Ala Ala Arg Ile Val Gly Ser Ala Val Val Ala
        210                 215                 220

ACC CTG CAT ACC AAT CCG GCC TTC CAG CAG CAG CTG CAA AAA GCC AAA      720
Thr Leu His Thr Asn Pro Ala Phe Gln Gln Gln Leu Gln Lys Ala Lys
225                 230                 235                 240

GAC GAG TTT GCG AAA CAG CAG AAA TAG                                  747
Asp Glu Phe Ala Lys Gln Gln Lys
                245
```

(2) INFORMATION FOR SEQ ID NO: 26:

(i) SEQUENCE CHARACTERISTICS:
        (A) LENGTH: 248 amino acids
        (B) TYPE: amino acid
        (D) TOPOLOGY: linear (ii) MOLECULE TYPE: protein (vi) ORIGINAL SOURCE:
        (A) ORGANISM: Klevsiella planticola
        (B) STRAIN: IFO 14939

(xi) SEQUENCE DESCRIPTION: SEQ ID NO: 26:

```
Met Lys Lys Arg Val Leu Ala Leu Cys Leu Ala Ser Leu Phe Ser Val
 1               5                  10                  15

Ser Ala Phe Ala Leu Val Pro Ala Gly Asn Asp Ala Thr Thr Lys Pro
                20                  25                  30

Asp Leu Tyr Tyr Leu Lys Asn Ala Gln Ala Ile Asp Ser Leu Ala Leu
            35                  40                  45

Leu Pro Pro Pro Pro Glu Val Gly Ser Ile Ala Phe Leu Asn Asp Gln
        50                  55                  60

Ala Met Tyr Glu Lys Gly Arg Leu Leu Arg Ala Thr Ala Arg Gly Lys
65                  70                  75                  80

Leu Ala Ala Glu Asp Ala Asn Leu Ser Ala Gly Gly Val Ala Asn Ala
                85                  90                  95

Phe Ser Ala Ala Phe Gly Ser Pro Ile Ser Glu Lys Asp Ala Pro Ala
                100                 105                 110

Leu His Lys Leu Leu Thr Asn Met Ile Glu Asp Ala Gly Asp Leu Ala
            115                 120                 125

Thr Arg Gly Ala Lys Glu Lys Tyr Met Arg Ile Arg Pro Phe Ala Phe
        130                 135                 140

Tyr Gly Val Ser Thr Cys Asn Thr Thr Glu Gln Asp Lys Leu Ser Lys
145                 150                 155                 160

Asn Gly Ser Tyr Pro Ser Gly His Thr Ser Ile Gly Trp Ala Thr Ala
                165                 170                 175

Leu Val Leu Ala Glu Ile Asn Pro Gln Arg Gln Asn Glu Ile Leu Lys
            180                 185                 190

Arg Gly Tyr Glu Leu Gly Glu Ser Arg Val Ile Cys Gly Tyr His Trp
        195                 200                 205

Gln Ser Asp Val Asp Ala Ala Arg Ile Val Gly Ser Ala Val Val Ala
                210                 215                 220

Thr Leu His Thr Asn Pro Ala Phe Gln Gln Gln Leu Gln Lys Ala Lys
225                 230                 235                 240

Asp Glu Phe Ala Lys Gln Gln Lys
                245
```

(2) INFORMATION FOR SEQ ID NO: 27:

(i) SEQUENCE CHARACTERISTICS:
    (A) LENGTH: 735 base pairs
    (B) TYPE: nucleic acid
    (C) STRANDEDNESS: double
    (D) TOPOLOGY: linear (ii) MOLECULE TYPE: genomic DNA (iii) HYPOTHETICAL: NO (iv) ANTI-SENSE: NO (vi) ORIGINAL SOURCE:
    (A) ORGANISM: Serratia ficaria
    (B) STRAIN: IAM 13540

(ix) FEATURE:
    (A) NAME/KEY: CDS
    (B) LOCATION: 1..732

(xi) SEQUENCE DESCRIPTION: SEQ ID NO: 27:

| | | | | | | | | | | | | | | | | |
|---|---|---|---|---|---|---|---|---|---|---|---|---|---|---|---|---|
| ATG | AAA | AAA | ATA | TTA | TTA | GCC | ACA | TTA | AGC | TGC | GCC | GCG | TTG | ACG | CAG | 48 |
| Met | Lys | Lys | Ile | Leu | Leu | Ala | Thr | Leu | Ser | Cys | Ala | Ala | Leu | Thr | Gln | |
| 1 | | | | 5 | | | | | 10 | | | | | 15 | | |
| TTT | TCC | TTT | GCC | GCC | AAA | GAT | GTC | ACT | ACC | CAC | CCT | GAG | GTT | TAT | TTT | 96 |
| Phe | Ser | Phe | Ala | Ala | Lys | Asp | Val | Thr | Thr | His | Pro | Glu | Val | Tyr | Phe | |
| | | | 20 | | | | | 25 | | | | | 30 | | | |
| CTG | CAA | GAA | TCA | CAG | TCC | ATC | GAC | AGC | CTG | GCA | CTA | TTG | CCG | CCG | CCG | 144 |
| Leu | Gln | Glu | Ser | Gln | Ser | Ile | Asp | Ser | Leu | Ala | Leu | Leu | Pro | Pro | Pro | |
| | | | 35 | | | | | 40 | | | | | 45 | | | |
| CCG | GCG | ATG | GAC | AGC | ATT | GAT | TTC | CTG | AAT | GAC | AAA | GCG | CAA | TAC | GAC | 192 |
| Pro | Ala | Met | Asp | Ser | Ile | Asp | Phe | Leu | Asn | Asp | Lys | Ala | Gln | Tyr | Asp | |
| | | 50 | | | | | 55 | | | | | 60 | | | | |
| GCC | GGG | AAA | ATA | GTG | CGC | AAT | ACT | CCG | CGT | GGC | AAG | CAG | GCT | TAT | GAT | 240 |
| Ala | Gly | Lys | Ile | Val | Arg | Asn | Thr | Pro | Arg | Gly | Lys | Gln | Ala | Tyr | Asp | |
| 65 | | | | | 70 | | | | | 75 | | | | | 80 | |
| GAC | GCC | CAC | GTT | GCC | GGG | GAC | GGC | GTT | GCC | GCC | GCA | TTT | TCC | AAC | GCC | 288 |
| Asp | Ala | His | Val | Ala | Gly | Asp | Gly | Val | Ala | Ala | Ala | Phe | Ser | Asn | Ala | |
| | | | | 85 | | | | | 90 | | | | | 95 | | |
| TTC | GGC | CTA | GAA | ATA | GCC | CAA | CGG | AAA | ACG | CCG | GAG | CTG | TTT | AAG | CTG | 336 |
| Phe | Gly | Leu | Glu | Ile | Ala | Gln | Arg | Lys | Thr | Pro | Glu | Leu | Phe | Lys | Leu | |
| | | | | 100 | | | | | 105 | | | | | 110 | | |
| GTG | ATG | AAA | ATG | CGT | GAA | GAC | GCC | GGC | GAT | TTG | GCG | ACC | CGC | AGC | GCC | 384 |
| Val | Met | Lys | Met | Arg | Glu | Asp | Ala | Gly | Asp | Leu | Ala | Thr | Arg | Ser | Ala | |
| | | | 115 | | | | | 120 | | | | | 125 | | | |
| AAA | AAT | CAC | TAT | ATG | CGC | ATT | CGC | CCC | TTT | GCG | TTT | TAT | AAC | GAA | GCG | 432 |
| Lys | Asn | His | Tyr | Met | Arg | Ile | Arg | Pro | Phe | Ala | Phe | Tyr | Asn | Glu | Ala | |
| | 130 | | | | | 135 | | | | | 140 | | | | | |
| ACC | TGC | CGA | CCG | GAC | GAA | GAA | AGC | ACC | CTG | TCG | AAG | AAC | GGT | TCT | TAC | 480 |
| Thr | Cys | Arg | Pro | Asp | Glu | Glu | Ser | Thr | Leu | Ser | Lys | Asn | Gly | Ser | Tyr | |
| 145 | | | | | 150 | | | | | 155 | | | | | 160 | |
| CCT | TCC | GGC | CAT | ACC | ACC | ATC | GGC | TGG | GCG | ACC | GCG | CTG | GTG | CTG | GCT | 528 |
| Pro | Ser | Gly | His | Thr | Thr | Ile | Gly | Trp | Ala | Thr | Ala | Leu | Val | Leu | Ala | |
| | | | | 165 | | | | | 170 | | | | | 175 | | |
| GAA | ATC | AAC | CCC | GCC | AGG | CAG | GGT | GAA | ATC | CTG | CAG | CGC | GGC | TAT | GAT | 576 |
| Glu | Ile | Asn | Pro | Ala | Arg | Gln | Gly | Glu | Ile | Leu | Gln | Arg | Gly | Tyr | Asp | |
| | | | | 180 | | | | | 185 | | | | | 190 | | |
| ATG | GGC | CAA | AGC | CGG | GTT | ATC | TGC | GGT | TAT | CAC | TGG | CAA | AGC | GAC | GTG | 624 |
| Met | Gly | Gln | Ser | Arg | Val | Ile | Cys | Gly | Tyr | His | Trp | Gln | Ser | Asp | Val | |
| | | | 195 | | | | | 200 | | | | | 205 | | | |
| ACT | GCG | GCG | CGC | ATG | GCG | GCG | TCG | GCC | ATG | GTG | GCG | CGT | TTG | CAT | GCC | 672 |
| Thr | Ala | Ala | Arg | Met | Ala | Ala | Ser | Ala | Met | Val | Ala | Arg | Leu | His | Ala | |
| | 210 | | | | | 215 | | | | | 220 | | | | | |

```
GAA CCC ACC TTC GCC GCC CAG CTG CAA AAG GCC AAA GAC GAA TTC AAC       720
Glu Pro Thr Phe Ala Ala Gln Leu Gln Lys Ala Lys Asp Glu Phe Asn
225             230                 235                 240

GGC CTG AAA AAG TAA                                                   735
Gly Leu Lys Lys
```

(2) INFORMATION FOR SEQ ID NO: 28:

(i) SEQUENCE CHARACTERISTICS:
        (A) LENGTH: 244 amino acids
        (B) TYPE: amino acid
        (D) TOPOLOGY: linear (ii) MOLECULE TYPE: protein (vi) ORIGINAL SOURCE:
        (A) ORGANISM: Serratia ficaria
        (B) STRAIN: IAM 13540

(xi) SEQUENCE DESCRIPTION: SEQ ID NO: 28:

```
Met Lys Lys Ile Leu Leu Ala Thr Leu Ser Cys Ala Ala Leu Thr Gln
 1               5                  10                  15

Phe Ser Phe Ala Ala Lys Asp Val Thr Thr His Pro Glu Val Tyr Phe
                20                  25                  30

Leu Gln Glu Ser Gln Ser Ile Asp Ser Leu Ala Leu Leu Pro Pro Pro
            35                  40                  45

Pro Ala Met Asp Ser Ile Asp Phe Leu Asn Asp Lys Ala Gln Tyr Asp
        50                  55                  60

Ala Gly Lys Ile Val Arg Asn Thr Pro Arg Gly Lys Gln Ala Tyr Asp
65                  70                  75                  80

Asp Ala His Val Ala Gly Asp Gly Val Ala Ala Ala Phe Ser Asn Ala
                85                  90                  95

Phe Gly Leu Glu Ile Ala Gln Arg Lys Thr Pro Glu Leu Phe Lys Leu
            100                 105                 110

Val Met Lys Met Arg Glu Asp Ala Gly Asp Leu Ala Thr Arg Ser Ala
        115                 120                 125

Lys Asn His Tyr Met Arg Ile Arg Pro Phe Ala Phe Tyr Asn Glu Ala
    130                 135                 140

Thr Cys Arg Pro Asp Glu Glu Ser Thr Leu Ser Lys Asn Gly Ser Tyr
145                 150                 155                 160

Pro Ser Gly His Thr Thr Ile Gly Trp Ala Thr Ala Leu Val Leu Ala
                165                 170                 175

Glu Ile Asn Pro Ala Arg Gln Gly Glu Ile Leu Gln Arg Gly Tyr Asp
            180                 185                 190

Met Gly Gln Ser Arg Val Ile Cys Gly Tyr His Trp Gln Ser Asp Val
        195                 200                 205

Thr Ala Ala Arg Met Ala Ala Ser Ala Met Val Ala Arg Leu His Ala
    210                 215                 220

Glu Pro Thr Phe Ala Ala Gln Leu Gln Lys Ala Lys Asp Glu Phe Asn
225                 230                 235                 240

Gly Leu Lys Lys
```

(2) INFORMATION FOR SEQ ID NO: 29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear

```
        (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 29:

CCCGGCGTCA CCAATCATAT T                                              21

(2) INFORMATION FOR SEQ ID NO: 30:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other DNA..synthetic DNA (iii) HYPOTHETICAL: NO (iv) ANTI-SENSE: NO (xi) SEQUENCE DESCRIPTION: SEQ ID NO: 30:

GCCGGTAGAG GCATGCCCGG A                                              21
```